US011643472B2

United States Patent
Helsen et al.

(10) Patent No.: US 11,643,472 B2
(45) Date of Patent: *May 9, 2023

(54) T CELL-ANTIGEN COUPLER WITH Y182T MUTATION AND METHODS AND USES THEREOF

(71) Applicant: McMaster University, Hamilton (CA)

(72) Inventors: Christopher W. Helsen, Oakville (CA); Jonathan Bramson, Oakville (CA); Anna Dvorkin-Gheva, Burlington (CA); Galina F. Denisova, Hamilton (CA); Ksenia Bezverbnaya, Hamilton (CA); Kenneth Anthony Mwawasi, Hamilton (CA)

(73) Assignee: McMaster University, Hamilton (CA)

( * ) Notice: Subject to any disclaimer, the term of this patent is extended or adjusted under 35 U.S.C. 154(b) by 428 days.

This patent is subject to a terminal disclaimer.

(21) Appl. No.: 16/753,577

(22) PCT Filed: Oct. 12, 2018

(86) PCT No.: PCT/CA2018/051290
§ 371 (c)(1),
(2) Date: Apr. 3, 2020

(87) PCT Pub. No.: WO2019/071358
PCT Pub. Date: Apr. 18, 2019

(65) Prior Publication Data
US 2020/0392247 A1    Dec. 17, 2020

Related U.S. Application Data

(60) Provisional application No. 62/571,354, filed on Oct. 12, 2017.

(51) Int. Cl.
| | |
|---|---|
| C07K 16/30 | (2006.01) |
| A61P 35/00 | (2006.01) |
| A61K 9/00 | (2006.01) |
| A61K 38/00 | (2006.01) |
| C07K 14/725 | (2006.01) |
| C07K 14/73 | (2006.01) |
| C07K 16/28 | (2006.01) |
| A61K 39/385 | (2006.01) |
| C07K 14/525 | (2006.01) |
| C07K 14/705 | (2006.01) |

(52) U.S. Cl.
CPC ........ *C07K 16/3061* (2013.01); *A61K 9/0019* (2013.01); *A61K 38/00* (2013.01); *A61K 39/385* (2013.01); *A61P 35/00* (2018.01); *C07K 14/525* (2013.01); *C07K 14/7051* (2013.01); *C07K 14/70514* (2013.01); *C07K 14/70517* (2013.01); *C07K 16/2809* (2013.01)

(58) Field of Classification Search
CPC ............ C07K 16/3061; C07K 14/7051; C07K 14/525; C07K 16/2809; C07K 14/70517; C07K 14/70514; A61K 39/385; A61K 38/00; A61K 9/0019; A61P 35/00
See application file for complete search history.

(56) References Cited

U.S. PATENT DOCUMENTS

| | | | |
|---|---|---|---|
| 7,083,785 | B2 | 8/2006 | Browning et al. |
| 7,947,805 | B2 | 5/2011 | Belloir et al. |
| 8,084,030 | B2 | 12/2011 | Kalled et al. |
| 9,718,893 | B2 | 8/2017 | Jung et al. |
| 10,435,453 | B2 | 10/2019 | Bramson et al. |
| 10,640,562 | B2 | 5/2020 | Bramson et al. |
| 10,822,408 | B2 | 11/2020 | Hamburger et al. |
| 11,001,621 | B1 | 5/2021 | Bramson et al. |
| 11,008,376 | B2 | 5/2021 | Bramson et al. |
| 11,110,123 | B2 | 9/2021 | Bramson et al. |
| 11,111,298 | B2 | 9/2021 | Bramson et al. |
| 11,198,737 | B2 | 12/2021 | Helsen et al. |
| 2002/0081296 | A1 | 6/2002 | Theill et al. |
| 2002/0107869 | A1 | 8/2002 | Leroy |
| 2003/0012783 | A1 | 1/2003 | Kindsvogel |
| 2003/0095967 | A1 | 5/2003 | MacKay et al. |
| 2004/0162411 | A1 | 8/2004 | Lanzavecchia |
| 2006/0233791 | A1 | 10/2006 | Tedder et al. |
| 2007/0048221 | A1 | 3/2007 | Kindsvogel |
| 2007/0048319 | A1 | 3/2007 | Kindsvogel |
| 2007/0049735 | A1 | 3/2007 | Kindsvogel |
| 2008/0044413 | A1 | 2/2008 | Hammond et al. |
| 2008/0095766 | A1 | 4/2008 | Koenig et al. |

(Continued)

FOREIGN PATENT DOCUMENTS

| | | |
|---|---|---|
| WO | WO-9957268 A1 | 11/1999 |
| WO | WO-2004106380 A2 | 12/2004 |

(Continued)

OTHER PUBLICATIONS

Acuto et al. T cell activation and the cytoskeleton. Annu. Rev. Immunol. 18:165-184 (2000).

(Continued)

*Primary Examiner* — Amy E Juedes
*Assistant Examiner* — Brian Hartnett
(74) *Attorney, Agent, or Firm* — Goodwin Procter LLP

(57) ABSTRACT

A trifunctional molecule comprising a target-specific ligand, a ligand that binds a protein associated with the TCR complex and a T cell receptor signaling domain polypeptide is provided. The ligand that binds a protein associated with a TCR complex is UCHT1 with a Y182T mutation. Engineering T cells with this novel receptor engenders antigen specific activation of numerous T cell functions, including cytokine production, degranulation and cytolysis.

10 Claims, 20 Drawing Sheets

Specification includes a Sequence Listing.

(56) References Cited

U.S. PATENT DOCUMENTS

| | | |
|---|---|---|
| 2008/0260737 A1 | 10/2008 | Ponce et al. |
| 2008/0267965 A1 | 10/2008 | Kalled et al. |
| 2012/0082661 A1 | 4/2012 | Kalled et al. |
| 2012/0213768 A1 | 8/2012 | Oh et al. |
| 2013/0101599 A1 | 4/2013 | Borges et al. |
| 2013/0156770 A1 | 6/2013 | Kufer et al. |
| 2013/0273055 A1 | 10/2013 | Borges et al. |
| 2013/0280280 A1 | 10/2013 | Algate et al. |
| 2013/0330323 A1 | 12/2013 | Dunn et al. |
| 2015/0119555 A1 | 4/2015 | Jung et al. |
| 2015/0322169 A1 | 11/2015 | June et al. |
| 2016/0228546 A1 | 8/2016 | Stagliano et al. |
| 2016/0362472 A1 | 12/2016 | Bitter et al. |
| 2016/0368964 A1 | 12/2016 | Bramson et al. |
| 2019/0153115 A1 | 5/2019 | Schellenberger et al. |
| 2020/0024345 A1 | 1/2020 | Bramson et al. |
| 2020/0071377 A1 | 3/2020 | Bramson et al. |
| 2020/0239571 A1 | 7/2020 | Bramson et al. |
| 2020/0261500 A1 | 8/2020 | Bramson et al. |
| 2020/0270330 A1 | 8/2020 | Bramson et al. |
| 2020/0308278 A1 | 10/2020 | Bramson et al. |
| 2021/0369780 A1 | 12/2021 | Bramson et al. |

FOREIGN PATENT DOCUMENTS

| | | |
|---|---|---|
| WO | WO-2005040220 A1 | 5/2005 |
| WO | WO-2010037835 A2 | 4/2010 |
| WO | WO-2012066058 A1 | 5/2012 |
| WO | WO-2012163805 A1 | 12/2012 |
| WO | WO-2013092001 A1 | 6/2013 |
| WO | WO-2013123061 A1 | 8/2013 |
| WO | WO-2013132268 A1 | 9/2013 |
| WO | WO-2014011988 A2 | 1/2014 |
| WO | WO-2014122144 A1 | 8/2014 |
| WO | WO-2015006749 A2 | 1/2015 |
| WO | WO-2015117229 A1 | 8/2015 |
| WO | WO-2016166139 A1 | 10/2016 |
| WO | WO-2017040344 A2 | 3/2017 |
| WO | WO-2017087723 A1 | 5/2017 |
| WO | WO-2018027155 A1 | 2/2018 |
| WO | WO-2018121605 A1 | 7/2018 |
| WO | 2019071358 A1 | 4/2019 |
| WO | WO-2020018727 A1 | 1/2020 |

OTHER PUBLICATIONS

Alabanza et al. Function of Novel Anti-CD19 Chimeric Antigen Receptors with Human Variable Regions Is Affected by Hinge and Transmembrane Domains. Mol Ther 25(11):2452-2465 (2017).

Anderson et al. Comodulation of CD3 and CD4. Evidence for a specific association between CD4 and approximately 5% of the CD3:T cell receptor complexes on helper T lymphocytes. J Immunol 140:1732-1737 (1988).

Arcaro et al. Essential role of CD8 palmitoylation in CD8 coreceptor function. J. Immunol. 165:2068-2076 (2000).

Chames et al. Bispecific antibodies for cancer therapy: the light at the end of the tunnel? MAbs 1:539-547 (2009).

Chervin et al. The impact of TCR-binding properties and antigen presentation format on T cell responsiveness. J. Immunol. 183:1166-1178 (2009).

Compte et al. Inhibition of tumor growth in vivo by in situ secretion of bispecific anti-CEA x anti-CD3 diabodies from lentivirally transduced human lymphocytes. Cancer Gene Therapy 14:380-388 (2007).

Deans et al. Interaction of CD4:lck with the T cell receptor/CD3 complex induces early signaling events in the absence of CD45 tyrosine phosphatase. Eur J Immunol 22:661-668 (1992).

Dotti et al. Fifteen years of gene therapy based on chimeric antigen receptors: "are we nearly there yet?" Hum. Gene Ther. 20:1229-1239 (2009).

EP15746948.7 Communication pursuant to Rule 114(2) EPC dated Jan. 21, 2019.

Finney et al. Activation of resting human primary T cells with chimeric receptors: costimulation from CD28, inducible costimulator, CD134, and CD137 in series with signals from the TCR zeta chain. J. Immunol. 172:104-113 (2004).

Fournier et al. Bispecific antibodies and trispecific immunocytokines for targeting the immune system against cancer: preparing for the future. BioDrugs 27:35-53 (2013).

Fragoso et al. Lipid raft distribution of CD4 depends on its palmitoylation and association with Lck, and evidence for CD4-induced lipid raft aggregation as an additional mechanism to enhance CD3 signaling. J. Immunol. 170:913-921 (2003).

Frankel et al. Targeting T cells to tumor cells using bispecific antibodies. Curr Opin Chem Biol 17(3):385-392 (2013).

Fry et al. T-cell adoptive immunotherapy for acute lymphoblastic leukemia. Hematology Am. Soc. Hematol. Educ. Program 2013:348-353 (2013).

Geiger et al. Integrated src kinase and costimulatory activity enhances signal transduction through single-chain chimeric receptors in T lymphocytes. Blood 98(8):2364-2371 (2001).

Geyer et al. Review: Current clinical applications of chimeric antigen receptor (CAR) modified T cells. Cytotherapy 18(11):1393-1409 (2016).

Hammond et al. Selective targeting and potent control of tumor growth using an EphA2/CD3-Bispecific single-chain antibody construct. 67(8):3927-3935 (2007).

Han et al. Chimeric antigen receptor-engineered T cells for cancer immunotherapy: progress and challenges. J. Hematol. Oncol. 6:47 (2013).

He et al. T-cell antigen receptor triggering and lipid rafts: a matter of space and time scales. Talking Point on the involvement of lipid rafts in T-cell activation. EMBO Rep. 9:525-530 (2008).

Helsen et al. The chimeric TAC receptor co-opts the T cell receptor yielding robust anti-tumor activity without toxicity. Nature Communications 9:3049 (2018).

Helsen et al. Tri-functional T cell receptor antigen coupler (Tri-TAC): a novel methodto direct T cells against tumors. J Immunother Cancer 2(Supp3):P17 (2014).

Hexham et al. Optimization of the anti-(human CD3) immunotoxin DT389-scFv(UCHT1) N-terminal sequence to yield a homogeneous protein. Biotechnol Appl Biochem 34(Pt 3):183-187 (2010).

Humphries. Adoptive cell therapy: Honing that killer instinct. Nature 504:S13-15 (2013).

Itano et al. The cytoplasmic domain of CD4 promotes the development of CD4 lineage T cells. J Exp Med. 183(3):731-741 (1996).

Kim et al. A zinc clasp structure tethers Lck to T cell coreceptors CD4 and CD8. Science 301:1725-1728 (2003).

Klinger et al. Harnessing T cells to fight cancer with BiTE® antibody constructs—past developments and future directions. Immunol Rev. 270(1):193-208 (2016).

Kochenderfer et al. Treating B-cell cancer with T cells expressing anti-CD19 chimeric antigen receptors. Nat. Rev. Clin. Oncol. 10:267-276 (2013).

Kuhns et al. TCR Signaling Emerges from the Sum of Many Parts. Front. Immunol. 3:159 (2012).

Löffler et al. A recombinant bispecific single-chain antibody, CD19 X CD3, induces rapid and high lymphoma-directed cytotoxicity by unstimulated T lymphocytes. Blood 95(6):2098-2103 (2000).

Methi et al. Short-interfering RNA-mediated Lck knockdown results in augmented downstream T cell responses. J. Immunol. 175(11):7398-7406 (2005).

Milone et al. Chimeric receptors containing CD137 signal transduction domains mediate enhanced survival of T cells and increased antileukemic efficacy in vivo. Mol. Ther. 17:1453-1464 (2009).

Molhoj, et al. CD19-/CD3-bispecific antibody of the BiTE class is far superior to tandem diabody with respect to redirected tumor cell lysis. Mol Immunol. Mar. 2007;44(8):1935-43. Epub Nov. 2, 2006.

Nagorsen et al. Immunomodulatory therapy of cancer with T cell-engaging BiTE antibody blinatumomab. Exp Cell Res 317(9):1255-1260 (2011).

Nagorsen et al. Immunotherapy of lymphoma and leukemia with T-cell engaging BiTE antibody blinatumomab. Leuk Lymph 50(6):886-891 (2009).

(56) References Cited

OTHER PUBLICATIONS

Panka et al. Variable region framework differences result in decreased or increased affinity of variant anti-digoxin antibodies. PNAS USA 85:3080-3084 (1988).
PCT/CA2015/000068 International Search Report and Written Opinion dated May 4, 2015.
PCT/CA2018/051290 International Search Report and Written Opinion dated Jan. 17, 2019.
PCT/US2019/042297 International Search Report and Written Opinion dated Oct. 30, 2019.
Pilozzi et al. Co-expression of CD79a (JCB117) and CD3 by lymphoblastic lymphoma. J Pathol 186(2):140-143. (1998).
Popik et al. CD4 receptor localized to non-raft membrane microdomains supports HIV-1 entry. Identification of a novel raft localization marker in CD4. J Biol Chem 279(1):704-712 (2004).
Portell et al. Clinical and pharmacologic aspects of blinatumomab in the treatment of B-cell acute lymphoblastic leukemia. Clin. Pharmacol. 5(Suppl 1):5-11 (2013).
Rosenberg et al. Use of tumor-infiltrating lymphocytes and interleukin-2 in the immunotherapy of patients with metastatic melanoma. A preliminary report. NEJM 319:1676 (1988).
Rudikoff et al. Single amino acid substitution altering antigen-binding specificity. PNAS USA 79:1979-1983 (1982).
Thompson et al. Clustal W: improving the sensitivity of progressive multiple sequence alignment through sequence weighting, position-specific gap penalties and weight matrix choice. Nucleic Acid Res. 22:4673-4680 (1994).
Till et al. CD20-specific adoptive immunotherapy for lymphoma using a chimeric antigen receptor with both CD28 and 4-1BB domains: pilot clinical trial results. Blood 119(17):3940-3950 (2012).
U.S. Appl. No. 15/117,173 Office Action dated Jan. 24, 2018.
U.S. Appl. No. 15/117,173 Office Action dated Jun. 21, 2019.
U.S. Appl. No. 15/117,173 Office Action dated Oct. 24, 2018.
U.S. Appl. No. 16/442,274 Office Action dated Nov. 6, 2019.
Velasquez. T cells expressing CD19-specific Engager Molecules for the Immunotherapy of CD19-positive Malignancies. Sci Rep 6:27130 (2016).
Wels et al. Construction, Bacterial Expression and Characterization of a Bifunctional Single-Chain Antibody-Phosphatase Fusion Protein Targeted to the human ERBB-2 receptor. Nature Biotech 10:1128-1132 (1992).
Wittlich et al. Structural characterization of the transmembrane and cytoplasmic domains of human CD4. Biochimica et Biophysica Acta 1768:2949-2960 (2007).
Wykosky et al. The EphA2 receptor and ephrinA1 ligand in solid tumors: function and therapeutic targeting. Mol Cancer Res. 6(12):1795-1806 (2008).
Yin et al. Crystal structure of a complete ternary complex of T-cell receptor, peptide-MHC, and CD4. PNAS USA 109:5405-5410 (2012).
Zahnd et al. Efficient Tumor Targeting with High-Affinity Designed Ankyrin Repeat Proteins: Effects of Affinity and Molecular Size. Cancer Res 70:1595-1605 (2010).
Zahnd et al. Selection and Characterization of Her2 Binding-designed Ankyrin Repeat Proteins. The Journal of Biological Chemistry 281(46):35167-35175 (2006).
Zhang et al. Sequestration of CD4-associated Lck from the TCR complex may elicit T cell hyporesponsiveness in nonobese diabetic mice. J Immunol 160:1148-1157 (1998).
Zhukovsky et al. Bispecific antibodies and CARs: generalized immunotherapeutics harnessing T cell redirection. Curr Opin Immunol 40:24-35 (2016).
PCT/CA2015/000068 International Preliminary Report on Patentability dated Aug. 9, 2016.
Apuri, S., et al., "Outcomes in Patients with Acute Myeloid Leukemia Preceded by Breast Cancer", Blood, 120(21): 4316 (2012).
Carpenter, R.O., et al., B-cell maturation antigen is a promising target for adoptive T-cell therapy of multiple myeloma, Clin Cancer Res, 19(8): 2048-2060 (2013).
Chiu, A., et al., Hodgkin lymphoma cells express TACI and BCMA receptors and generate survival and proliferation signals in response to BAFF and APRIL, Blood, 109(2): 729-739 (2007).
De Novo, New Products from R&D Systems, Antibody catalog including BCMA mAB, pp. 1-10 (Mar. 2004).
Deng, S., et al., B-lymphocyte-induced maturation protein 1 up-regulates the expression of B-cell maturation antigen in mouse plasma cells, Mol Biol Rep, 37(8): 3747-3755 (2010).
Deshayes, S., et al., Cell-penetrating peptides: tools for intracellular delivery of therapeutics, Cell Mol Life Sci, 62(16): 1839-1849 (2005).
Guadagnoli, M., et al., Development and characterization of APRIL antagonistic monoclonal antibodies for treatment of B-cell lymphomas, Blood, 117(25): 6856-6865 (2011).
Jamal, S., et al., "Immunophenotypic Analysis of Peripheral T-Cell Neoplasms", Am. J. Clin. Pathol., vol. 116, pp. 512-526, (2001).
Kiewe, P., et al., "Phase I Trial of the Trifunctional Anti-HER2 x Anti-CD3 Antibody Ertumaxomab in Matastatic Breast Cancer", Clin. Cancer Res., 12(10), pp. 3085-3091, (2006).
Kimchi-Sarfaty, C., et al., "A 'silent' polymorphiosm in the MDR1 gene changes substrate specificity", Science, 315:525-528, (2007).
Marsden, H.R., et al., Model systems for membrane fusion, Chem Soc Rev, 40(3): 1572-1585 (2011).
Novak, A.J., et al., Expression of BLyS and its receptors in B-cell non-Hodgkin lymphoma: correlation with disease activity and patient outcome, Blood, 104(8): 2247-2253 (2004).
Ryan, M.C., et al., Antibody targeting of B-cell maturation antigen on malignant plasma cells, Mol Cancer Ther, 6(11): 3009-3018 (2007).
Tai, Y-T., et al., Novel Fc-Engineered Anti-B Cell Maturation Antigen-Monomethyl Auristatin F Antibody-Drug Conjugate (GSK2857916) Induces Potent and Selective Anti-Multiple Myeloma Activity via Enhanced Effector Function and Direct Tumor Cell Killing, Blood, 122(21): 877 (2013).
U.S. Appl. No. 15/929,510 Office Action dated Nov. 9, 2020.
U.S. Appl. No. 15/929,513 Office Action dated May 11, 2021.
U.S. Appl. No. 15/929,513 Office Action dated Nov. 30, 2020.
U.S. Appl. No. 16/547,421 Office Action dated Nov. 24, 2021.
U.S. Appl. No. 16/904,451 Office Action dated Dec. 1, 2020.
U.S. Appl. No. 16/904,451 Office Action dated May 10, 2021.
U.S. Appl. No. 17/248,174 Office Action dated Mar. 11, 2021.
U.S. Appl. No. 17/304,924 Application filed Jun. 28, 2021.
U.S. Appl. No. 17/394,280 Office Action dated Dec. 10, 2021.
Voet, D., et. al., Biochemistry, John Wiley and Sons, New York, pp. 126-128, (1990).
Wang, M., et al., Efficient delivery of genome-editing proteins using bioreducible lipid nanoparticles, PNAS, 113(11): 2868-2873 (2016).
Yong, K. L., et al., Evaluation of Bcma as a Therapeutic Target in Multiple Myeloma Using an Antibody-Drug Conjugate, Blood, 122(21): 4447 (2013).

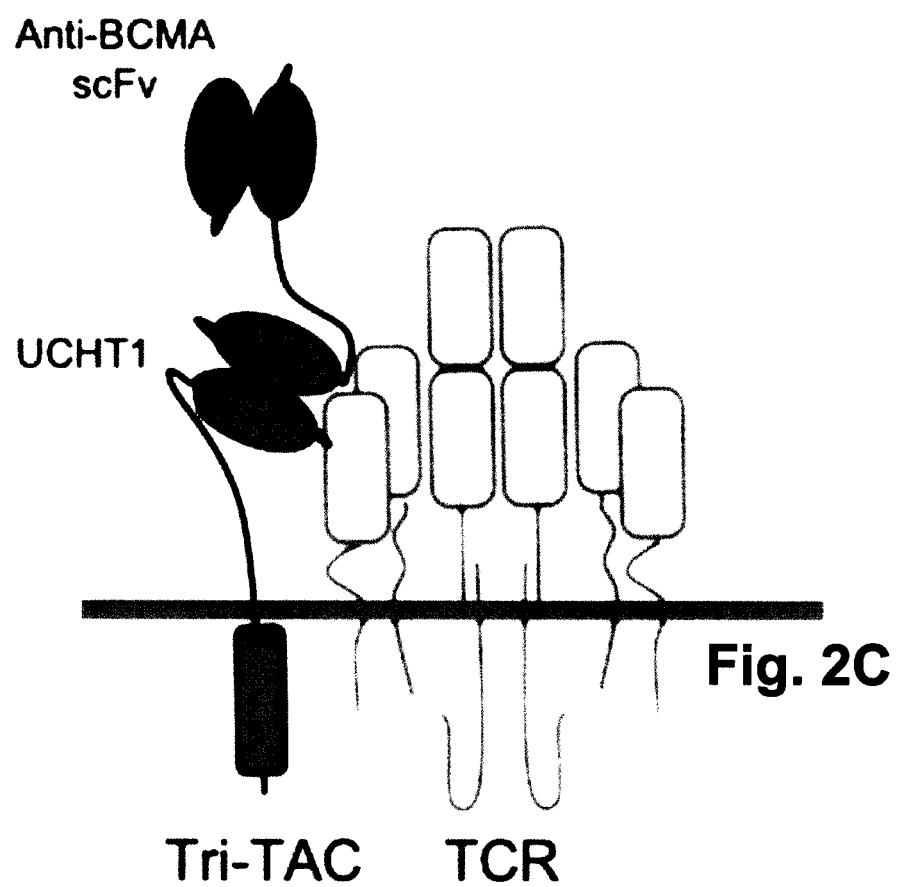

A

```
                          1                                                  50
      UCHT1       (1)   MDIQMTQTTSSLSASLGDRVTISCRASQDIRNYLNWYQQKPDGTVKLLIY
      UCHT1 Y182T (1)   MDIQMTQTTSSLSASLGDRVTISCRASQDIRNYLNWYQQKPDGTVKLLIY
                          51                                                 100
      UCHT1       (51)  YTSRLHSGVPSKFSGSGSGTDYSLTISNLEQEDIATYFCQQGNTLPWTFA
      UCHT1 Y182T (51)  YTSRLHSGVPSKFSGSGSGTDYSLTISNLEQEDIATYFCQQGNTLPWTFA
                          101                                                150
      UCHT1       (101) GGTKLEIKGGGSGGGGSGGGGSGGGGSEVQLQQSGPELVKPGASMKISC
      UCHT1 Y182T (101) GGTKLEIKGGGSGGGGSGGGGSGGGGSEVQLQQSGPELVKPGASMKISC
                          151              182                               200
      UCHT1       (151) KASGYSFTGYTMNWVKQSHGKNLEWMGLINPYKGVSTYNQKFKDKATLTV
      UCHT1 Y182T (151) KASGYSFTGYTMNWVKQSHGKNLEWMGLINPTKGVSTYNQKFKDKATLTV
                          201                                                250
      UCHT1       (201) DKSSSTAYMELLSLTSEDSAVYYCARSGYYGDSDWYFDVWGQGTTLTVFS
      UCHT1 Y182T (201) DKSSSTAYMELLSLTSEDSAVYYCARSGYYGDSDWYFDVWGQGTTLTVFS
```

B

```
                          1                                                  50
      UCHT1       (1)   MDIQMTQTTSSLSASLGDRVTISCRASQDIRNYLNWYQQKPDGTVKLLIY
      huUCHT1     (1)   MDIQMTQSPSSLSASVGDRVTITCRASQDIRNYLNWYQQKPGKAPKLLIY
                          51                                                 100
      UCHT1       (51)  YTSRLHSGVPSKFSGSGSGTDYSLTISNLEQEDIATYFCQQGNTLPWTFA
      huUCHT1     (51)  YTSRLESGVPSRFSGSGSGTDYTLTISSLQPEDFATYYCQQGNTLPWTFG
                          101                                                150
      UCHT1       (101) GGTKLEIKGGGSGGGGSGGGGSGGGGSEVQLQQSGPELVKPGASMKISC
      huUCHT1     (101) QGTKVEIKGGGSGGGGSGGGGS-----EVQLVESGGGLVQPGGSLRLSC
                          151                                                200
      UCHT1       (151) KASGYSFTGYTMNWVKQSHGKNLEWMGLINPYKGVSTYNQKFKDKATLTV
      huUCHT1     (146) AASGYSFTGYTMNWVRQAPGKGLEWVALINPYKGVSTYNQKFKDRFTISV
                          201                                                250
      UCHT1       (201) DKSSSTAYMELLSLTSEDSAVYYCARSGYYGDSDWYFDVWGQGTTLTVFS
      huUCHT1     (196) DKSKNTAYLQMNSLRAEDTAVYYCARSGYYGDSDWYFDVWGQGTLVTVSS
```

C

```
                          1                                                  50
      huUCHT1      (1)   MDIQMTQSPSSLSASVGDRVTITCRASQDIRNYLNWYQQKPGKAPKLLIY
      huUCHT1 Y177T(1)   MDIQMTQSPSSLSASVGDRVTITCRASQDIRNYLNWYQQKPGKAPKLLIY
                          51                                                 100
      huUCHT1      (51)  YTSRLESGVPSRFSGSGSGTDYTLTISSLQPEDFATYYCQQGNTLPWTFG
      huUCHT1 Y177T(51)  YTSRLESGVPSRFSGSGSGTDYTLTISSLQPEDFATYYCQQGNTLPWTFG
                          101                                                150
      huUCHT1      (101) QGTKVEIKGGGSGGGGSGGGGSEVQLVESGGGLVQPGGSLRLSCAASGY
      huUCHT1 Y177T(101) QGTKVEIKGGGSGGGGSGGGGSEVQLVESGGGLVQPGGSLRLSCAASGY
                          151           177                                  200
      huUCHT1      (151) SFTGYTMNWVRQAPGKGLEWVALINPYKGVSTYNQKFKDRFTISVDKSKN
      huUCHT1 Y177T(151) SFTGYTMNWVRQAPGKGLEWVALINPTKGVSTYNQKFKDRFTISVDKSKN
                          201                                          245
      huUCHT1      (201) TAYLQMNSLRAEDTAVYYCARSGYYGDSDWYFDVWGQGTLVTVSS
      huUCHT1 Y177T(201) TAYLQMNSLRAEDTAVYYCARSGYYGDSDWYFDVWGQGTLVTVSS
```

Fig. 11

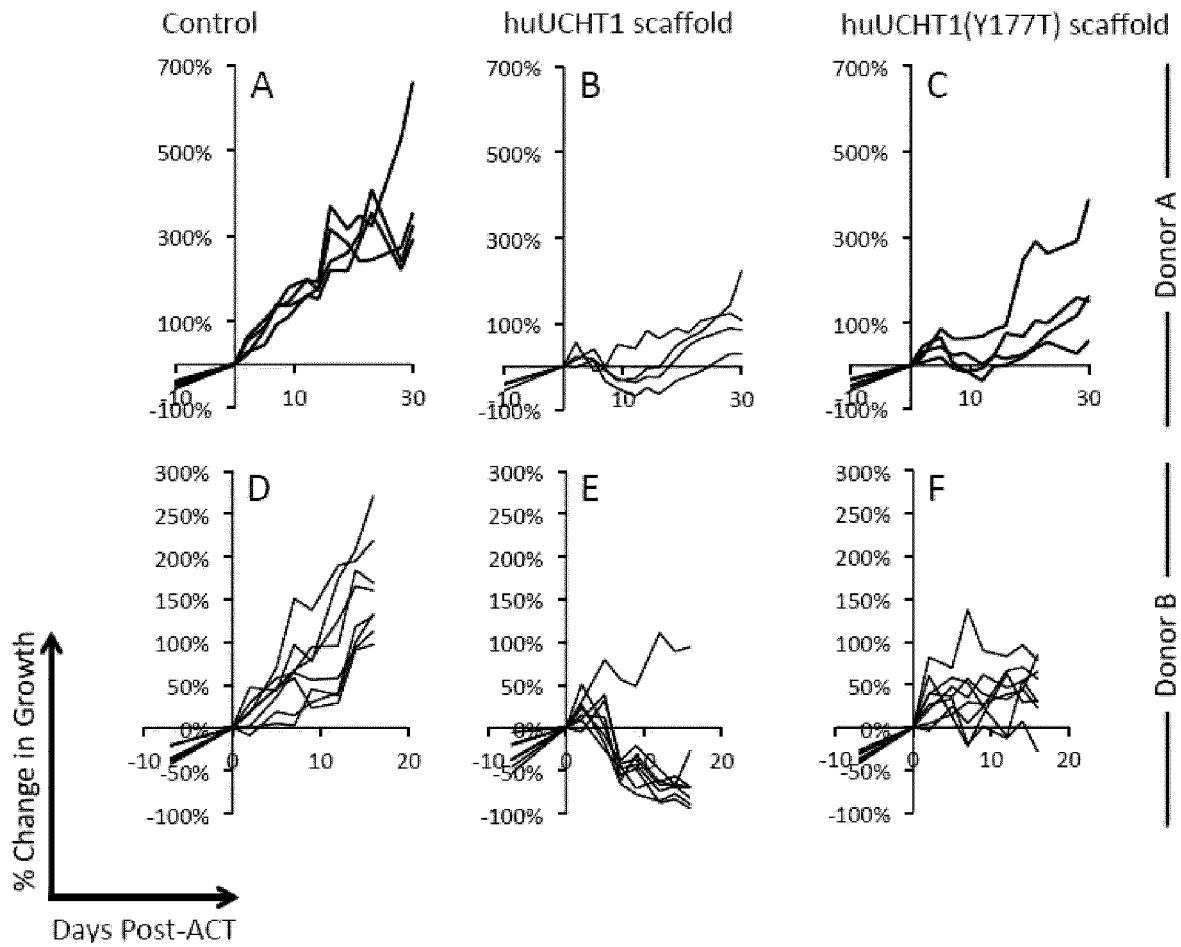

Fig. 17

SEQ ID NO: 31
huUCHT1
atggatatccagatgacccagtccccgagctccctgtccgcctctgtgggcgatagggtcaccatcacctgccgtgccagt
caggacatccgtaattatctgaactggtatcaacagaaaccaggaaaagctccgaaactactgatttactatacctcccgc
ctggagtctggagtcccttctcgcttctctggttctggttctgggacggattacactctgaccatcagcagtctgcaaccggaa
gacttcgcaacttattactgtcagcaaggtaatactctgccgtggacgttcggacagggcaccaaggtggagatcaaagg
cggcggcggaagtggaggaggaggctcaggcggaggagggagcgaggttcagctggtggagtctggcggtggcctg
gtgcagccaggggggctcactccgtttgtcctgtgcagcttctggctactcctttaccggctacactatgaactgggtgcgtcag
gccccaggtaagggcctggaatgggttgcactgattaatccttataaaggtgttagtacctacaaccagaagttcaaggac
cgtttcactataagcgtagataaatccaaaaacacagcctacctgcaaatgaacagcctgcgtgctgaggacactgccgt
ctattattgtgctagaagcggatactacggcgatagtgactggtattttgacgtgtggggtcaaggaaccctggtcaccgtct
cctcg

Fig. 18

SEQUENCE LISTING

```
<160> NUMBER OF SEQ ID NOS: 30

<210> SEQ ID NO 1
<211> LENGTH: 1575
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
atggatttcc aggtccagat tttctccttc ctgctgattt ccgcaagcgt cattatgtca        60
cggggctccg acctgggcaa aaagctgctg gaggccgcta gggccgggca ggacgatgaa       120
gtgagaatcc tgatggccaa cggggctgac gtgaatgcta aggatgagta cggcctgacc       180
cccctgtatc tggctacagc acacggccat ctggagatcg tggaagtcct gctgaaaaac       240
ggagccgacg tgaatgcagt cgatgccatt gggttcactc ctctgcacct ggcagccttt       300
atcggacatc tggagattgc agaagtgctg ctgaagcacg gcgctgacgt gaacgcacag       360
gataagttcg gaaaaaccgc ttttgacatc agcattggca acggaaatga agacctggct       420
gaaatcctgc agaaactgaa tgaacagaaa ctgattagca agaagacct gaaccccggg       480 ggaggaggag ggagcggggg aggaggcagc ggcggggag gctctggagg aggagggagc       540
ggatccatgg acatccagat gactcagacc acaagctccc tgtctgcaag tctgggcgac       600
cgggtgacaa tctcctgcag agcctctcag gatattagga actacctgaa ttggtatcag       660
cagaaacctg atggcacagt caagctgctg atctactata ccagccggct gcactcaggc       720
gtgccaagca aattctcagg aagcggctcc gggactgact actccctgac catctctaac       780
ctggagcagg aagatattgc tacctatttc tgccagcagg gcaatacact gccctggact       840
tttgccggag gcaccaaact ggagatcaag gggggaggcg ggagtggagg cggggatca       900 ggaggaggag gcagcggagg aggagggtcc gaggtccagc tgcagcagag cggaccagaa       960
ctggtgaagc ccggagcaag tatgaaaatc tcctgtaagg cctcaggata cagcttcacc      1020
ggctatacaa tgaactgggt gaaacagtcc catggcaaga acctggaatg gatggggctg      1080
attaatcctt acaaaggcgt cagcacctat aatcagaagt ttaaagacaa ggccacactg      1140
actgtggata gtctagttc aaccgcttac atggagctgc tgtccctgac atctgaagac      1200
agtgccgtgt actattgtgc tcggtctggc tactatgggg acagtgattg gtacttcgat      1260
gtctggggac agggcactac cctgaccgtg ttttctacta gtggcggagg aggatcactc      1320
gagagcggac aggtgctgct ggaatccaat atcaaagtcc tgcccacttg gtctacccc      1380 gtgcagccta tggctctgat tgtgctggga ggagtcgcag gactgctgct gtttatcggg      1440
```

```
ctgggaattt tcttttgcgt gcgctgccgg caccggagaa ggcaggccga gcgcatgagc    1500
cagatcaagc gactgctgag cgagaagaaa acctgtcagt gtccccatag attccagaag    1560
acctgttcac ccatt                                                     1575
```

<210> SEQ ID NO 2
<211> LENGTH: 525
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 2

```
Met Asp Phe Gln Val Gln Ile Phe Ser Phe Leu Leu Ile Ser Ala Ser
1               5                   10                  15

Val Ile Met Ser Arg Gly Ser Asp Leu Gly Lys Lys Leu Leu Glu Ala
            20                  25                  30

Ala Arg Ala Gly Gln Asp Asp Glu Val Arg Ile Leu Met Ala Asn Gly
        35                  40                  45

Ala Asp Val Asn Ala Lys Asp Glu Tyr Gly Leu Thr Pro Leu Tyr Leu
    50                  55                  60

Ala Thr Ala His Gly His Leu Glu Ile Val Glu Val Leu Leu Lys Asn
65                  70                  75                  80

Gly Ala Asp Val Asn Ala Val Asp Ala Ile Gly Phe Thr Pro Leu His
                85                  90                  95

Leu Ala Ala Phe Ile Gly His Leu Glu Ile Ala Glu Val Leu Leu Lys
            100                 105                 110

His Gly Ala Asp Val Asn Ala Gln Asp Lys Phe Gly Lys Thr Ala Phe
        115                 120                 125

Asp Ile Ser Ile Gly Asn Gly Asn Glu Asp Leu Ala Glu Ile Leu Gln
    130                 135                 140

Lys Leu Asn Glu Gln Lys Leu Ile Ser Glu Glu Asp Leu Asn Pro Gly
145                 150                 155                 160

Gly Gly Gly Gly Ser Gly Gly Gly Ser Gly Gly Gly Gly Ser Gly
                165                 170                 175

Gly Gly Gly Ser Gly Ser Met Asp Ile Gln Met Thr Gln Thr Thr Ser
            180                 185                 190

Ser Leu Ser Ala Ser Leu Gly Asp Arg Val Thr Ile Ser Cys Arg Ala
        195                 200                 205

Ser Gln Asp Ile Arg Asn Tyr Leu Asn Trp Tyr Gln Gln Lys Pro Asp
    210                 215                 220

Gly Thr Val Lys Leu Leu Ile Tyr Tyr Thr Ser Arg Leu His Ser Gly
225                 230                 235                 240

Val Pro Ser Lys Phe Ser Gly Ser Gly Ser Gly Thr Asp Tyr Ser Leu
                245                 250                 255

Thr Ile Ser Asn Leu Glu Gln Glu Asp Ile Ala Thr Tyr Phe Cys Gln
            260                 265                 270

Gln Gly Asn Thr Leu Pro Trp Thr Phe Ala Gly Gly Thr Lys Leu Glu
        275                 280                 285

Ile Lys Gly Gly Gly Gly Ser Gly Gly Gly Gly Ser Gly Gly Gly Gly
    290                 295                 300

Ser Gly Gly Gly Gly Ser Glu Val Gln Leu Gln Gln Ser Gly Pro Glu
305                 310                 315                 320

Leu Val Lys Pro Gly Ala Ser Met Lys Ile Ser Cys Lys Ala Ser Gly
```

```
                325                 330                 335
Tyr Ser Phe Thr Gly Tyr Thr Met Asn Trp Val Lys Gln Ser His Gly
            340                 345                 350
Lys Asn Leu Glu Trp Met Gly Leu Ile Asn Pro Tyr Lys Gly Val Ser
            355                 360                 365
Thr Tyr Asn Gln Lys Phe Lys Asp Lys Ala Thr Leu Thr Val Asp Lys
        370                 375                 380
Ser Ser Ser Thr Ala Tyr Met Glu Leu Leu Ser Leu Thr Ser Glu Asp
385                 390                 395                 400
Ser Ala Val Tyr Tyr Cys Ala Arg Ser Gly Tyr Tyr Gly Asp Ser Asp
                405                 410                 415
Trp Tyr Phe Asp Val Trp Gly Gln Gly Thr Thr Leu Thr Val Phe Ser
            420                 425                 430
Thr Ser Gly Gly Gly Gly Ser Leu Glu Ser Gly Gln Val Leu Leu Glu
            435                 440                 445
Ser Asn Ile Lys Val Leu Pro Thr Trp Ser Thr Pro Val Gln Pro Met
450                 455                 460
Ala Leu Ile Val Leu Gly Gly Val Ala Gly Leu Leu Phe Ile Gly
465                 470                 475                 480
Leu Gly Ile Phe Phe Cys Val Arg Cys Arg His Arg Arg Gln Ala
                485                 490                 495
Glu Arg Met Ser Gln Ile Lys Arg Leu Leu Ser Glu Lys Lys Thr Cys
            500                 505                 510
Gln Cys Pro His Arg Phe Gln Lys Thr Cys Ser Pro Ile
            515                 520                 525

<210> SEQ ID NO 3
<211> LENGTH: 1647
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
atggactttc aggtgcagat tttctctttt ctgctgattt ccgcaagcgt catcgagctc      60 ggggggggggg ggtcaggatc catggacatc cagatgactc agaccacaag ctccctgagc    120
gcatccctgg gcgaccgagt gacaatctca tgcagagcca gccaggatat taggaactac    180
ctgaattggt atcagcagaa acctgacggc acagtcaagc tgctgatcta ctatacttcc    240
cggctgcact ctggcgtgcc aagtaaattc tctggagtg gatcaggcac tgactactca    300
ctgaccatca gcaacctgga gcaggaagat attgctacct atttctgcca gcagggcaat    360
acactgccct ggactttgc aggcgggacc aaactggaga tcaagggcgg cggcggaagt    420
ggaggaggag gctcaggcgg aggagggagc ggcggaggag gcagcgaggt ccagctgcag    480
cagagcggac agaactggt gaagcctggc gcatccatga aaatctcttg taaggcctct    540
gggtacagtt tcaccggata caatgaactg ggtgaaacag tctcatgg caagaacctg     600 gaatggatgg gcctgattaa tccttacaaa ggcgtcagca cctataatca gaagtttaaa    660
gacaaggcca cactgactgt ggataagtct agttcaaccg cttacatgga gctgctgtca    720
ctgacaagcg aagactccgc cgtgtactat tgcgctagga gcggatacta tggcgactcc    780
gattggtact cgatgtctg ggggcaggga actaccctga ccgtgtttag cactagtgga    840
ggaggaggct ctggaggagg aggagtggga ggcggggggat caggaggagg aggcagcgat    900
```

-continued

```
atcatgtcac ggggctccga cctgggcaaa aagctgctgg aggccgctag ggccgggcag      960
gacgatgaag tgagaatcct gatggccaac ggggctgacg tgaatgctaa ggatgagtac     1020
ggcctgaccc ccctgtatct ggctacagca cacggccatc tggagatcgt ggaagtcctg     1080
ctgaaaaacg gagccgacgt gaatgcagtc gatgccattg ggttcactcc tctgcacctg     1140
gcagccttta tcggacatct ggagattgca gaagtgctgc tgaagcacgg cgctgacgtg     1200
aacgcacagg ataagttcgg aaaaaccgct tttgacatca gcattggcaa cggaaatgaa     1260
gacctggctg aaatcctgca gaaactgaat gaacagaaac tgattagcga agaagacctg     1320
aacgtcgacg gaggaggagg gtctggagga ggggaagtg gcgggggagg cagcggggga      1380
ggcgggtctc tcgagagtgg ccaggtgctg ctggaaagca atatcaaggt cctgccaact     1440
tggtccaccc cagtgcagcc tatggctctg attgtgctgg gaggagtcgc aggactgctg     1500
ctgtttatcg gcctggggat tttcttttgc gtgcgctgcc ggcaccggag aaggcaggct     1560
gagcgcatgt ctcagattaa gcgactgctg agcgagaaga gacctgtca gtgccccat      1620
agattccaga aaacctgttc acccatt                                          1647
```

<210> SEQ ID NO 4
<211> LENGTH: 547
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 4

```
Met Asp Phe Gln Val Gln Ile Phe Ser Phe Leu Leu Ile Ser Ala Ser
1               5                   10                  15

Val Ile Glu Leu Gly Gly Gly Ser Gly Ser Met Asp Ile Gln Met
        20                  25                  30

Thr Gln Thr Thr Ser Ser Leu Ser Ala Ser Leu Gly Asp Arg Val Thr
        35                  40                  45

Ile Ser Cys Arg Ala Ser Gln Asp Ile Arg Asn Tyr Leu Asn Trp Tyr
    50                  55                  60

Gln Gln Lys Pro Asp Gly Thr Val Lys Leu Leu Ile Tyr Tyr Thr Ser
65                  70                  75                  80

Arg Leu His Ser Gly Val Pro Ser Lys Phe Ser Gly Ser Gly Ser Gly
                85                  90                  95

Thr Asp Tyr Ser Leu Thr Ile Ser Asn Leu Glu Gln Glu Asp Ile Ala
            100                 105                 110

Thr Tyr Phe Cys Gln Asn Thr Leu Pro Trp Thr Phe Ala Gly Gly Thr
        115                 120                 125

Lys Leu Glu Ile Lys Gly Gly Gly Ser Gly Gly Gly Gly Ser Gly
    130                 135                 140

Gly Gly Ser Gly Gly Gly Gly Ser Glu Val Gln Leu Gln Gln Ser
145                 150                 155                 160

Gly Pro Glu Leu Val Lys Pro Gly Ala Ser Met Lys Ile Ser Cys Lys
                165                 170                 175

Ala Ser Gly Tyr Ser Phe Thr Gly Tyr Thr Met Asn Trp Val Lys Gln
            180                 185                 190

Ser His Gly Lys Asn Leu Glu Trp Met Gly Leu Ile Asn Pro Tyr Lys
        195                 200                 205

Gly Val Ser Thr Tyr Asn Gln Lys Phe Lys Asp Lys Ala Thr Leu Thr
    210                 215                 220
```

Val Asp Lys Ser Ser Ser Thr Ala Tyr Met Glu Leu Leu Ser Leu Thr
225                 230                 235                 240

Ser Glu Asp Ser Ala Val Tyr Tyr Cys Ala Arg Ser Gly Tyr Tyr Gly
            245                 250                 255

Asp Ser Asp Trp Tyr Phe Asp Val Trp Gly Gln Gly Thr Thr Leu Thr
                260                 265                 270

Val Phe Ser Thr Ser Gly Gly Gly Gly Ser Gly Gly Gly Gly Ser Gly
        275                 280                 285

Gly Gly Gly Ser Gly Gly Gly Gly Ser Asp Ile Met Ser Arg Gly Ser
        290                 295                 300

Asp Leu Gly Lys Lys Leu Leu Glu Ala Ala Arg Ala Gly Gln Asp Asp
305                 310                 315                 320

Glu Val Arg Ile Leu Met Ala Asn Gly Ala Asp Val Asn Ala Lys Asp
                325                 330                 335

Glu Tyr Gly Leu Thr Pro Leu Tyr Leu Ala Thr Ala His Gly His Leu
                340                 345                 350

Glu Ile Val Glu Val Leu Leu Lys Asn Gly Ala Asp Val Asn Ala Val
            355                 360                 365

Asp Ala Ile Gly Phe Thr Pro Leu His Leu Ala Ala Phe Ile Gly His
370                 375                 380

Leu Glu Ile Ala Glu Val Leu Leu Lys His Gly Ala Asp Val Asn Ala
385                 390                 395                 400

Gln Asp Lys Phe Gly Lys Thr Ala Phe Asp Ile Ser Ile Gly Asn Gly
                405                 410                 415

Asn Glu Asp Leu Ala Glu Ile Leu Gln Lys Leu Asn Glu Gln Lys Leu
            420                 425                 430

Ile Ser Glu Glu Asp Leu Asn Val Asp Gly Gly Gly Ser Gly Gly Gly
        435                 440                 445

Gly Gly Ser Gly Gly Gly Gly Ser Gly Gly Gly Gly Ser Leu Glu Ser
        450                 455                 460

Gly Gln Val Leu Leu Glu Ser Asn Ile Lys Val Leu Pro Thr Trp Ser
465                 470                 475                 480

Thr Pro Val Gln Pro Met Ala Leu Ile Val Leu Gly Gly Val Ala Gly
                485                 490                 495

Leu Leu Leu Phe Ile Gly Leu Gly Ile Phe Phe Cys Val Arg Cys Arg
                500                 505                 510

His Arg Arg Arg Gln Ala Glu Arg Met Ser Gln Ile Lys Arg Leu Leu
            515                 520                 525

Ser Glu Lys Lys Thr Cys Gln Cys Pro His Arg Phe Gln Lys Thr Cys
530                 535                 540

Ser Pro Ile
545

<210> SEQ ID NO 5
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
atggatttcc aggtccagat tttctccttc ctgctgattt ccgcaagcgt catt        54

<210> SEQ ID NO 6
<211> LENGTH: 18

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Met Asp Phe Gln Val Gln Ile Phe Ser Phe Leu Leu Ile Ser Ala Ser
1               5                   10                  15

Val Ile

<210> SEQ ID NO 7
<211> LENGTH: 387
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
atgtcacggg gctccgacct gggcaaaaag ctgctggagg ccgctagggc cgggcaggac      60
gatgaagtga gaatcctgat ggccaacggg gctgacgtga atgctaagga tgagtacggc     120 ctgaccccc tgtatctggc tacagcacac ggccatctgg agatcgtgga agtcctgctg     180
aaaaacggag ccgacgtgaa tgcagtcgat gccattgggt tcactcctct gcacctggca     240
gcctttatcg gacatctgga gattgcagaa gtgctgctga agcacggcgc tgacgtgaac     300
gcacaggata agttcggaaa aaccgctttt gacatcagca ttggcaacgg aaatgaagac     360
ctggctgaaa tcctgcagaa actgaat                                         387

<210> SEQ ID NO 8
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Ser Arg Gly Ser Asp Leu Gly Lys Lys Leu Leu Glu Ala Ala Arg
1               5                   10                  15

Ala Gly Gln Asp Asp Glu Val Arg Ile Leu Met Ala Asn Gly Ala Asp
            20                  25                  30

Val Asn Ala Lys Asp Glu Tyr Gly Leu Thr Pro Leu Tyr Leu Ala Thr
        35                  40                  45

Ala His Gly His Leu Glu Ile Val Glu Val Leu Leu Lys Asn Gly Ala
    50                  55                  60

Asp Val Asn Ala Val Asp Ala Ile Gly Phe Thr Pro Leu His Leu Ala
65                  70                  75                  80

Ala Phe Ile Gly His Leu Glu Ile Ala Glu Val Leu Leu Lys His Gly
                85                  90                  95

Ala Asp Val Asn Ala Gln Asp Lys Phe Gly Lys Thr Ala Phe Asp Ile
            100                 105                 110

Ser Ile Gly Asn Gly Asn Glu Asp Leu Ala Glu Ile Leu Gln Lys Leu
        115                 120                 125

Asn

<210> SEQ ID NO 9
<211> LENGTH: 30
<212> TYPE: DNA

-continued

<213> ORGANISM: Artificial Sequence
<220> FEATURE:
<223> OTHER INFORMATION: Description of Artificial Sequence: Synthetic
      oligonucleotide

<400> SEQUENCE: 9
gaacagaaac tgattagcga agaagacctg                                          30

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Glu Gln Lys Leu Ile Ser Glu Glu Asp Leu
1               5                   10

<210> SEQ ID NO 11
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
aaccccgggg gaggaggagg gagcggggga ggaggcagcg gcggggagg ctctggagga          60 ggagggagcg gatcc                                                          75

<210> SEQ ID NO 12
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asn Pro Gly Gly Gly Gly Gly Ser Gly Gly Gly Gly Ser Gly Gly Gly
1               5                   10                  15

Gly Ser Gly Gly Gly Gly Ser Gly Ser
            20                  25

<210> SEQ ID NO 13
<211> LENGTH: 750
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
atggacatcc agatgactca gaccacaagc tccctgtctg caagtctggg cgaccgggtg         60
acaatctcct gcagagcctc tcaggatatt aggaactacc tgaattggta tcagcagaaa        120
cctgatggca cagtcaagct gctgatctac tataccagcc ggctgcactc aggcgtgcca        180
agcaaattct caggaagcgg ctccgggact gactactccc tgaccatctc taacctggag        240
caggaagata ttgctaccta tttctgccag caggcaata cactgccctg gacttttgcc         300
ggaggcacca aactggagat caaggggggga ggcgggagtg gaggcggggg atcaggagga        360
ggaggcagcg gaggaggagg gtccgaggtc cagctgcagc agagcggacc agaactggtg        420

```
aagcccggag caagtatgaa aatctcctgt aaggcctcag gatacagctt caccggctat    480
acaatgaact gggtgaaaca gtcccatggc aagaacctgg aatggatggg gctgattaat    540
ccttacaaag gcgtcagcac ctataatcag aagtttaaag acaaggccac actgactgtg    600
gataagtcta gttcaaccgc ttacatggag ctgctgtccc tgacatctga agacagtgcc    660
gtgtactatt gtgctcggtc tggctactat ggggacagtg attggtactt cgatgtctgg    720
ggacagggca ctaccctgac cgtgttttct                                     750
```

```
<210> SEQ ID NO 14
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14
```

```
Met Asp Ile Gln Met Thr Gln Thr Thr Ser Ser Leu Ser Ala Ser Leu
1               5                   10                  15

Gly Asp Arg Val Thr Ile Ser Cys Arg Ala Ser Gln Asp Ile Arg Asn
            20                  25                  30

Tyr Leu Asn Trp Tyr Gln Gln Lys Pro Asp Gly Thr Val Lys Leu Leu
        35                  40                  45

Ile Tyr Tyr Thr Ser Arg Leu His Ser Gly Val Pro Ser Lys Phe Ser
    50                  55                  60

Gly Ser Gly Ser Gly Thr Asp Tyr Ser Leu Thr Ile Ser Asn Leu Glu
65                  70                  75                  80

Gln Glu Asp Ile Ala Thr Tyr Phe Cys Gln Gln Gly Asn Thr Leu Pro
                85                  90                  95

Trp Thr Phe Ala Gly Gly Thr Lys Leu Glu Ile Lys Gly Gly Gly Gly
            100                 105                 110

Ser Gly Gly Gly Gly Ser Gly Gly Gly Ser Gly Gly Gly Gly Ser
        115                 120                 125

Glu Val Gln Leu Gln Gln Ser Gly Pro Glu Leu Val Lys Pro Gly Ala
    130                 135                 140

Ser Met Lys Ile Ser Cys Lys Ala Ser Gly Tyr Ser Phe Thr Gly Tyr
145                 150                 155                 160

Thr Met Asn Trp Val Lys Gln Ser His Gly Lys Asn Leu Glu Trp Met
                165                 170                 175

Gly Leu Ile Asn Pro Tyr Lys Gly Val Ser Thr Tyr Asn Gln Lys Phe
            180                 185                 190

Lys Asp Lys Ala Thr Leu Thr Val Asp Lys Ser Ser Ser Thr Ala Tyr
        195                 200                 205

Met Glu Leu Leu Ser Leu Thr Ser Glu Asp Ser Ala Val Tyr Tyr Cys
    210                 215                 220

Ala Arg Ser Gly Tyr Tyr Gly Asp Ser Asp Trp Tyr Phe Asp Val Trp
225                 230                 235                 240

Gly Gln Gly Thr Thr Leu Thr Val Phe Ser
                245                 250
```

```
<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 15
actagtggcg gaggaggatc actcgag                                              27

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Thr Ser Gly Gly Gly Gly Ser Leu Glu
1               5

<210> SEQ ID NO 17
<211> LENGTH: 252
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
agcggacagg tgctgctgga atccaatatc aaagtcctgc ccacttggtc taccccgtg         60 cagcctatgg ctctgattgt gctgggagga gtcgcaggac tgctgctgtt tatcgggctg      120
ggaattttct tttgcgtgcg ctgccggcac cggagaaggc aggccgagcg catgagccag      180
atcaagcgac tgctgagcga aagaaaaacc tgtcagtgtc cccatagatt ccagaagacc      240
tgttcaccca tt                                                          252

<210> SEQ ID NO 18
<211> LENGTH: 84
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Ser Gly Gln Val Leu Leu Glu Ser Asn Ile Lys Val Leu Pro Thr Trp
1               5                   10                  15

Ser Thr Pro Val Gln Pro Met Ala Leu Ile Val Leu Gly Gly Val Ala
            20                  25                  30

Gly Leu Leu Leu Phe Ile Gly Leu Gly Ile Phe Phe Cys Val Arg Cys
        35                  40                  45

Arg His Arg Arg Arg Gln Ala Glu Arg Met Ser Gln Ile Lys Arg Leu
    50                  55                  60

Leu Ser Glu Lys Lys Thr Cys Gln Cys Pro His Arg Phe Gln Lys Thr
65                  70                  75                  80

Cys Ser Pro Ile

<210> SEQ ID NO 19
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19

```
agcggacagg tgctgctgga atccaatatc aaagtcctgc ccacttggtc tacccccgtg    60
cagcct                                                                66
```

<210> SEQ ID NO 20
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

```
Ser Gly Gln Val Leu Leu Glu Ser Asn Ile Lys Val Leu Pro Thr Trp
1               5                   10                  15

Ser Thr Pro Val Gln Pro
            20
```

<210> SEQ ID NO 21
<211> LENGTH: 801
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21

```
atggattttc aggtgcagat tttcagcttc ctgctaatca gtgcctcagt cataatgtct    60
agagacatcg tgctgaccca gagcccccc agcctggcca tgtctctggg caagagagcc   120
accatcagct gccgggccag cgagagcgtg accatcctgg gcagccacct gatccactgg   180
tatcagcaga gcccggcca gccccccacc ctgctgatcc agctcgccag caatgtgcag   240
accggcgtgc ccgccagatt cagcggcagc ggcagcagaa ccgacttcac cctgaccatc   300
gaccccgtgg aagaggacga cgtggccgtg tactactgcc tgcagagccg gaccatcccc   360 cggaccttg gcggaggcac caaactggaa atcaagggca gcaccagcgg ctccggcaag   420
cctggctctg gcgagggcag cacaaaggga cagattcagc tggtgcagag cggccctgag   480
ctgaagaaac ccggcgagac agtgaagatc agctgcaagg cctccggcta caccttcacc   540
gactacagca tcaactgggt gaaaagagcc cctggcaagg gcctgaagtg gatgggctgg   600
atcaacaccg agacaagaga gcccgcctac gcctacgact ccggggcag attcgccttc   660 agcctggaaa ccagcgccag caccgcctac ctgcagatca acaacctgaa gtacgaggac   720
accgccacct acttttgcgc cctggactac agctacgcca tggactactg gggccagggc   780
accagcgtga ccgtgtccag c                                              801
```

<210> SEQ ID NO 22
<211> LENGTH: 267
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

```
Met Asp Phe Gln Val Gln Ile Phe Ser Phe Leu Leu Ile Ser Ala Ser
1               5                   10                  15

Val Ile Met Ser Arg Asp Ile Val Leu Thr Gln Ser Pro Pro Ser Leu
            20                  25                  30

Ala Met Ser Leu Gly Lys Arg Ala Thr Ile Ser Cys Arg Ala Ser Glu
```

|   |   |   | 35 |   |   |   | 40 |   |   |   | 45 |   |   |
|---|---|---|---|---|---|---|---|---|---|---|---|---|---|

Ser Val Thr Ile Leu Gly Ser His Leu Ile His Trp Tyr Gln Gln Lys
 50                  55                  60

Pro Gly Gln Pro Pro Thr Leu Leu Ile Gln Leu Ala Ser Asn Val Gln
 65                  70                  75                  80

Thr Gly Val Pro Ala Arg Phe Ser Gly Ser Gly Ser Arg Thr Asp Phe
                 85                  90                  95

Thr Leu Thr Ile Asp Pro Val Glu Glu Asp Asp Val Ala Val Tyr Tyr
                100                 105                 110

Cys Leu Gln Ser Arg Thr Ile Pro Arg Thr Phe Gly Gly Gly Thr Lys
                115                 120                 125

Leu Glu Ile Lys Gly Ser Thr Ser Gly Ser Gly Lys Pro Gly Ser Gly
            130                 135                 140

Glu Gly Ser Thr Lys Gly Gln Ile Gln Leu Val Gln Ser Gly Pro Glu
145                 150                 155                 160

Leu Lys Lys Pro Gly Glu Thr Val Lys Ile Ser Cys Lys Ala Ser Gly
                165                 170                 175

Tyr Thr Phe Thr Asp Tyr Ser Ile Asn Trp Val Lys Arg Ala Pro Gly
                180                 185                 190

Lys Gly Leu Lys Trp Met Gly Trp Ile Asn Thr Glu Thr Arg Glu Pro
            195                 200                 205

Ala Tyr Ala Tyr Asp Phe Arg Gly Arg Phe Ala Phe Ser Leu Glu Thr
210                 215                 220

Ser Ala Ser Thr Ala Tyr Leu Gln Ile Asn Asn Leu Lys Tyr Glu Asp
225                 230                 235                 240

Thr Ala Thr Tyr Phe Cys Ala Leu Asp Tyr Ser Tyr Ala Met Asp Tyr
                245                 250                 255

Trp Gly Gln Gly Thr Ser Val Thr Val Ser Ser
            260                 265

<210> SEQ ID NO 23
<211> LENGTH: 750
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23

```
atggacatcc agatgactca gaccacaagc tccctgtctg caagtctggg cgaccgggtg      60
acaatctcct gcagagcctc tcaggatatt aggaactacc tgaattggta tcagcagaaa     120
cctgatggca cagtcaagct gctgatctac tataccagcc ggctgcactc aggcgtgcca     180
agcaaattct caggaagcgg ctccgggact gactactccc tgaccatctc taacctggag     240
caggaagata ttgttaccta tttctgccag cagggcaata cactgccctg acttttgcc      300
ggaggcacca aactggagat caaggggga ggcgggagtg aggcggggg atcaggagga       360
ggaggcagcg gaggaggagg gtccgaggtc cagctgcagc agagcggacc agaactggtg     420
aagcccggag caagtatgaa aatctcctgt aaggcctcag gatacagctt caccggctat     480
ccgatgaact gggtgaaaca gtcccatggc aagaacctgg aatggatggg gctgattaat     540
ccttacaaag gcgtcagcac ctataatcag aagtttaaag acaaggccac actgactgtg     600
gataagtcta gttcaaccgc ttacatggag ctgctgtccc tgacatctga agacagtgcc     660
gtgtactatt gtgctcggtc tggctactat ggggacagtg attggtactt cgatgtctgg     720
```
ggacagggca ctaccctgac cgtgttttct        750

<210> SEQ ID NO 24
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Met Asp Ile Gln Met Thr Gln Thr Thr Ser Ser Leu Ser Ala Ser Leu
1               5                   10                  15

Gly Asp Arg Val Thr Ile Ser Cys Arg Ala Ser Gln Asp Ile Arg Asn
            20                  25                  30

Tyr Leu Asn Trp Tyr Gln Gln Lys Pro Asp Gly Thr Val Lys Leu Leu
        35                  40                  45

Ile Tyr Tyr Thr Ser Arg Leu His Ser Gly Val Pro Ser Lys Phe Ser
    50                  55                  60

Gly Ser Gly Ser Gly Thr Asp Tyr Ser Leu Thr Ile Ser Asn Leu Glu
65                  70                  75                  80

Gln Glu Asp Ile Val Thr Tyr Phe Cys Gln Gln Gly Asn Thr Leu Pro
                85                  90                  95

Trp Thr Phe Ala Gly Gly Thr Lys Leu Glu Ile Lys Gly Gly Gly Gly
            100                 105                 110

Ser Gly Gly Gly Gly Ser Gly Gly Gly Ser Gly Gly Gly Gly Ser
        115                 120                 125

Glu Val Gln Leu Gln Gln Ser Gly Pro Glu Leu Val Lys Pro Gly Ala
    130                 135                 140

Ser Met Lys Ile Ser Cys Lys Ala Ser Gly Tyr Ser Phe Thr Gly Tyr
145                 150                 155                 160

Pro Met Asn Trp Val Lys Gln Ser His Gly Lys Asn Leu Glu Trp Met
                165                 170                 175

Gly Leu Ile Asn Pro Tyr Lys Gly Val Ser Thr Tyr Asn Gln Lys Phe
            180                 185                 190

Lys Asp Lys Ala Thr Leu Thr Val Asp Lys Ser Ser Ser Thr Ala Tyr
        195                 200                 205

Met Glu Leu Leu Ser Leu Thr Ser Glu Asp Ser Ala Val Tyr Tyr Cys
    210                 215                 220

Ala Arg Ser Gly Tyr Tyr Gly Asp Ser Asp Trp Tyr Phe Asp Val Trp
225                 230                 235                 240

Gly Gln Gly Thr Thr Leu Thr Val Phe Ser
                245                 250

<210> SEQ ID NO 25
<211> LENGTH: 750
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
atggacatcc agatgactca gaccacaagc tccctgtctg caagtctggg cgaccgggtg        60
acaatctcct gcagagcctc tcaggatatt aggaactacc tgaattggta tcagcagaaa       120
cctgatggca gtcaagct gctgatctac tataccagcc ggctgcactc aggcgtgcca        180
agcaaattct caggaagcgg ctccgggact gactactccc tgaccatctc taacctggag       240

```
caggaagata ttgctaccta tttctgccag cagggcaata cactgccctg gacttttgcc      300
ggaggcacca aactggagat caagggggga ggcgggagtg gaggcggggg atcaggagga      360
ggaggcagcg gaggaggagg gtccgaggtc cagctgcagc agagcggacc agaactggtg      420
aagcccggag caagtatgaa aatctcctgt aaggcctcag gatacagctt caccggctat      480
acaatgaact gggtgaaaca gtcccatggc aagaacctgg aatggatggg gctgattaat      540
cctaccaaag gcgtcagcac ctataatcag aagtttaaag acaaggccac actgactgtg      600
gataagtcta gttcaaccgc ttacatggag ctgctgtccc tgacatctga agacagtgcc      660
gtgtactatt gtgctcggtc tggctactat ggggacagtg attggtactt cgatgtctgg      720
ggacagggca ctaccctgac cgtgttttct                                        750
```

<210> SEQ ID NO 26
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

```
Met Asp Ile Gln Met Thr Gln Thr Thr Ser Ser Leu Ser Ala Ser Leu
1               5                   10                  15

Gly Asp Arg Val Thr Ile Ser Cys Arg Ala Ser Gln Asp Ile Arg Asn
            20                  25                  30

Tyr Leu Asn Trp Tyr Gln Gln Lys Pro Asp Gly Thr Val Lys Leu Leu
        35                  40                  45

Ile Tyr Tyr Thr Ser Arg Leu His Ser Gly Val Pro Ser Lys Phe Ser
    50                  55                  60

Gly Ser Gly Ser Gly Thr Asp Tyr Ser Leu Thr Ile Ser Asn Leu Glu
65                  70                  75                  80

Gln Glu Asp Ile Ala Thr Tyr Phe Cys Gln Gln Gly Asn Thr Leu Pro
                85                  90                  95

Trp Thr Phe Ala Gly Gly Thr Lys Leu Glu Ile Lys Gly Gly Gly Gly
            100                 105                 110

Ser Gly Gly Gly Gly Ser Gly Gly Gly Ser Gly Gly Gly Gly Ser
        115                 120                 125

Glu Val Gln Leu Gln Gln Ser Gly Pro Glu Leu Val Lys Pro Gly Ala
    130                 135                 140

Ser Met Lys Ile Ser Cys Lys Ala Ser Gly Tyr Ser Phe Thr Gly Tyr
145                 150                 155                 160

Thr Met Asn Trp Val Lys Gln Ser His Gly Lys Asn Leu Glu Trp Met
                165                 170                 175

Gly Leu Ile Asn Pro Thr Lys Gly Val Ser Thr Tyr Asn Gln Lys Phe
            180                 185                 190

Lys Asp Lys Ala Thr Leu Thr Val Asp Lys Ser Ser Ser Thr Ala Tyr
        195                 200                 205

Met Glu Leu Leu Ser Leu Thr Ser Glu Asp Ser Ala Val Tyr Tyr Cys
    210                 215                 220

Ala Arg Ser Gly Tyr Tyr Gly Asp Ser Asp Trp Tyr Phe Asp Val Trp
225                 230                 235                 240

Gly Gln Gly Thr Thr Leu Thr Val Phe Ser
                245                 250
```

<210> SEQ ID NO 27
<211> LENGTH: 735
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 27

```
atggatatcc agatgaccca gtccccgagc tccctgtccg cctctgtggg cgatagggtc      60
accatcacct gccgtgccag tcaggacatc cgtaattatc tgaactggta tcaacagaaa     120
ccaggaaaag ctccgaaact actgatttac tatacctccc gcctggagtc tggagtccct     180
tctcgcttct ctggttctgg ttctgggacg gattacactc tgaccatcag cagtctgcaa     240
ccggaagact tcgcaactta ttactgtcag caaggtaata ctctgccgtg gacgttcgga     300
cagggcacca aggtggagat caaaggcggc ggcggaagtg gaggaggagg ctcaggcgga     360
ggagggagcg aggttcagct ggtggagtct ggcggtggcc tggtgcagcc agggggctca     420
ctccgtttgt cctgtgcagc ttctggctac tcctttaccg gctacactat gaactgggtg     480
cgtcaggccc caggtaaggg cctggaatgg gttgcactga ttaatcctac caaaggtgtt     540
agtacctaca accagaagtt caaggaccgt ttcactataa gcgtagataa atccaaaaac     600
acagcctacc tgcaaatgaa cagcctgcgt gctgaggaca ctgccgtcta ttattgtgct     660
agaagcggat actacggcga tagtgactgg tatttgacg tgtggggtca aggaaccctg      720
gtcaccgtct cctcg                                                     735
```

<210> SEQ ID NO 28
<211> LENGTH: 245
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 28

```
Met Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asp Ile Arg Asn
            20                  25                  30

Tyr Leu Asn Trp Tyr Gln Gln Lys Pro Gly Lys Ala Pro Lys Leu Leu
        35                  40                  45

Ile Tyr Tyr Thr Ser Arg Leu Glu Ser Gly Val Pro Ser Arg Phe Ser
    50                  55                  60

Gly Ser Gly Ser Gly Thr Asp Tyr Thr Leu Thr Ile Ser Ser Leu Gln
65                  70                  75                  80

Pro Glu Asp Phe Ala Thr Tyr Tyr Cys Gln Gln Gly Asn Thr Leu Pro
                85                  90                  95

Trp Thr Phe Gly Gln Gly Thr Lys Val Glu Ile Lys Gly Gly Gly Gly
            100                 105                 110

Ser Gly Gly Gly Gly Ser Gly Gly Gly Ser Glu Val Gln Leu Val
        115                 120                 125

Glu Ser Gly Gly Gly Leu Val Gln Pro Gly Gly Ser Leu Arg Leu Ser
    130                 135                 140

Cys Ala Ala Ser Gly Tyr Ser Phe Thr Gly Tyr Thr Met Asn Trp Val
145                 150                 155                 160

Arg Gln Ala Pro Gly Lys Gly Leu Glu Trp Val Ala Leu Ile Asn Pro
                165                 170                 175
```

```
Thr Lys Gly Val Ser Thr Tyr Asn Gln Lys Phe Lys Asp Arg Phe Thr
            180                 185                 190

Ile Ser Val Asp Lys Ser Lys Asn Thr Ala Tyr Leu Gln Met Asn Ser
            195                 200                 205

Leu Arg Ala Glu Asp Thr Ala Val Tyr Tyr Cys Ala Arg Ser Gly Tyr
210                 215                 220

Tyr Gly Asp Ser Asp Trp Tyr Phe Asp Val Trp Gly Gln Gly Thr Leu
225                 230                 235                 240

Val Thr Val Ser Ser
                245

<210> SEQ ID NO 29
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Met Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asp Ile Arg Asn
            20                  25                  30

Tyr Leu Asn Trp Tyr Gln Gln Lys Pro Gly Lys Ala Pro Lys Leu Leu
        35                  40                  45

Ile Tyr Tyr Thr Ser Arg Leu Glu Ser Gly Val Pro Ser Arg Phe Ser
50                  55                  60

Gly Ser Gly Ser Gly Thr Asp Tyr Thr Leu Thr Ile Ser Ser Leu Gln
65                  70                  75                  80

Pro Glu Asp Phe Ala Thr Tyr Tyr Cys Gln Gln Gly Asn Thr Leu Pro
                85                  90                  95

Trp Thr Phe Gly Gln Gly Thr Lys Val Glu Ile Lys Gly Gly Gly Gly
            100                 105                 110

Ser Gly Gly Gly Gly Ser Gly Gly Gly Ser Glu Val Gln Leu Val
            115                 120                 125

Glu Ser Gly Gly Gly Leu Val Gln Pro Gly Gly Ser Leu Arg Leu Ser
130                 135                 140

Cys Ala Ala Ser Gly Tyr Ser Phe Thr Gly Tyr Thr Met Asn Trp Val
145                 150                 155                 160

Arg Gln Ala Pro Gly Lys Gly Leu Glu Trp Val Ala Leu Ile Asn Pro
            165                 170                 175

Tyr Lys Gly Val Ser Thr Tyr Asn Gln Lys Phe Lys Asp Arg Phe Thr
            180                 185                 190

Ile Ser Val Asp Lys Ser Lys Asn Thr Ala Tyr Leu Gln Met Asn Ser
            195                 200                 205

Leu Arg Ala Glu Asp Thr Ala Val Tyr Tyr Cys Ala Arg Ser Gly Tyr
210                 215                 220

Tyr Gly Asp Ser Asp Trp Tyr Phe Asp Val Trp Gly Gln Gly Thr Leu
225                 230                 235                 240

Val Thr Val Ser Ser
                245

<210> SEQ ID NO 30
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 30

Gly Gly Gly Gly Ser Gly Gly Gly Gly Ser Gly Gly Gly Gly Ser
1               5                   10                  15
```

T CELL-ANTIGEN COUPLER WITH Y182T MUTATION AND METHODS AND USES THEREOF

CROSS-REFERENCE

This application is the U.S. National Phase entry of International Application No. PCT/US2018/051290, filed on Oct. 12, 2018, which claims the benefit of U.S. Provisional Application No. 62/571,354, filed Oct. 12, 2017, each of which are incorporated herein by reference in their entireties.

SEQUENCE LISTING

The instant application contains a Sequence Listing which has been filed electronically in ASCII format and is hereby incorporated by reference in its entirety. Said ASCII copy, created on Oct. 11, 2018, is named 0034923-00006_SL.txt and is 40,435 bytes in size.

FIELD

The present disclosure relates to a method of treating cancer by engineering T-cells with high cytotoxicity against specific target cells and reduced off-target toxicity. In particular, the disclosure relates to engineering T-cells to express novel biological agents, which trigger the natural T-cell activation process.

SUMMARY

Disclosed herein, in some embodiments, are a nucleic acid sequences encoding a Trifunctional T cell-antigen coupler (Tri-TAC) comprising: (a) a first polynucleotide sequence encoding a ligand that selectively binds a target antigen; (b) a second polynucleotide sequence encoding a UCHT1 ligand with a Y182T mutation comprising an amino acid sequence having at least 80% sequence identity with SEQ ID NO: 26 that binds a protein associated with a T cell receptor (TCR) complex; and (c) a third polynucleotide sequence encoding a TCR signaling domain polypeptide. In some embodiments, the amino acid sequence comprises SEQ ID NO: 26. In some embodiments, the ligand specifically binds the target antigen. In some embodiments, the ligand is an ankyrin repeat (DARPin) polypeptide. In some embodiments, the ligand is a single chain variable fragment (scFv). In some embodiments, the target antigen is a tumor antigen. In some embodiments, the tumor antigen is a HER-2 antigen. In some embodiments, the tumor antigen is a BCMA antigen. In some embodiments, the protein associated with a TCR complex is CD3, preferably CD3ε. In some embodiments, the TCR signaling domain polypeptide comprises a transmembrane domain and a cytosolic domain. In some embodiments, the TCR signaling domain polypeptide comprises a transmembrane domain and a cytosolic domain of a TCR co-receptor. In some embodiments, the TCR co-receptor is CD4. In some embodiments, the TCR co-receptor is CD8, preferably CD8a. In some embodiments, the first polypeptide, the second polypeptide, and the third polypeptide are directly fused. In some embodiments, the first polypeptide and the second polypeptide are directly fused, and joined to the third polypeptide by a linker. In some embodiments, the second polypeptide and the third polypeptide are directly fused, and joined to the first polypeptide by a linker. In some embodiments, the linker is a peptide linker, preferably a peptide linker comprising 5 to 30 amino acids, more preferably 5 amino acids, 10 amino acids, or 15 amino acids. In some embodiments, the peptide linker comprises a G4S3 linker.

Disclosed herein, in some embodiments, are nucleic acid sequences encoding a T cell-antigen coupler (Tri-TAC) comprising: (a) a first polynucleotide sequence encoding a ligand that selectively binds a target antigen; (b) a second polynucleotide sequence encoding a humanized variant of UCHT1 (huUCHT1) ligand comprising an amino acid sequence having at least 80% sequence identity with SEQ ID NO: 29 that binds a protein associated with a T cell receptor (TCR) complex; and (c) a third polynucleotide sequence encoding a TCR signaling domain polypeptide. In some embodiments, the amino acid sequence comprises SEQ ID NO: 29. In some embodiments, the ligand specifically binds the target antigen. In some embodiments, the ligand is an ankyrin repeat (DARPin) polypeptide. In some embodiments, the ligand is a single chain variable fragment (scFv). In some embodiments, the target antigen is a tumor antigen. In some embodiments, the tumor antigen is a HER-2 antigen. In some embodiments, the tumor antigen is a BCMA antigen. In some embodiments, the protein associated with a TCR complex is CD3, preferably CD3ε. In some embodiments, the TCR signaling domain polypeptide comprises a transmembrane domain and a cytosolic domain. In some embodiments, the TCR signaling domain polypeptide comprises a transmembrane domain and a cytosolic domain of a TCR co-receptor. In some embodiments, the TCR co-receptor is CD4. In some embodiments, the TCR co-receptor is CD8, preferably CD8a. In some embodiments, the first polypeptide, the second polypeptide, and the third polypeptide are directly fused. In some embodiments, the first polypeptide and the second polypeptide are directly fused, and joined to the third polypeptide by a linker. In some embodiments, the second polypeptide and the third polypeptide are directly fused, and joined to the first polypeptide by a linker. In some embodiments, the linker is a peptide linker, preferably a peptide linker comprising 5 to 30 amino acids, more preferably 5 amino acids, 10 amino acids, or 15 amino acids. In some embodiments, the peptide linker comprises a G4S3 linker.

Disclosed herein, in some embodiments, are nucleic acid sequences encoding a T cell-antigen coupler (Tri-TAC) comprising: (a) a first polynucleotide sequence encoding a ligand that selectively binds a target antigen; (b) a second polynucleotide sequence encoding a humanized variant of UCHT1 (huUCHT1) ligand with a Y177T mutation comprising an amino acid sequence having at least 80% sequence identity with SEQ ID NO: 28 that binds a protein associated with a T cell receptor (TCR) complex; and (c) a third polynucleotide sequence encoding a TCR signaling domain polypeptide. In some embodiments, the amino acid sequence comprises SEQ ID NO: 28. In some embodiments, the ligand specifically binds the target antigen. In some embodiments, the ligand is an ankyrin repeat (DARPin) polypeptide. In some embodiments, the ligand is a single chain variable fragment (scFv). In some embodiments, the target antigen is a tumor antigen. In some embodiments, the tumor antigen is a HER-2 antigen. In some embodiments, the tumor antigen is a BCMA antigen. In some embodiments, the protein associated with a TCR complex is CD3, preferably CD3ε. In some embodiments, the TCR signaling domain polypeptide comprises a transmembrane domain and a cytosolic domain. In some embodiments, the TCR signaling domain polypeptide comprises a transmembrane domain and a cytosolic domain of a TCR co-receptor. In some embodiments, the TCR co-receptor is CD4. In some embodiments, the TCR co-receptor is CD8, preferably CD8a. In some embodiments, the first polypeptide, the second polypeptide, and the third polypeptide are directly fused. In some embodiments, the first polypeptide and the second polypeptide are directly fused, and joined to the third polypeptide by a linker. In some embodiments, the second polypeptide and the third polypeptide are directly fused, and joined to the first polypeptide by a linker. In some embodiments, the linker is a peptide linker, preferably a peptide linker comprising 5 to 30 amino acids, more preferably 5 amino acids, 10 amino acids, or 15 amino acids. In some embodiments, the peptide linker comprises a G4S3 linker.

Disclosed herein, in some embodiments, are nucleic acid sequences encoding an anti-HER-2 Trifunctional T cell-antigen coupler (anti-HER-2 Tri-TAC) comprising: (a) a first polynucleotide sequence encoding a ligand that selectively binds a HER-2 antigen; (b) a second polynucleotide sequence encoding a UCHT1 ligand with a Y182T mutation comprising an amino acid sequence having at least 80% sequence identity with SEQ ID NO: 26 that binds a protein associated with a T cell receptor (TCR) complex; and (c) a third polynucleotide sequence encoding a TCR signaling domain polypeptide. In some embodiments, the amino acid sequence comprises SEQ ID NO: 26. In some embodiments, the amino acid sequence comprises SEQ ID NO: 29. In some embodiments, the amino acid sequence comprises SEQ ID NO: 28. In some embodiments, the ligand specifically binds the HER-2 antigen. In some embodiments, the ligand is an ankyrin repeat (DARPin) polypeptide. In some embodiments, the HER-2 antigen is expressed on a cancer cell. In some embodiments, the protein associated with a TCR complex is CD3, preferably CD3ε. In some embodiments, the TCR signaling domain polypeptide comprises a transmembrane domain and a cytosolic domain. In some embodiments, the TCR signaling domain polypeptide comprises a transmembrane domain and a cytosolic domain of a TCR co-receptor. In some embodiments, the TCR co-receptor is CD4. In some embodiments, the TCR co-receptor is CD8, preferably CD8a. In some embodiments, the first polypeptide, the second polypeptide, and the third polypeptide are directly fused. In some embodiments, the first polypeptide and the second polypeptide are directly fused, and joined to the third polypeptide by a linker. In some embodiments, the second polypeptide and the third polypeptide are directly fused, and joined to the first polypeptide by a linker. In some embodiments, the linker is a peptide linker, preferably a peptide linker comprising 5 to 30 amino acids, more preferably 5 amino acids, 10 amino acids, or 15 amino acids. In some embodiments, the peptide linker comprises a G4S3 linker.

Disclosed herein, in some embodiments, are nucleic acid sequences encoding an anti-HER-2 Trifunctional T cell-antigen coupler (anti-HER-2 Tri-TAC) comprising: (a) a first polynucleotide sequence encoding a ligand that selectively binds a HER-2 antigen; (b) a second polynucleotide sequence encoding a humanized variant of UCHT1 (huUCHT1) ligand comprising an amino acid sequence having at least 80% sequence identity with SEQ ID NO: 29 that binds a protein associated with a T cell receptor (TCR) complex; and (c) a third polynucleotide sequence encoding a TCR signaling domain polypeptide. In some embodiments, the amino acid sequence comprises SEQ ID NO: 26. In some embodiments, the amino acid sequence comprises SEQ ID NO: 29. In some embodiments, the amino acid sequence comprises SEQ ID NO: 28. In some embodiments, the ligand specifically binds the HER-2 antigen. In some embodiments, the ligand is an ankyrin repeat (DARPin) polypeptide. In some embodiments, the HER-2 antigen is expressed on a cancer cell. In some embodiments, the protein associated with a TCR complex is CD3, preferably CD3ε. In some embodiments, the TCR signaling domain polypeptide comprises a transmembrane domain and a cytosolic domain. In some embodiments, the TCR signaling domain polypeptide comprises a transmembrane domain and a cytosolic domain of a TCR co-receptor. In some embodiments, the TCR co-receptor is CD4. In some embodiments, the TCR co-receptor is CD8, preferably CD8a. In some embodiments, the first polypeptide, the second polypeptide, and the third polypeptide are directly fused. In some embodiments, the first polypeptide and the second polypeptide are directly fused, and joined to the third polypeptide by a linker. In some embodiments, the second polypeptide and the third polypeptide are directly fused, and joined to the first polypeptide by a linker. In some embodiments, the linker is a peptide linker, preferably a peptide linker comprising 5 to 30 amino acids, more preferably 5 amino acids, 10 amino acids, or 15 amino acids. In some embodiments, the peptide linker comprises a G4S3 linker.

Disclosed herein, in some embodiments, are nucleic acid sequences encoding an anti-HER-2 Trifunctional T cell-antigen coupler (anti-HER-2 Tri-TAC) comprising: (a) a first polynucleotide sequence encoding a ligand that selectively binds a HER-2 antigen; (b) a second polynucleotide sequence encoding a humanized variant of UCHT1 (huUCHT1) ligand with a Y177T mutation comprising an amino acid sequence having at least 80% sequence identity with SEQ ID NO: 28 that binds a protein associated with a T cell receptor (TCR) complex; and (c) a third polynucleotide sequence encoding a TCR signaling domain polypeptide. In some embodiments, the amino acid sequence comprises SEQ ID NO: 26. In some embodiments, the amino acid sequence comprises SEQ ID NO: 29. In some embodiments, the amino acid sequence comprises SEQ ID NO: 28. In some embodiments, the ligand specifically binds the HER-2 antigen. In some embodiments, the ligand is an ankyrin repeat (DARPin) polypeptide. In some embodiments, the HER-2 antigen is expressed on a cancer cell. In some embodiments, the protein associated with a TCR complex is CD3, preferably CD3ε. In some embodiments, the TCR signaling domain polypeptide comprises a transmembrane domain and a cytosolic domain. In some embodiments, the TCR signaling domain polypeptide comprises a transmembrane domain and a cytosolic domain of a TCR co-receptor. In some embodiments, the TCR co-receptor is CD4. In some embodiments, the TCR co-receptor is CD8, preferably CD8α. In some embodiments, the first polypeptide, the second polypeptide, and the third polypeptide are directly fused. In some embodiments, the first polypeptide and the second polypeptide are directly fused, and joined to the third polypeptide by a linker. In some embodiments, the second polypeptide and the third polypeptide are directly fused, and joined to the first polypeptide by a linker. In some embodiments, the linker is a peptide linker, preferably a peptide linker comprising 5 to 30 amino acids, more preferably 5 amino acids, 10 amino acids, or 15 amino acids. In some embodiments, the peptide linker comprises a G4S3 linker.

Disclosed herein, in some embodiments, are nucleic acid sequences encoding an anti-BCMA Trifunctional T cell-antigen coupler (anti-BCMA Tri-TAC) comprising: (a) a first polynucleotide sequence encoding a ligand that selectively binds a BCMA antigen; (b) a second polynucleotide sequence encoding a UCHT1 ligand with a Y182T mutation comprising an amino acid sequence having at least 80% sequence identity with SEQ ID NO: 26 that binds a protein associated with a T cell receptor (TCR) complex; and (c) a third polynucleotide sequence encoding a TCR signaling domain polypeptide. In some embodiments, the amino acid sequence comprises SEQ ID NO: 26. In some embodiments, the amino acid sequence comprises SEQ ID NO: 29. In some embodiments, the amino acid sequence comprises SEQ ID NO: 28. In some embodiments, the ligand specifically binds the BCMA antigen. In some embodiments, the ligand is a single chain variable fragment (scFv). In some embodiments, the BCMA antigen is expressed on a cancer cell. In some embodiments, the protein associated with a TCR complex is CD3, preferably CD3ε. In some embodiments, the TCR signaling domain polypeptide comprises a transmembrane domain and a cytosolic domain. In some embodiments, the TCR signaling domain polypeptide comprises a transmembrane domain and a cytosolic domain of a TCR co-receptor. In some embodiments, the TCR co-receptor is CD4. In some embodiments, the TCR co-receptor is CD8, preferably CD8α. In some embodiments, the first polypeptide, the second polypeptide, and the third polypeptide are directly fused. In some embodiments, the first polypeptide and the second polypeptide are directly fused, and joined to the third polypeptide by a linker. In some embodiments, the second polypeptide and the third polypeptide are directly fused, and joined to the first polypeptide by a linker. In some embodiments, the linker is a peptide linker, preferably a peptide linker comprising 5 to 30 amino acids, more preferably 5 amino acids, 10 amino acids, or 15 amino acids. In some embodiments, the peptide linker comprises a G4S3 linker.

Disclosed herein, in some embodiments, are nucleic acid sequences encoding an anti-BCMA Trifunctional T cell-antigen coupler (anti-BCMA Tri-TAC) comprising: (a) a first polynucleotide sequence encoding a ligand that selectively binds a BCMA antigen; (b) a second polynucleotide sequence encoding a humanized variant of UCHT1 (huUCHT1) ligand comprising an amino acid sequence having at least 80% sequence identity with SEQ ID NO: 29 that binds a protein associated with a T cell receptor (TCR) complex; and (c) a third polynucleotide sequence encoding a TCR signaling domain polypeptide. In some embodiments, the amino acid sequence comprises SEQ ID NO: 26. In some embodiments, the amino acid sequence comprises SEQ ID NO: 29. In some embodiments, the amino acid sequence comprises SEQ ID NO: 28. In some embodiments, the ligand specifically binds the BCMA antigen. In some embodiments, the ligand is a single chain variable fragment (scFv). In some embodiments, the BCMA antigen is expressed on a cancer cell. In some embodiments, the protein associated with a TCR complex is CD3, preferably CD3ε. In some embodiments, the TCR signaling domain polypeptide comprises a transmembrane domain and a cytosolic domain. In some embodiments, the TCR signaling domain polypeptide comprises a transmembrane domain and a cytosolic domain of a TCR co-receptor. In some embodiments, the TCR co-receptor is CD4. In some embodiments, the TCR co-receptor is CD8, preferably CD8α. In some embodiments, the first polypeptide, the second polypeptide, and the third polypeptide are directly fused. In some embodiments, the first polypeptide and the second polypeptide are directly fused, and joined to the third polypeptide by a linker. In some embodiments, the second polypeptide and the third polypeptide are directly fused, and joined to the first polypeptide by a linker. In some embodiments, the linker is a peptide linker, preferably a peptide linker comprising 5 to 30 amino acids, more preferably 5 amino acids, 10 amino acids, or 15 amino acids. In some embodiments, the peptide linker comprises a G453 linker.

Disclosed herein, in some embodiments, are nucleic acid sequences encoding an anti-BCMA Trifunctional T cell-antigen coupler (anti-BCMA Tri-TAC) comprising: (a) a first polynucleotide sequence encoding a ligand that selectively binds a BCMA antigen; (b) a second polynucleotide sequence encoding a humanized variant of UCHT1 (huUCHT1) ligand with a Y177T mutation comprising an amino acid sequence having at least 80% sequence identity with SEQ ID NO: 28 that binds a protein associated with a T cell receptor (TCR) complex; and (c) a third polynucleotide sequence encoding a TCR signaling domain polypeptide. In some embodiments, the amino acid sequence comprises SEQ ID NO: 26. In some embodiments, the amino acid sequence comprises SEQ ID NO: 29. In some embodiments, the amino acid sequence comprises SEQ ID NO: 28. In some embodiments, the ligand specifically binds the BCMA antigen. In some embodiments, the ligand is a single chain variable fragment (scFv). In some embodiments, the BCMA antigen is expressed on a cancer cell. In some embodiments, the protein associated with a TCR complex is CD3, preferably CD3ε. In some embodiments, the TCR signaling domain polypeptide comprises a transmembrane domain and a cytosolic domain. In some embodiments, the TCR signaling domain polypeptide comprises a transmembrane domain and a cytosolic domain of a TCR co-receptor. In some embodiments, the TCR co-receptor is CD4. In some embodiments, the TCR co-receptor is CD8, preferably CD8α. In some embodiments, the first polypeptide, the second polypeptide, and the third polypeptide are directly fused. In some embodiments, the first polypeptide and the second polypeptide are directly fused, and joined to the third polypeptide by a linker. In some embodiments, the second polypeptide and the third polypeptide are directly fused, and joined to the first polypeptide by a linker. In some embodiments, the linker is a peptide linker, preferably a peptide linker comprising 5 to 30 amino acids, more preferably 5 amino acids, 10 amino acids, or 15 amino acids. In some embodiments, the peptide linker comprises a G453 linker.

Disclosed herein, in some embodiments, are vectors comprising the nucleic acid sequence disclosed herein. In some embodiments, the vector further comprises a promoter, preferably a promoter functional in a mammalian cell.

Disclosed herein, in some embodiments, are T cells transfected with the vector disclosed herein.

Disclosed herein, in some embodiments, are engineered T cells comprising the nucleic acid sequence disclosed herein, or the vector disclosed herein.

Disclosed herein, in some embodiments, are pharmaceutical compositions comprising the engineered T cells disclosed herein, and a pharmaceutically acceptable carrier.

Disclosed herein, in some embodiments, are methods of treating a cancer expressing a target antigen in an individual in need thereof, comprising administering to the individual an engineered T cell comprising a nucleic acid sequence encoding a Trifunctional T cell-antigen coupler (Tri-TAC) comprising: (a) a first polynucleotide sequence encoding a ligand that selectively binds the target antigen; (b) a second polynucleotide sequence encoding a UCHT1 ligand with a Y182T mutation comprising an amino acid sequence having at least 80% sequence identity with SEQ ID NO: 26 that binds a protein associated with a T cell receptor (TCR) complex; and (c) a third polynucleotide sequence encoding a TCR signaling domain polypeptide. In some embodiments, the amino acid sequence comprises SEQ ID NO: 26. In some embodiments, the ligand specifically binds the target antigen. In some embodiments, the ligand is an ankyrin repeat (DARPin) polypeptide. In some embodiments, the ligand is a single chain variable fragment (scFv). In some embodiments, the target antigen is a tumor antigen. In some embodiments, the antigen is a HER-2 antigen. In some embodiments, the antigen is a BCMA antigen. In some embodiments, the protein associated with a TCR complex is CD3, preferably CD3ε. In some embodiments, the TCR signaling domain polypeptide comprises a transmembrane domain and a cytosolic domain. In some embodiments, the TCR signaling domain polypeptide comprises a transmembrane domain and a cytosolic domain of a TCR co-receptor. In some embodiments, the TCR co-receptor is CD4. In some embodiments, the TCR co-receptor is CD8, preferably CD8α. In some embodiments, the first polypeptide, the second polypeptide, and the third polypeptide are directly fused. In some embodiments, the first polypeptide and the second polypeptide are directly fused, and joined to the third polypeptide by a linker. In some embodiments, the second polypeptide and the third polypeptide are directly fused, and joined to the first polypeptide by a linker. In some embodiments, the linker is a peptide linker, preferably a peptide linker comprising 5 to 30 amino acids, more preferably 5 amino acids, 10 amino acids, or 15 amino acids. In some embodiments, the peptide linker comprises a G4S3 linker. In some embodiments, the cancer is a solid cancer or a liquid cancer. In some embodiments, the cancer is a lung cancer, a breast cancer, a colon cancer, multiple myeloma, glioblastoma, gastric cancer, ovarian cancer, stomach cancer, colorectal cancer, urothelial cancer, endometrial cancer, or a melanoma.

Disclosed herein, in some embodiments, are methods of treating a cancer expressing a target antigen in an individual in need thereof, comprising administering to the individual an engineered T cell comprising a nucleic acid sequence encoding a Trifunctional T cell-antigen coupler (Tri-TAC) comprising: (a) a first polynucleotide sequence encoding a ligand that selectively binds the target antigen; (b) a second polynucleotide sequence encoding a humanized variant of UCHT1 (huUCHT1) ligand comprising an amino acid sequence having at least 80% sequence identity with SEQ ID NO: 29 that binds a protein associated with a T cell receptor (TCR) complex; and (c) a third polynucleotide sequence encoding a TCR signaling domain polypeptide. In some embodiments, the amino acid sequence comprises SEQ ID NO: 29. In some embodiments, the ligand specifically binds the target antigen. In some embodiments, the ligand is an ankyrin repeat (DARPin) polypeptide. In some embodiments, the ligand is a single chain variable fragment (scFv). In some embodiments, the target antigen is a tumor antigen. In some embodiments, the antigen is a HER-2 antigen. In some embodiments, the antigen is a BCMA antigen. In some embodiments, the protein associated with a TCR complex is CD3, preferably CD3ε. In some embodiments, the TCR signaling domain polypeptide comprises a transmembrane domain and a cytosolic domain. In some embodiments, the TCR signaling domain polypeptide comprises a transmembrane domain and a cytosolic domain of a TCR co-receptor. In some embodiments, the TCR co-receptor is CD4. In some embodiments, the TCR co-receptor is CD8, preferably CD8α. In some embodiments, the first polypeptide, the second polypeptide, and the third polypeptide are directly fused. In some embodiments, the first polypeptide and the second polypeptide are directly fused, and joined to the third polypeptide by a linker. In some embodiments, the second polypeptide and the third polypeptide are directly fused, and joined to the first polypeptide by a linker. In some embodiments, the linker is a peptide linker, preferably a peptide linker comprising 5 to 30 amino acids, more preferably 5 amino acids, 10 amino acids, or 15 amino acids. In some embodiments, the peptide linker comprises a G4S3 linker. In some embodiments, the cancer is a solid cancer or a liquid cancer. In some embodiments, the cancer is a lung cancer, a breast cancer, a colon cancer, multiple myeloma, glioblastoma, gastric cancer, ovarian cancer, stomach cancer, colorectal cancer, urothelial cancer, endometrial cancer, or a melanoma.

Disclosed herein, in some embodiments, are methods of treating a cancer expressing a target antigen in an individual in need thereof, comprising administering to the individual an engineered T cell comprising a nucleic acid sequence encoding a T cell-antigen coupler (Tri-TAC) comprising: (a) a first polynucleotide sequence encoding a ligand that selectively binds the target antigen; (b) a second polynucleotide sequence encoding a humanized variant UCHT1 (huUCHT1) ligand with a Y177T mutation comprising an amino acid sequence having at least 80% sequence identity with SEQ ID NO: 28 that binds a protein associated with a T cell receptor (TCR) complex; and (c) a third polynucleotide sequence encoding a TCR signaling domain polypeptide. In some embodiments, the amino acid sequence comprises SEQ ID NO: 28. In some embodiments, the ligand specifically binds the target antigen. In some embodiments, the ligand is an ankyrin repeat (DARPin) polypeptide. In some embodiments, the ligand is a single chain variable fragment (scFv). In some embodiments, the target antigen is a tumor antigen. In some embodiments, the antigen is a HER-2 antigen. In some embodiments, the antigen is a BCMA antigen. In some embodiments, the protein associated with a TCR complex is CD3, preferably CD3ε. In some embodiments, the TCR signaling domain polypeptide comprises a transmembrane domain and a cytosolic domain. In some embodiments, the TCR signaling domain polypeptide comprises a transmembrane domain and a cytosolic domain of a TCR co-receptor. In some embodiments, the TCR co-receptor is CD4. In some embodiments, the TCR co-receptor is CD8, preferably CD8α. In some embodiments, the first polypeptide, the second polypeptide, and the third polypeptide are directly fused. In some embodiments, the first polypeptide and the second polypeptide are directly fused, and joined to the third polypeptide by a linker. In some embodiments, the second polypeptide and the third polypeptide are directly fused, and joined to the first polypeptide by a linker. In some embodiments, the linker is a peptide linker, preferably a peptide linker comprising 5 to 30 amino acids, more preferably 5 amino acids, 10 amino acids, or 15 amino acids. In some embodiments, the peptide linker comprises a G4S3 linker. In some embodiments, the cancer is a solid cancer or a liquid cancer. In some embodiments, the cancer is a lung cancer, a breast cancer, a colon cancer, multiple myeloma, glioblastoma, gastric cancer, ovarian cancer, stomach cancer, colorectal cancer, urothelial cancer, endometrial cancer, or a melanoma.

Disclosed herein, in some embodiments, are methods of treating a cancer expressing a HER-2 antigen in an individual in need thereof, comprising administering to the individual an engineered T cell comprising a nucleic acid sequence encoding an anti-HER-2 Trifunctional T cell-antigen coupler (anti-HER-2 Tri-TAC) comprising: (a) a first polynucleotide sequence encoding a ligand that selectively binds the HER-2 antigen; (b) a second polynucleotide sequence encoding a UCHT1 ligand with a Y182T mutation comprising an amino acid sequence having at least 80% sequence identity with SEQ ID NO: 26 that binds a protein associated with a T cell receptor (TCR) complex; and (c) a third polynucleotide sequence encoding a TCR signaling domain polypeptide. In some embodiments, the amino acid sequence comprises SEQ ID NO: 26. In some embodiments, the ligand specifically binds the HER-2 antigen. In some embodiments, the ligand is an ankyrin repeat (DARPin) polypeptide. In some embodiments, the protein associated with a TCR complex is CD3, preferably CD3ε. In some embodiments, the TCR signaling domain polypeptide comprises a transmembrane domain and a cytosolic domain. In some embodiments, the TCR signaling domain polypeptide comprises a transmembrane domain and a cytosolic domain of a TCR co-receptor. In some embodiments, the TCR co-receptor is CD4. In some embodiments, the TCR co-receptor is CD8, preferably CD8α. In some embodiments, the first polypeptide, the second polypeptide, and the third polypeptide are directly fused. In some embodiments, the first polypeptide and the second polypeptide are directly fused, and joined to the third polypeptide by a linker. In some embodiments, the second polypeptide and the third polypeptide are directly fused, and joined to the first polypeptide by a linker. In some embodiments, the linker is a peptide linker, preferably a peptide linker comprising 5 to 30 amino acids, more preferably 5 amino acids, 10 amino acids, or 15 amino acids. In some embodiments, the peptide linker comprises a G4S3 linker. In some embodiments, the cancer is a solid cancer or a liquid cancer. In some embodiments, the cancer is a lung cancer, a breast cancer, multiple myeloma, glioblastoma, gastric cancer, ovarian cancer, stomach cancer, colorectal cancer, urothelial cancer, endometrial cancer, or a colon cancer.

Disclosed herein, in some embodiments, are methods of treating a cancer expressing a HER-2 antigen in an individual in need thereof, comprising administering to the individual an engineered T cell comprising a nucleic acid sequence encoding an anti-HER-2 Trifunctional T cell-antigen coupler (anti-HER-2 Tri-TAC) comprising: (a) a first polynucleotide sequence encoding a ligand that selectively binds the HER-2 antigen; (b) a second polynucleotide sequence encoding a humanized variant of UCHT1 (huUCHT1) ligand comprising an amino acid sequence having at least 80% sequence identity with SEQ ID NO: 29 that binds a protein associated with a T cell receptor (TCR) complex; and (c) a third polynucleotide sequence encoding a TCR signaling domain polypeptide. In some embodiments, the amino acid sequence comprises SEQ ID NO: 29. In some embodiments, the ligand specifically binds the HER-2 antigen. In some embodiments, the ligand is an ankyrin repeat (DARPin) polypeptide. In some embodiments, the protein associated with a TCR complex is CD3, preferably CD3ε. In some embodiments, the TCR signaling domain polypeptide comprises a transmembrane domain and a cytosolic domain. In some embodiments, the TCR signaling domain polypeptide comprises a transmembrane domain and a cytosolic domain of a TCR co-receptor. In some embodiments, the TCR co-receptor is CD4. In some embodiments, the TCR co-receptor is CD8, preferably CD8α. In some embodiments, the first polypeptide, the second polypeptide, and the third polypeptide are directly fused. In some embodiments, the first polypeptide and the second polypeptide are directly fused, and joined to the third polypeptide by a linker. In some embodiments, the second polypeptide and the third polypeptide are directly fused, and joined to the first polypeptide by a linker. In some embodiments, the linker is a peptide linker, preferably a peptide linker comprising 5 to 30 amino acids, more preferably 5 amino acids, 10 amino acids, or 15 amino acids. In some embodiments, the peptide linker comprises a G4S3 linker. In some embodiments, the cancer is a solid cancer or a liquid cancer. In some embodiments, the cancer is a lung cancer, a breast cancer, multiple myeloma, glioblastoma, gastric cancer, ovarian cancer, stomach cancer, colorectal cancer, urothelial cancer, endometrial cancer, or a colon cancer.

Disclosed herein, in some embodiments, are methods of treating a cancer expressing a HER-2 antigen in an individual in need thereof, comprising administering to the individual an engineered T cell comprising a nucleic acid sequence encoding an anti-HER-2 Trifunctional T cell-antigen coupler (anti-HER-2 Tri-TAC) comprising: (a) a first polynucleotide sequence encoding a ligand that selectively binds the HER-2 antigen; (b) a second polynucleotide sequence encoding a humanized variant of UCHT1 (huUCHT1) ligand with a Y177T mutation comprising an amino acid sequence having at least 80% sequence identity with SEQ ID NO: 28 that binds a protein associated with a T cell receptor (TCR) complex; and (c) a third polynucleotide sequence encoding a TCR signaling domain polypeptide. In some embodiments, the amino acid sequence comprises SEQ ID NO: 28. In some embodiments, the ligand specifically binds the HER-2 antigen. In some embodiments, the ligand is an ankyrin repeat (DARPin) polypeptide. In some embodiments, the protein associated with a TCR complex is CD3, preferably CD3ε. In some embodiments, the TCR signaling domain polypeptide comprises a transmembrane domain and a cytosolic domain. In some embodiments, the TCR signaling domain polypeptide comprises a transmembrane domain and a cytosolic domain of a TCR co-receptor. In some embodiments, the TCR co-receptor is CD4. In some embodiments, the TCR co-receptor is CD8, preferably CD8α. In some embodiments, the first polypeptide, the second polypeptide, and the third polypeptide are directly fused. In some embodiments, the first polypeptide and the second polypeptide are directly fused, and joined to the third polypeptide by a linker. In some embodiments, the second polypeptide and the third polypeptide are directly fused, and joined to the first polypeptide by a linker. In some embodiments, the linker is a peptide linker, preferably a peptide linker comprising 5 to 30 amino acids, more preferably 5 amino acids, 10 amino acids, or 15 amino acids. In some embodiments, the peptide linker comprises a G4S3 linker. In some embodiments, the cancer is a solid cancer or a liquid cancer. In some embodiments, the cancer is a lung cancer, a breast cancer, multiple myeloma, glioblastoma, gastric cancer, ovarian cancer, stomach cancer, colorectal cancer, urothelial cancer, endometrial cancer, or a colon cancer.

Disclosed herein, in some embodiments, are methods of treating a cancer expressing a BCMA antigen in an individual in need thereof, comprising administering to the individual an engineered T cell comprising a nucleic acid sequence encoding an anti-BCMA Trifunctional T cell-antigen coupler (anti-BCMA Tri-TAC) comprising: (a) a first polynucleotide sequence encoding a ligand that selectively binds the BCMA antigen; (b) a second polynucleotide sequence encoding a UCHT1 ligand with a Y182T mutation comprising an amino acid sequence having at least 80% sequence identity with SEQ ID NO: 26 that binds a protein associated with a T cell receptor (TCR) complex; and (c) a third polynucleotide sequence encoding a TCR signaling domain polypeptide. In some embodiments, the amino acid sequence comprises SEQ ID NO: 26. In some embodiments, the ligand specifically binds the BCMA antigen. In some embodiments, the ligand is a single chain variable fragment (scFv). In some embodiments, the protein associated with a TCR complex is CD3, preferably CD3ε. In some embodiments, the TCR signaling domain polypeptide comprises a transmembrane domain and a cytosolic domain. In some embodiments, the TCR signaling domain polypeptide comprises a transmembrane domain and a cytosolic domain of a TCR co-receptor. In some embodiments, the TCR co-receptor is CD4. In some embodiments, the TCR co-receptor is CD8, preferably CD8α. In some embodiments, the first polypeptide, the second polypeptide, and the third polypeptide are directly fused. In some embodiments, the first polypeptide and the second polypeptide are directly fused, and joined to the third polypeptide by a linker. In some embodiments, the second polypeptide and the third polypeptide are directly fused, and joined to the first polypeptide by a linker. In some embodiments, the linker is a peptide linker, preferably a peptide linker comprising 5 to 30 amino acids, more preferably 5 amino acids, 10 amino acids, or 15 amino acids. In some embodiments, the peptide linker comprises a G4S3 linker. In some embodiments, the cancer is a solid cancer or a liquid cancer. In some embodiments, the cancer is a multiple myeloma.

Disclosed herein, in some embodiments, are methods of treating a cancer expressing a BCMA antigen in an individual in need thereof, comprising administering to the individual an engineered T cell comprising a nucleic acid sequence encoding an anti-BCMA Trifunctional T cell-antigen coupler (anti-BCMA Tri-TAC) comprising: (a) a first polynucleotide sequence encoding a ligand that selectively binds the BCMA antigen; (b) a second polynucleotide sequence encoding a humanized variant of UCHT1 (huUCHT1) ligand comprising an amino acid sequence having at least 80% sequence identity with SEQ ID NO: 29 that binds a protein associated with a T cell receptor (TCR) complex; and (c) a third polynucleotide sequence encoding a TCR signaling domain polypeptide. In some embodiments, the amino acid sequence comprises SEQ ID NO: 29. In some embodiments, the ligand specifically binds the BCMA antigen. In some embodiments, the ligand is a single chain variable fragment (scFv). In some embodiments, the protein associated with a TCR complex is CD3, preferably CD3ε. In some embodiments, the TCR signaling domain polypeptide comprises a transmembrane domain and a cytosolic domain. In some embodiments, the TCR signaling domain polypeptide comprises a transmembrane domain and a cytosolic domain of a TCR co-receptor. In some embodiments, the TCR co-receptor is CD4. In some embodiments, the TCR co-receptor is CD8, preferably CD8α. In some embodiments, the first polypeptide, the second polypeptide, and the third polypeptide are directly fused. In some embodiments, the first polypeptide and the second polypeptide are directly fused, and joined to the third polypeptide by a linker. In some embodiments, the second polypeptide and the third polypeptide are directly fused, and joined to the first polypeptide by a linker. In some embodiments, the linker is a peptide linker, preferably a peptide linker comprising 5 to 30 amino acids, more preferably 5 amino acids, 10 amino acids, or 15 amino acids. In some embodiments, the peptide linker comprises a G453 linker. In some embodiments, the cancer is a solid cancer or a liquid cancer. In some embodiments, the cancer is a multiple myeloma.

Disclosed herein, in some embodiments, are methods of treating a cancer expressing a BCMA antigen in an individual in need thereof, comprising administering to the individual an engineered T cell comprising a nucleic acid sequence encoding an anti-BCMA Trifunctional T cell-antigen coupler (anti-BCMA Tri-TAC) comprising: (a) a first polynucleotide sequence encoding a ligand that selectively binds the BCMA antigen; (b) a second polynucleotide sequence encoding a humanized variant of UCHT1 (huUCHT1) ligand with a Y177T mutation comprising an amino acid sequence having at least 80% sequence identity with SEQ ID NO: 28 that binds a protein associated with a T cell receptor (TCR) complex; and (c) a third polynucleotide sequence encoding a TCR signaling domain polypeptide. In some embodiments, the amino acid sequence comprises SEQ ID NO: 28. In some embodiments, the ligand specifically binds the BCMA antigen. In some embodiments, the ligand is a single chain variable fragment (scFv). In some embodiments, the protein associated with a TCR complex is CD3, preferably CD3ε. In some embodiments, the TCR signaling domain polypeptide comprises a transmembrane domain and a cytosolic domain. In some embodiments, the TCR signaling domain polypeptide comprises a transmembrane domain and a cytosolic domain of a TCR co-receptor. In some embodiments, the TCR co-receptor is CD4. In some embodiments, the TCR co-receptor is CD8, preferably CD8α. In some embodiments, the first polypeptide, the second polypeptide, and the third polypeptide are directly fused. In some embodiments, the first polypeptide and the second polypeptide are directly fused, and joined to the third polypeptide by a linker. In some embodiments, the second polypeptide and the third polypeptide are directly fused, and joined to the first polypeptide by a linker. In some embodiments, the linker is a peptide linker, preferably a peptide linker comprising 5 to 30 amino acids, more preferably 5 amino acids, 10 amino acids, or 15 amino acids. In some embodiments, the peptide linker comprises a G4S3 linker. In some embodiments, the cancer is a solid cancer or a liquid cancer. In some embodiments, the cancer is a multiple myeloma.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2C is a schematic of a Tri-TAC molecule with the Anti-BCMA scFv antigen binding domain.

FIG. 3A exemplifies the surface expression of the Tri-TAC and CAR compared to T cells that express no chimeric receptor. FIG. 3B exemplifies growth of 3 cell populations.

FIG. 4A exemplifies cell surface expression (left), degranulation (middle) and cytokine production (right) and FIG. 4B exemplifies that only full length anti-HER-2 DARPin Tri-TAC is able to elicit a cytotoxic response.

FIG. 5A exemplifies the ability of full length TAC and the cytosolic deletion to pull down Lck and FIG. 5B illustrates a densitometry analysis of Lck detected in the pellets of FIG. 5A.

FIG. 6A exemplifies the change in tumor growth relative to the day of T cell infusion (day 35) and FIG. 6B exemplifies the change in weight, a measure of toxicity, in the same mice.

FIG. 7A is an exemplary schematic representation of the mutant, FIG. 7B illustrates a histogram showing surface expression of the library and FIG. 7C illustrates the ability of the library to activate T cells and produce cytokines.

FIG. 8A illustrates the distribution of CD8/CD4 T cells at the end of the manufacturing process. FIG. 8B illustrates the level of transduction. FIG. 8C exemplifies cytokine production following stimulation with cells expressing HER-2.

FIG. 9A exemplifies surface expression of the anti-HER-2 DARPin Tri-TAC variants in CD4 and CD8 cells. FIG. 9B illustrates the ability of the Tri-TAC variants to induce expression of T cell functional indicators following stimulation with SKOV3 cells that express HER-2. FIG. 9C illustrates the ability of the Tri-TAC variants to express cytotoxicity against SKOV3 cells.

FIG. 11A-FIG. 11C illustrate the sequence alignment of various UCHT1 variants. FIG. 11A is wild type UCHT1 aligned with the UCHT1 Y182T identified through enrichment analysis. FIG. 11B is wild type UCHT1 aligned with a humanized UCHT1 (huUCHT1). FIG. 11C is huUCHT1 aligned with a huUCHT1 variant carrying the corresponding mutation from UCHT1 Y182T, named huUCHT1 Y177T.

FIG. 15A exemplifies phenotypic analysis of Tri-TAC expression. FIG. 15B illustrates cytokine production following co-culture with KMS-11 myeloma cells (BCMA-positive) or SKOV-3 ovarian cancer cells (BMCA-negative). FIG. 15C illustrates cytotoxicity triggered by the 2 Tri-TACs following co-culture with KMS-11 or SKOV-3.

FIG. 17 illustrates anti-tumor activity of T cells engineered with either the anti-HER-2 DARPin Tri-TAC carrying huUCHT1 or huUCHT1(Y177T). Mice bearing established OVCAR-3 tumors were treated with T cells engineered with a control Tri-TAC that has no tumor binding domain (panels A and D), the anti-HER-2 DARPin Tri-TAC with huUCHT1 (panels B and E) or the anti-HER-2 DARPin Tri-TAC with huUCHT1(Y177T) (panels C and F). The Y-axes represent the change in tumor growth relative to the day of T cell infusion. The X-axes represent the time relative to the day of T cell infusion. T cell products were produced from two different donors.

FIG. 18 is a nucleotide sequence of huUCHTI (SEQ ID NO: 31).

DETAILED DESCRIPTION

Figure 1A:
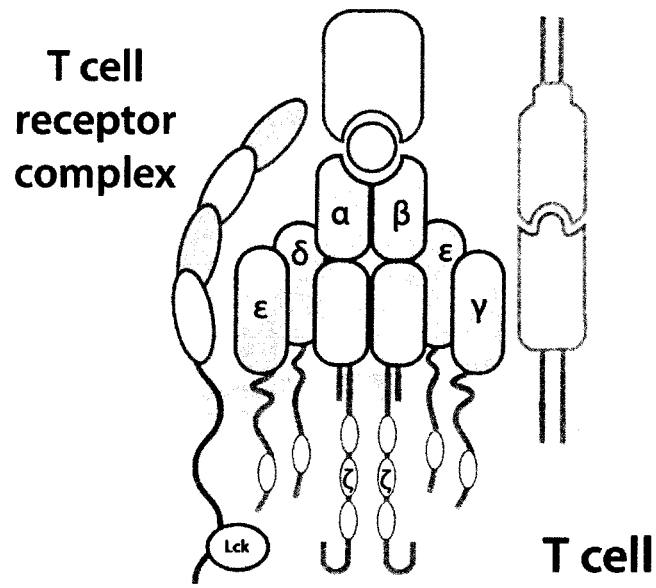
FIG. 1A is a schematic of natural T-cell activation.

Cancer is a major health challenge, with over 150,000 cases of cancer expected to be diagnosed in Canada in 2013 alone. While patients with early stage disease can be treated effectively by conventional therapies (surgery, radiation, chemotherapy), few options are available to patients with advanced disease and those options are typically palliative in nature.

Active immunotherapy seeks to employ the patient's immune system to clear tumor deposits and offers an exciting option to patients who have failed conventional therapies. Generally, this treatment involves infusing patients with large numbers of tumor-specific T cells. This approach has proven to be successful in early phase clinical trials for a number of diseases, including melanoma, myeloma, leukemia, lymphoma and synovial sarcoma. As a specific example, several clinical studies have demonstrated that immunotherapy with T cells can be curative in patients with advanced melanoma, confirming the utility of this approach. Additionally, patients suffering from chronic lymphocytic leukemia (CLL) and acute lymphoblastic leukemia (ALL) have also been effectively treated and cured with T cell immunotherapy.

A key challenge facing the clinical application of adoptive T cell therapy is the source of the T cells. Typically, T cells isolated from a tumor-bearing patient are grown to large numbers ex vivo and are administered back into the patient to induce a robust anti-tumor immune response. Tumor specificity can be achieved by either: (i) isolating naturally occurring tumor-specific T cells from the patient; or (ii) engineering bulk T cells from the peripheral blood to express tumor-specific receptors. Naturally occurring tumor-specific T cells are rare and isolating such cells in therapeutic quantities from cancer patients is a laborious and costly procedure. In contrast, it is becoming more efficient to engineer readily available peripheral T cells with tumor-specific receptors through genetic manipulation. Techniques have been developed for this engineering process which are clinically viable, and several clinical trials have demonstrated the feasibility and efficacy of genetically-engineered T cells for the treatment of cancer.

To this point, most engineered T cell therapies involving genetic modification of the T cells yield: (i) forced expression of T cell receptor (TCR); or (ii) a chimeric antigen receptor (CAR) specific for antigen targets on the tumor. To date, the chimeric antigen receptors used for engineering T cells consist of: (i) a targeting domain, usually a single-chain fragment variable (scFv); (ii) a transmembrane domain; and (iii) a cytosolic domain that contains signaling elements from the T cell receptor and associated proteins. Such chimeric antigen receptors have also been referred to as "T-body" or "Chimeric Immune Receptor" (CIR), but currently, most researchers use the term "CAR". One advantage of the CAR approach is that it allows any patient's immune cells to be targeted against any desirable target in a major histocompatibility complex (MHC) independent manner. This is appealing as MHC presentation is often defective in tumor cells.

CARs are considered in modular terms and scientists have spent considerable time investigating the influence of different cytoplasmic signaling domains on CAR function. Conventional CARs generally share two main components: (i) the CD3 zeta cytoplasmic domain, which contains immunotyrosine activation motifs critical for T cell activation; and (ii) components of costimulatory receptors that trigger important survival pathways such as the Akt pathway. The first-generation CARs employed a single signaling domain from either CD3ζ or FcεRIγ.

Second-generation CARs combined the signaling domain of CD3 ζ with the cytoplasmic domain of costimulatory receptors from either the CD28 or TNFR family of receptors. Most CAR-engineered T cells that are currently being tested in the clinic employ second-generation CARs where CD3 ζ is coupled to the cytoplasmic domain of either CD28 or CD137. These second generation CARs have demonstrated anti-tumor activity in CD19-positive tumors. Third-generation CARs combined multiple costimulatory domains, but there is concern that third-generation CARs may lose antigen-specificity.

While CAR-engineered T cells have shown considerable promise in clinical application, they rely on a synthetic method for replacing the native activation signal that is provided by the T cell receptor (TCR). Since this synthetic receptor does not deliver all of the signaling components associated with the TCR (ex. ITAMs on CD3γ, CD3δ, CD3ε), it remains unclear whether the T cells are optimally activated by the CAR or how the CAR activation affects T cell differentiation (ex. progression to memory). Furthermore, since the CAR signaling domains are disconnected from their natural regulatory partners by the very nature of the CAR structure, there is also an inherent risk that CARs may lead to a low-level of constitutive activation, which could result in off-target toxicities. Therefore, the synthetic nature of the prototypic CAR may disrupt canonical mechanisms to limit TCR action and may underpin the severe toxicity often associated with therapeutic doses of conventional CAR T cells.

Given these limitations, it is preferable to re-direct T cells to attack tumors via their natural TCR. To this end, a class of recombinant proteins termed "Bispecific T-cell Engagers" (BiTEs) has been created. These proteins employ bispecific antibody fragments to crosslink T-cell TCR receptors with target antigens. This leads to efficient T-cell activation, triggering cytotoxicity. Similarly, bi-specific antibodies have been generated that accomplish this goal and some scientists have simply linked anti-CD3 antibodies to tumor-specific antibodies employing chemical linkage. While these bi-specific proteins have demonstrated some activity in vitro, GMP production, short biological half-lives and bioavailability represent significant challenges to the successful use of these molecules in cancer treatment. Additionally, these molecules also fail to properly recapitulate natural TCR signaling because they do not engage the TCR co-receptors (CD8 and CD4).

More recently, an alternate chimeric receptor, termed a Trifunctional T cell Antigen Coupler (Tri-TAC or TAC) receptor, has been developed which employs a distinct biology to direct the T cell to attack tumors. While the CAR is a fully synthetic receptor that stitches together components of T cell receptor (TCR) signaling complex, the TAC receptor re-directs the TCR towards tumor targets and recapitulates the native TCR signaling structure.

In view of the above, a need remains for chimeric receptors with enhanced activity and safety compared to traditional CARs and first generation TAC receptors.

Certain Terminology

The term "a cell" as used herein includes a single cell as well as a plurality of cells.

The term "T cell" as used herein refers to a type of lymphocyte that plays a central role in cell-mediated immunity. T cells, also referred to as T lymphocytes, can be distinguished from other lymphocytes, such as B cells and natural killer cells, by the presence of a T-cell receptor (TCR) on the cell surface. There are several subsets of T cells with distinct functions, including but not limited to, T helper cells, cytotoxic T cells, memory T cells, regulatory T cells and natural killer T cells.

The term "T cell antigen coupler" or TAC is used interchangeably with "trifunctional T cell antigen coupler" or Tri-TAC and refers to an engineered nucleic acid construct or polypeptide, that when expressed on a T cell, helps to facilitate the targeting of the T cell to a particular antigen.

The term "polynucleotide" and/or "nucleic acid sequence" and/or "nucleic acid" as used herein refers to a sequence of nucleoside or nucleotide monomers consisting of bases, sugars and intersugar (backbone) linkages. The term also includes modified or substituted sequences comprising non-naturally occurring monomers or portions thereof. The nucleic acid sequences of the present application may be deoxyribonucleic acid sequences (DNA) or ribonucleic acid sequences (RNA) and may include naturally occurring bases including adenine, guanine, cytosine, thymidine and uracil. The sequences may also contain modified bases. Examples of such modified bases include aza and deaza adenine, guanine, cytosine, thymidine and uracil; and xanthine and hypoxanthine. The nucleic acids of the present disclosure may be isolated from biological organisms, formed by laboratory methods of genetic recombination or obtained by chemical synthesis or other known protocols for creating nucleic acids.

The term "isolated polynucleotide" or "isolated nucleic acid sequence" as used herein refers to a nucleic acid substantially free of cellular material or culture medium when produced by recombinant DNA techniques, or chemical precursors, or other chemicals when chemically synthesized. An isolated nucleic acid is also substantially free of sequences which naturally flank the nucleic acid (i.e. sequences located at the 5' and 3' ends of the nucleic acid) from which the nucleic acid is derived. The term "nucleic acid" is intended to include DNA and RNA and can be either double stranded or single stranded, and represents the sense or antisense strand. Further, the term "nucleic acid" includes the complementary nucleic acid sequences.

The term "recombinant nucleic acid" or "engineered nucleic acid" as used herein refers to a nucleic acid or polynucleotide that is not found in a biological organism. For example, recombinant nucleic acids may be formed by laboratory methods of genetic recombination (such as molecular cloning) to create sequences that would not otherwise be found in nature. Recombinant nucleic acids may also be created by chemical synthesis or other known protocols for creating nucleic acids.

The term "polypeptide" or "protein" as used herein describes a chain of amino acids that correspond to those encoded by a nucleic acid. A polypeptide or protein of this disclosure can be a peptide, which usually describes a chain of amino acids of from two to about 30 amino acids. The term protein as used herein also describes a chain of amino acids having more than 30 amino acids and can be a fragment or domain of a protein or a full length protein. Furthermore, as used herein, the term protein can refer to a linear chain of amino acids or it can refer to a chain of amino acids that has been processed and folded into a functional protein. It is understood, however, that 30 is an arbitrary number with regard to distinguishing peptides and proteins and the terms can be used interchangeably for a chain of amino acids. The proteins of the present disclosure can be obtained by isolation and purification of the proteins from cells where they are produced naturally, by enzymatic (e.g., proteolytic) cleavage, and/or recombinantly by expression of nucleic acid encoding the proteins or fragments of this disclosure. The proteins and/or fragments of this disclosure can also be obtained by chemical synthesis or other known protocols for producing proteins and fragments.

The term "isolated polypeptide" refers to a polypeptide substantially free of cellular material or culture medium when produced by recombinant DNA techniques, or chemical precursors or other chemicals when chemically synthesized.

The term "antibody" as used herein is intended to include monoclonal antibodies, polyclonal antibodies, single chain antibodies, chimeric antibodies and antibody fusions. The antibody may be from recombinant sources and/or produced in transgenic animals. The term "antibody fragment" as used herein is intended to include without limitations Fab, Fab', F(ab')2, scFv, dsFv, ds-scFv, dimers, minibodies, diabodies, and multimers thereof, multispecific antibody fragments and Domain Antibodies.

The term "vector" as used herein refers to a polynucleotide that can be used to deliver a nucleic acid to the inside of a cell. In one embodiment, a vector is an expression vector comprising expression control sequences (for example, a promoter) operatively linked to a nucleic acid to be expressed in a cell. Vectors known in the art include, but are not limited to, plasmids, phages, cosmids and viruses.

The term "tumor antigen" or "tumor associated antigen" as used herein refers to an antigenic substance produced in tumor cells that triggers an immune response in a host (e.g. which can be represented by MHC complexes).

The term "T cell receptor" or TCR as used herein refers to a complex of integral membrane proteins that participates in the activation of T cells in response to the binding of an antigen. The TCR is a disulfide-linked membrane-anchored heterodimer normally consisting of the highly variable alpha ($\alpha$) and beta ($\beta$) chains expressed as part of a complex with the invariant CD3 (cluster of differentiation 3) chain molecules. T cells expressing this receptor are referred to as $\alpha$:$\beta$ (or $\alpha\beta$) T cells, though a minority of T cells express an alternate receptor, formed by variable gamma ($\gamma$) and delta ($\delta$) chains, referred as $\gamma\delta$ T cells. CD3 is a protein complex composed of four distinct chains. In mammals, the complex contains a CD3$\gamma$ chain, a CD3$\delta$ chain, two CD3$\epsilon$ chains and two CD3$\zeta$ chains.

As used herein, the term "transmembrane and cytoplasmic domain" refers to a polypeptide that may include, but is not limited to, protein domains that (a) associate with the lipid raft and/or (b) bind Lck. As used herein, "protein domain" refers to a conserved part of a given protein sequence structure that functions and exists independently of the rest of the protein chain.

A "TCR co-receptor" as used herein, refers to a molecule that assists the T cell receptor (TCR) in communicating with an antigen-presenting cell. Examples of TCR co-receptors include, but are not limited to, CD4, CD8, CD5, CD9, and CD22.

A "TCR co-stimulator" as used herein, refers to a molecule that enhances the response of a T cell to an antigen. Examples of TCR co-stimulators include, but are not limited to, ICOS, CD27, CD28, 4-1BB (CD 137), OX40 (CD134), CD30, CD40, lymphocyte fiction-associated antigen 1 (LFA-1), CD2, CD7, LIGHT, NKG2C, B7-H3, and a ligand that specifically binds CD83.

A "TCR co-inhibitor" as used herein, refers to a molecule that inhibits the response of a T cell to an antigen (also known as a checkpoint receptor). Examples of TCR co-stimulators include, but are not limited to, PD-1, TIM3, LAG-3, TIGIT, BTLA, CD160, and CD37.

The terms "recipient", "individual", "subject", "host", and "patient", are used interchangeably herein and in some cases, refer to any mammalian subject for whom diagnosis, treatment, or therapy is desired, particularly humans. "Mammal" for purposes of treatment refers to any animal classified as a mammal, including humans, domestic and farm animals, and laboratory, zoo, sports, or pet animals, such as dogs, horses, cats, cows, sheep, goats, pigs, mice, rats, rabbits, guinea pigs, monkeys etc. In some embodiments, the mammal is human.

As used herein, the terms "treatment," "treating," and the like, in some cases, refer to administering an agent, or carrying out a procedure, for the purposes of obtaining an effect. The effect may be prophylactic in terms of completely or partially preventing a disease or symptom thereof and/or may be therapeutic in terms of effecting a partial or complete cure for a disease and/or symptoms of the disease. "Treatment," as used herein, may include treatment of a disease or disorder (e.g. cancer) in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease; (b) inhibiting the disease, i.e., arresting its development; and (c) relieving the disease, i.e., causing regression of the disease. Treating may refer to any indicia of success in the treatment or amelioration or prevention of a cancer, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms is based on one or more objective or subjective parameters; including the results of an examination by a physician. Accordingly, the term "treating" includes the administration of the compounds or agents of the present invention to prevent or delay, to alleviate, or to arrest or inhibit development of the symptoms or conditions associated with diseases (e.g. cancer). The term "therapeutic effect" refers to the reduction, elimination, or prevention of the disease, symptoms of the disease, or side effects of the disease in the subject.

As used herein, singular forms "a", "and," and "the" include plural referents unless the context clearly indicates otherwise. Thus, for example, reference to "an antibody" includes a plurality of antibodies and reference to "an antibody" in some embodiments includes multiple antibodies, and so forth.

As used herein, all numerical values or numerical ranges include whole integers within or encompassing such ranges and fractions of the values or the integers within or encompassing ranges unless the context clearly indicates otherwise. Thus, for example, reference to a range of 90-100%, includes 91%, 92%, 93%, 94%, 95%, 95%, 97%, etc., as well as 91.1%, 91.2%, 91.3%, 91.4%, 91.5%, etc., 92.1%, 92.2%, 92.3%, 92.4%, 92.5%, etc., and so forth. In another example, reference to a range of 1-5,000 fold includes 1, 2, 3, 4, 5, 6, 7, 8, 9, 10, 11, 12, 13, 14, 15, 16, 17, 18, 19, 20, fold, etc., as well as 1.1, 1.2, 1.3, 1.4, 1.5, fold, etc., 2.1, 2.2, 2.3, 2.4, 2.5, fold, etc., and so forth.

"About" a number, as used herein, refers to range including the number and ranging from 10% below that number to 10% above that number. "About" a range refers to 10% below the lower limit of the range, spanning to 10% above the upper limit of the range.

Percent (%) identity" refers to the extent to which two sequences (nucleotide or amino acid) have the same residue at the same positions in an alignment. For example, "an amino acid sequence is X % identical to SEQ ID NO: Y" refers to % identity of the amino acid sequence to SEQ ID NO:Y and is elaborated as X % of residues in the amino acid sequence are identical to the residues of sequence disclosed in SEQ ID NO: Y. Generally, computer programs are employed for such calculations. Exemplary programs that compare and align pairs of sequences, include ALIGN (Myers and Miller, 1988), FASTA (Pearson and Lipman, 1988; Pearson, 1990) and gapped BLAST (Altschul et al., 1997), BLASTP, BLASTN, or GCG (Devereux et al., 1984).

As used herein, the term "selective binding" refers to the extent to which a protein (e.g. target-binding ligand of TAC) binds its target antigen (e.g. HER-2 or BCMA) rather than other antigens.

T Cell-Antigen Coupler (TAC)

Disclosed herein, in some embodiments, are nucleic acids encoding Trifunctional T cell-antigen coupler (Tri-TAC) that activate natural signaling through the T-cell receptor (TCR), while retaining MHC unrestricted targeting.

Disclosed herein, in some embodiments, are nucleic acid encoding a Trifunctional T cell-antigen coupler (Tri-TAC or TAC) comprising: (a) a first polynucleotide sequence encoding a ligand that selectively binds a target antigen; (b) a second polynucleotide sequence encoding a murine UCHT1 (muUCHT1) ligand with a Y182T mutation comprising an amino acid sequence having at least 70% sequence identity with SEQ ID NO: 26 that binds a protein associated with a T cell receptor (TCR) complex; and (c) a third polynucleotide sequence encoding a TCR signaling domain polypeptide. In some instances, the ligand specifically binds the target antigen. In some instances, the second polynucleotide sequence encoding a muUCHT1 ligand with a Y182T mutation comprises an amino acid sequence having at least 75% sequence identity with SEQ ID NO: 26. In some instances, the second polynucleotide sequence encoding a muUCHT1 ligand with a Y182T mutation comprises an amino acid sequence having at least 80% sequence identity with SEQ ID NO: 26. In some instances, the second polynucleotide sequence encoding a muUCHT1 ligand with a Y182T mutation comprises an amino acid sequence having at least 85% sequence identity with SEQ ID NO: 26. In some instances, the second polynucleotide sequence encoding a muUCHT1 ligand with a Y182T mutation comprises an amino acid sequence having at least 90% sequence identity with SEQ ID NO: 26. In some instances, the second polynucleotide sequence encoding a muUCHT1 ligand with a Y182T mutation comprises an amino acid sequence having at least 95% sequence identity with SEQ ID NO: 26. In some instances, the second polynucleotide sequence encoding a muUCHT1 ligand with a Y182T mutation comprises an amino acid sequence of SEQ ID NO: 26. In some instances, the percent sequence identity of the second polypeptide sequence encoding a muUCHT1 ligand with a Y182T mutation with SEQ ID NO: 26 refers to amino acids other than the Y182T mutation.

Disclosed herein, in some embodiments are nucleic acid encoding a Trifunctional T cell-antigen coupler (Tri-TAC or TAC) comprising: (a) a first polynucleotide sequence encoding a ligand that selectively binds a target antigen; (b) a second polynucleotide sequence encoding a humanized UCHT1 (huUCHT1) ligand comprising an amino acid sequence having at least 70% sequence identity with SEQ ID NO: 29 that binds a protein associated with a T cell receptor (TCR) complex; and (c) a third polynucleotide sequence encoding a TCR signaling domain polypeptide. In some instances, the ligand specifically binds the target antigen. In some instances, the second polynucleotide sequence encoding a huUCHT1 ligand comprises an amino acid sequence having at least 75% sequence identity with SEQ ID NO: 29. In some instances, the second polynucleotide sequence encoding a huUCHT1 ligand comprises an amino acid sequence having at least 80% sequence identity with SEQ ID NO: 29. In some instances, the second polynucleotide sequence encoding a huUCHT1 ligand comprises an amino acid sequence having at least 85% sequence identity with SEQ ID NO: 29. In some instances, the second polynucleotide sequence encoding a huUCHT1 ligand comprises an amino acid sequence having at least 90% sequence identity with SEQ ID NO: 29. In some instances, the second polynucleotide sequence encoding a huUCHT1 ligand comprises an amino acid sequence having at least 95% sequence identity with SEQ ID NO: 29. In some instances, the second polynucleotide sequence encoding a huUCHT1 ligand comprises an amino acid sequence of SEQ ID NO: 29.

Disclosed herein, in some embodiments are nucleic acid encoding a Trifunctional T cell-antigen coupler (Tri-TAC or TAC) comprising: (a) a first polynucleotide sequence encoding a ligand that selectively binds a target antigen; (b) a second polynucleotide sequence encoding a humanized UCHT1 (huUCHT1) ligand with a Y177T mutation comprising an amino acid sequence having at least 70% sequence identity with SEQ ID NO: 28 that binds a protein associated with a T cell receptor (TCR) complex; and (c) a third polynucleotide sequence encoding a TCR signaling domain polypeptide. In some instances, the ligand specifically binds the target antigen. In some instances, the second polynucleotide sequence encoding a huUCHT1 ligand with a Y177T mutation comprises an amino acid sequence having at least 75% sequence identity with SEQ ID NO: 28. In some instances, the second polynucleotide sequence encoding a huUCHT1 ligand with a Y177T mutation comprises an amino acid sequence having at least 80% sequence identity with SEQ ID NO: 28. In some instances, the second polynucleotide sequence encoding a huUCHT1 ligand with a Y177T mutation comprises an amino acid sequence having at least 85% sequence identity with SEQ ID NO: 28. In some instances, the second polynucleotide sequence encoding a huUCHT1 ligand with a Y177T mutation comprises an amino acid sequence having at least 90% sequence identity with SEQ ID NO: 28. In some instances, the second polynucleotide sequence encoding a huUCHT1 ligand with a Y177T mutation comprises an amino acid sequence having at least 95% sequence identity with SEQ ID NO: 28. In some instances, the second polynucleotide sequence encoding a huUCHT1 ligand with a Y177T mutation comprises an amino acid sequence of SEQ ID NO: 28. In some instances, the percent sequence identity of the second polypeptide sequence encoding a huUCHT1 ligand with a Y177T mutation with SEQ ID NO: 28 refers to amino acids other than the Y177T mutation.

In some embodiments, the ligand that selectively binds a target antigen (or a target-specific ligand) directs the T cell-antigen coupler (TAC) to a target cell. In some instances, the target-specific ligand is referred to as an antigen binding domain. In some instances, a target-specific ligand refers to any substance that binds, directly or indirectly, to a target cell. In some embodiments, the target specific ligand binds to an antigen (protein produced by a cell that can elicit an immune response) on the target cell. In some instances, the target-specific ligands include, but are not limited to, antibodies and fragments thereof, for example single chain antibodies such as single-chain antibodies (scFvs), single domain antibodies, peptides, peptidomimetics, proteins, glycoproteins, or proteoglycans that bind to the target cell and/or antigen. In some instances, the target-specific ligands include, but are not limited to, designed ankyrin repeat proteins (DARPins), lectins, knottins, centryrins, anticalins, or naturally occurring ligands for the tumor antigen, such as growth factors, enzyme substrates, receptors or binding proteins. In some instances, target specific ligands include non-protein compounds that bind to target cells and/or antigens, including but not limited to carbohydrates, lipids, nucleic acids, or small molecules. In some instances, a target-specific ligand is a designed ankyrin repeat (DARPin) targeted to a specific cell and/or antigen. In some instances, the target-specific ligand is a DARPin that selectively binds a HER-2 (erbB-2) antigen. In some instances, the target-specific ligand is a DARPin that specifically binds a HER-2 (erbB-2) antigen. In some instances, the DARPin targeted to HER-2 (erb-2) comprises SEQ ID NO: 7 and SEQ ID NO: 8. In some instances, the target-specific ligand is a single-chain antibody (scFv) targeted to a specific cell and/or antigen. In some instances, the target-specific ligand is a scFv that selectively binds BCMA. In some instances, the target-specific ligand is a scFv that specifically binds BCMA. In some instances, the scFv that binds BCMA comprises SEQ ID NO: 21 and SEQ ID NO: 22.

In some instances, a target cell is a cell associated with a disease state, including, but not limited to cancer. In some embodiments, a target cell is a tumor cell. In some instances, a target-specific ligand can bind to a tumor antigen or tumor associated antigen on a tumor cell. In some instances, the target antigen is a tumor antigen. In some instances, the tumor antigen when proteinaceous is a sequence of 8 or more amino acids up to the full protein. In some instances, the tumor antigen is any number of amino acids in between 8 and the full length protein which comprises at least one antigenic fragment of the full length protein that is represented in a MHC complex. Examples of tumor antigens include, but are not limited to, HER-2 (erbB-2), B-cell maturation antigen (BCMA), alphafetoprotein (AFP), carcinoembryonic antigen (CEA), CA-125, MUC-1, epithelial tumor antigen (ETA), tyrosinase, melanoma-associated antigen (MAGE), prostate-specific antigen (PSA), glioma-associated antigen, (3-human chorionic gonadotropin, thyroglobulin, RAGE-1, MN-CA IX, human telomerase reverse transcriptase, RU1, RU2 (AS), intestinal carboxyl esterase, mut hsp70-2, M-CSF, prostase, PAP, NY-ESO-1, LAGE-1a, p53, prostein, PSMA, survivin and telomerase, prostate-carcinoma tumor antigen-1 (PCTA-1), ELF2M, neutrophil elastase, CD22, insulin growth factor (IGF)-I, IGF-II, IGF-I receptor and mesothelin. In some instances, the tumor antigen is a HER-2 antigen. In some instances, the HER-2 specific ligand comprises an antigen binding domain of an antibody selected from Trastuzumab, Pertuzumab, Lapatinib, Neratinib, Ado-trastuzmab Emtansine, Gancotamab, Margetuximab, Timigutuzumab, and Ertumaxomab. In some instances, the tumor antigen is a BCMA antigen. In some instances, the BCMA specific ligand comprises an antigen binding domain of an antibody selected from Belantamab mafodotin, and GSK2857916.

In some embodiments, the TAC recruits the T-Cell Receptor (TCR) in combination with co-receptor stimulation. In some instances, the TAC comprises a ligand that binds a protein associated with the TCR complex. In some instances, the ligand that binds a protein associated with a TCR complex comprises a substance that binds, directly or indirectly, to a protein of the TCR. Proteins associated with the TCR include, but are not limited to, the TCR alpha (α) chain, TCR beta (β) chain, TCR gamma (γ) chain, TCR delta (δ) chain, CD3γ chain, CD3δ chain and CD3ε chains. In some embodiments, a ligand that binds a protein associated with the TCR complex is an antibody to the TCR alpha (α) chain, TCR beta (β) chain, TCR gamma (γ) chain, TCR delta (δ) chain, CD3γ chain, CD3δ chain and/or CD3ε chain. In some instances, the protein associated with a TCR complex is CD3. In some instances, the protein associated with a TCR complex is CD3ε. In some embodiments, the ligand is an antibody or a fragment thereof that binds CD3. Examples of CD3 antibodies, include, but are not limited to, for muromonab, otelixizumab, teplizumab and visilizumab. In some embodiments, the antibody that binds CD3 is a single chain antibody, for example a single-chain antibody (scFv). In some instances, the ligand that binds to a CD3 is UCHT1. In some instances, the UCHT1 ligand binds CD3ε. In some instances, the UCHT1 ligand is a murine ligand. In some instances, the murine UCHT1 ligand comprises SEQ ID NOs: 13 and 14. In some instances, the murine UCHT1 ligand binds CD3ε. In some instances, the murine UCHT1 ligand with a Y182T mutation binds CD3ε. In some instances, a humanized variant of UCHT1 ligand binds CD3ε. In some instances, the humanized UCHT1 ligand with a Y177T mutation binds CD3ε.

In some embodiments, the TCR signaling domain polypeptide comprises a transmembrane domain. In some embodiments, the TCR signaling domain polypeptide comprises a cytoplasmic domain. In some embodiments, the TCR signaling domain polypeptide comprises a transmembrane domain and a cytosolic domain. In some instances, the TCR signaling domain polypeptide comprises a transmembrane domain and/or a cytosolic domain of a TCR co-receptor. In some instances, the TCR co-receptor is CD4. In some instances, the TCR signaling domain polypeptide comprises the transmembrane and cytoplasmic domains of the CD4 co-receptor comprising SEQ ID NO: 17 and 18. In some instances, the TCR co-receptor is CD8. In some instances, the TCR co-receptor is CD8α. In some instances, the TCR co-receptor is CD5. In some instances, the TCR co-receptor is CD9. In some instances, the TCR co-receptor is CD5. In some instances, the TCR co-receptor is CD22. In some instances, the TCR signaling domain polypeptide comprises a transmembrane domain and/or a cytosolic domain of a TCR co-stimulator. In some instances, the TCR co-stimulator is ICOS. In some instances, the TCR co-stimulator is CD27. In some instances, the TCR co-stimulator is CD28. In some instances, the TCR co-stimulator is 4-1BB (CD137). In some instances, the TCR co-stimulator is OX40 (CD134). In some instances, the TCR co-stimulator is CD30. In some instances, the TCR co-stimulator is CD40. In some instances, the TCR co-stimulator is lymphocyte fiction-associated antigen 1 (LFA-1). In some instances, the TCR co-stimulator is CD2. In some instances, the TCR co-stimulator is CD7. In some instances, the TCR co-stimulator is LIGHT. In some instances, the TCR co-stimulator is NKG2C. In some instances, the TCR co-stimulator is B7-H3. In some instances, the TCR co-stimulator is a ligand that specifically binds CD83. In some instances, the TCR signaling domain polypeptide comprises a transmembrane domain and/or a cytosolic domain of a TCR co-inhibitor. In some instances, the TCR co-inhibitor is PD-1. In some instances, the TCR co-inhibitor is TIM3. In some instances, the TCR co-inhibitor is LAG-3. In some instances, the TCR co-inhibitor is TIGIT. In some instances, the TCR co-inhibitor is BTLA. In some instances, the TCR co-inhibitor is CD160. In some instances, the TCR co-inhibitor is CD37. In some embodiments, the TCR signaling domain polypeptide includes both a cytoplasmic domain and a transmembrane domain of a TCR co-receptor or co-stimulator protein. In some instances, the cytoplasmic domain and transmembrane domain are from the same co-receptor or co-stimulator or from different co-receptors or co-stimulators. In some instances, the cytoplasmic domain and transmembrane domains are optionally joined by a linker. In some embodiments, the TAC further comprises other polypeptides that directly or indirectly act to target or activate the T cell.

In some embodiments, the first polypeptide, the second polypeptide, and the third polypeptide are directly fused. In some embodiments, the first polypeptide, the second polypeptide, and the third polypeptide are joined by at least one linker. In some embodiments, the first polypeptide and the second polypeptide are directly fused, and joined to the third polypeptide by a linker. In some embodiments, the second polypeptide and the third polypeptide are directly fused, and joined to the first polypeptide by a linker. In some embodiments, the linker is a peptide linker. In some embodiments, the peptide linker comprises 1 to 40 amino acids. In some embodiments, the peptide linker comprises 1 to 30 amino acids. In some embodiments, the peptide linker comprises 1 to 15 amino acids. In some embodiments, the peptide linker comprises 1 to 10 amino acids. In some embodiments, the peptide linker comprises 1 to 6 amino acids. In some embodiments, the peptide linker comprises 30 to 40 amino acids. In some embodiments, the peptide linker comprises 32 to 36 amino acids. In some embodiments, the peptide linker comprises 5 to 30 amino acids. In some embodiments, the peptide linker comprises 5 amino acids. In some embodiments, the peptide linker comprises 10 amino acids. In some embodiments, the peptide linker comprises 15 amino acids. In some embodiments, the peptide linker comprises 20 amino acids. In some embodiments, the peptide linker comprises 25 amino acids. In some embodiments, the peptide linker comprises 30 amino acids. In some embodiments, the peptide linker comprises a G4S3 linker. Other examples of linkers that, in some instances, are used in the TAC, are peptides corresponding to SEQ ID NOs: 11, 12, 15, 16, 19 and 20 and variants and fragments thereof.

In some embodiments, the transmembrane and cytoplasmic domains of the CD4 co-receptor are fused to single-chain antibody that binds CD3. In some instances, a designed ankyrin repeat (DARPin) is linked to the CD4-UCHT1 chimera to generate a Trifunctional T cell-antigen coupler (Tri-TAC). In some instances, the Tri-TAC draws the CD3 molecule and the TCR into regions of lipid rafts and brings Lck into the proximity of the TCR, similar to natural MHC binding.

In some instances, T cells engineered with the Tri-TAC demonstrate functionality equivalent to a conventional CAR in vitro. In some instances, T cells engineered with the Tri-TAC demonstrate functionality superior to a conventional CAR in vitro. In some instances, the Tri-TAC offers enhanced safety compared to traditional CARs as no activation domains are part of the protein.

In some embodiments, the nucleic acid is a recombinant, or engineered, nucleic acid. In some embodiments, the first, second and/or third polynucleotides are recombinant, or engineered, polynucleotides. In some embodiments, the polynucleotides described herein may be modified or mutated to optimize the function of the encoded polypeptide and/or the function, activity and/or expression of the T cell antigen coupler.

In some embodiments, the UCHT1 mutants are generated that have enhanced surface expression of the TAC (FIGS. 8, 9, 10, 12). In some instances, the TAC comprises a modified or mutated ligand that binds the TCR complex, wherein the TAC comprising the modified or mutated antibody has increased surface expression and/or activity compared to a TAC comprising a wild type, or non-modified or mutated ligand that binds the TCR complex. An example of a mutant or modified antibody that binds CD3 is the UCHT1(Y182T) mutant disclosed herein (SEQ ID NO: 25 and 26).

The Tri-TAC is contemplated to be present in various configurations. In some embodiments, the target specific ligand and the T cell receptor signaling domain polypeptide are both fused to the ligand that binds the TCR complex. For example, the anti-HER-2 DARPin Tri-TAC disclosed herein (also referred to as configuration 1; SEQ ID NO: 1 and 2) includes, in order:
  i) the anti-HER-2 Tri-TAC leader sequence (secretion signal) (SEQ ID NO: 5 and 6)
  ii) DARPin specific for HER-2 antigen (SEQ ID NO: 7 and 8)
  iii) Myc tag (SEQ ID NO: 9 and 10)
  iv) Linker 1 (SEQ ID NO: 11 and 12)
  v) UCHT1 (SEQ ID NO: 13 and 14)

vi) Linker 2 (SEQ ID NO: 15 and 16)
vii) CD4 (SEQ ID NO: 17 and 18).

In some embodiments, the DARPin is replaced with a scFv specific for a BCMA antigen (SEQ ID NO: 21 and 22).

Polypeptides and Vector Constructs

Disclosed herein, in some embodiments, are polypeptides encoded by the nucleic acid sequence as disclosed herein. Also disclosed herein, are vectors comprising the nucleic acid sequence as disclosed herein. In some instances, the vectors further comprise a promoter. In some instances, the promoter is functional in a mammalian cell. A variety of delivery vectors and expression vehicles are employed to introduce nucleic acids described herein into a cell.

Promoters, regions of DNA that initiate transcription of a particular nucleic acid sequence, are well known in the art. A "promoter functional in a mammalian cell" refers to a promoter that drives expression of the associated nucleic acid sequence in a mammalian cell. A promoter that drives expression of a nucleic acid sequence may be referred to as being "operably connected" to the nucleic acid sequence.

In some embodiments, the first polynucleotide and third polynucleotide are fused to the second polynucleotide to provide a Tri-TAC fusion and the coding sequence of the Tri-TAC fusion is operably connected to the promoter. In some embodiments, the second polynucleotide and third polynucleotide are fused to the first polynucleotide to provide a Tri-TAC fusion and the coding sequence of the Tri-TAC fusion is operably connected to the promoter. In some embodiments, the vector is designed for expression in mammalian cells such as T cells. In some embodiments, the vector is a viral vector. In some instances, the viral vector is a retroviral vector.

Vectors that are useful comprise vectors derived from lentiviruses, Murine Stem Cell Viruses (MSCV), pox viruses, oncoretroviruses, adenoviruses, and adeno-associated viruses. Other delivery vectors that are useful comprise vectors derived from herpes simplex viruses, transposons, vaccinia viruses, human papilloma virus, Simian immunodeficiency viruses, HTLV, human foamy virus and variants thereof. Further vectors that are useful comprise vectors derived from spumaviruses, mammalian type B retroviruses, mammalian type C retroviruses, avian type C retroviruses, mammalian type D retroviruses and HTLV/BLV type retroviruses. One example of a lentiviral vector useful in the disclosed compositions and methods is the pCCL vector.

Many modifications may be made to the polynucleotide sequences including vector sequences and polypeptides sequences disclosed herein. Modifications include substitution, insertion or deletion of nucleotides or amino acids or altering the relative positions or order of nucleotides or amino acids.

Sequence Identity

The polynucleotides disclosed herein also include nucleic acid molecules (or a fragment thereof) having at least about: 70% identity, at least 80% identity, at least 90% identity, at least 95% identity, at least 96% identity, at least 97% identity, at least 98% identity or, at least 99% or 99.5% identity to a nucleic acid molecule disclosed. The polypeptides also include polypeptides (or a fragment thereof) having at least about: 70% identity, at least 80% identity, at least 90% identity, at least 95% identity, at least 96% identity, at least 97% identity, at least 98% identity or, at least 99% or 99.5% identity to a polypeptide disclosed.

Sequence identity is preferably set at least about: 70% identity, at least 80% identity, at least 90% identity, at least 95% identity, at least 96% identity, at least 97% identity, at least 98% identity or, most preferred, at least 99% or 99.5% identity to the nucleotide sequences provided herein and/or its complementary sequence. Sequence identity is also preferably set at least about: 70% identity, at least 80% identity, at least 90% identity, at least 95% identity, at least 96% identity, at least 97% identity, at least 98% identity or, most preferred, at least 99% or 99.5% identity to the polypeptide sequences provided herein.

Hybridization

Disclosed herein, in some instances, is DNA that has a sequence with sufficient identity to a nucleic acid molecule described herein to hybridize under stringent hybridization conditions. Also disclosed herein are nucleic acid molecules that hybridize to one or more of the sequences described herein and/or its complementary sequence. Such nucleic acid molecules preferably hybridize under high stringency conditions. High stringency washes have preferably have low salt (preferably about 0.2% SSC) and a temperature of about 50-65° C. and are optionally conducted for about 15 minutes.

Expression in T Cells

The Trifunctional T cell antigen coupler is designed for expression in T cells. Disclosed herein, in some embodiments, are engineered T cells comprising the nucleic acid sequences disclosed herein, or the vectors disclosed herein. In some instances, the T cell expresses a Trifunctional T cell antigen coupler (Tri-TAC) disclosed herein. Further disclosed herein, are T cells transduced or transfected with T cell antigen coupler or a vector comprising a Tri-TAC. In some instances, the T cell is an isolated T cell.

T cells can be obtained from a number of sources, including, but not limited to blood (for example, peripheral blood mononuclear cells), bone marrow, thymus tissue, lymph node tissue, cord blood, thymus tissue, tissue from an infection site, spleen tissue, and tumors. In some embodiments, the T cells are autologous T cells. In some embodiments, the T cells are obtained from a cell line of T cells. In some embodiments, the T cells are obtained from donors (allogeneic T cells). In some embodiments, the T cells are obtained by differentiation of embryonic or adult stem cells or from induced pluripotent stem cells. In some embodiments, regardless of the source of T cells, the T cells have been modified so that they lack expression of an endogenous TCR and/or permanently or transiently lack expression of MHC/HLA molecules (universal donor T cells). In some embodiments, the T cells can be autologous with respect to the subject. In some embodiments, the cells are allogeneic, syngeneic or xenogeneic with respect to the subject.

Once obtained, the T cells are optionally enriched in vitro. In some instances, a population of cells is enriched by positive or negative selection. Further, the T cells are optionally frozen or cryopreserved and then thawed at a later date.

Before or after introducing the Tri-TAC to the T cells, the T cells, in some instances, are activated and/or expanded. In some instances, the T cells are expanded by contact with a surface having attached thereto an agent that stimulates a CD3/TCR complex associated signal and a ligand that stimulates a co-stimulator molecule on the surface of the T cells.

In some embodiments, the T cells are transduced or transfected with nucleic acid sequences. In some instances, the transduced or transfected T cells are expressed. In some instances, a nucleic acid can be introduced into a cell by physical, chemical or biological means. Physical means include, but are not limited to, microinjection, electroporation, particle bombardment, lipofection and calcium phosphate precipitation. Biological means include the use of DNA and RNA vectors.

In some embodiments, viral vectors, including retroviral vectors, are used to introduce and express a nucleic acid into a T cell. Viral vectors include vectors derived from lentivirus, Murine Stem Cell Viruses (MSCV), pox viruses, herpes simplex virus I, adenovirus and adeno-associated viruses. The vector optionally includes a promoter that drives expression of the transduced nucleic acid molecule in a T cell.

Various assays are used to confirm the presence and/or expression of the transduced nucleic acid sequence and/or the polypeptide encoded by the nucleic acid in the T cell. Assays include, but are not limited to, Southern and Northern blotting, RT-PCR and PCR, ELISAs and Western blotting.

In some embodiments, a T cell expressing a T cell antigen coupler has increased T cell activation in the presence of an antigen compared to a T cell not expressing a T cell antigen coupler and/or as compared to a T cell expressing a traditional CAR. Increased T cell activation can be ascertained by numerous methods, including but not limited to, increased tumor cell line killing, increased cytokine production, increased cytolysis, increased degranulation and/or increased expression of activation markers such as CD107α, IFNγ, IL2 or TNFα. Increases may be measured in an individual cell or in a population of cells.

The terms "increased" or "increasing" as used herein refer to at least a 1%, 2%, 5%, 10%, 25%, 50%, 100% or 200% increase in a T cell or population of T cells expressing a T cell antigen coupler compared to a T cell or population of T cells not expressing a T cell antigen coupler and/or as compared to a T cell or population of T cells expressing a traditional CAR.

Pharmaceutical Compositions

Disclosed herein, in some embodiments, are pharmaceutical composition comprising engineered T cells disclosed herein (transduced with and/or expressing a T cell antigen coupler), and a pharmaceutically acceptable carrier. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. In some instances, the engineered T cells are formulated for intravenous administration.

Pharmaceutical compositions are administered in a manner appropriate to the disease to be treated (or prevented). The quantity and frequency of administration is determined by such factors as the condition of the patient, and the type and severity of the patient's disease, although appropriate dosages are determined by clinical trials. When "an immunologically effective amount," "an anti-tumor effective amount," "a tumor-inhibiting effective amount," or "therapeutic amount" is indicated, the precise amount of the compositions of the present invention to be administered can be determined by a physician with consideration of individual differences in age, weight, tumor size, extent of infection or metastasis, and condition of the patient (subject). For example, the modified T cells and/or pharmaceutical compositions described herein are administered at a dosage of $10^4$ to $10^9$ cells per kg body weight, optionally $10^5$ to $10^8$ cells per kg body weight, $10^6$ to $10^7$ cells per kg body weight or $10^5$ to $10^6$ cells per kg body weight, including all integer values within those ranges. T cell compositions may also be administered multiple times at these dosages. The dosage can be administered a single time or multiple times, for example daily, weekly, biweekly, or monthly, or can be administered upon recurrence, relapse or progression of the cancer being treated. The cells can be administered by using infusion techniques that are commonly known in immunotherapy (see, e.g., Rosenberg et al., New Eng. J. of Med. 319:1676, 1988).

In some embodiments, the pharmaceutical composition is substantially free of, e.g., there are no detectable levels of a contaminant, e.g., selected from the group consisting of endotoxin, mycoplasma, replication competent lentivirus (RCL), p24, VSV-G nucleic acid, HIV gag, residual anti-CD3/anti-CD28 coated beads, mouse antibodies, pooled human serum, bovine serum albumin, bovine serum, culture media components, vector packaging cell or plasmid components, a bacterium and a fungus. In one embodiment, the bacterium is at least one selected from the group consisting of *Alcaligenes faecalis, Candida albicans, Escherichia coli, Haemophilus influenza, Neisseria meningitides, Pseudomonas aeruginosa, Staphylococcus aureus, Streptococcus pneumonia*, and *Streptococcus pyogenes* group A.

In some embodiments, it may be desired to administer engineered T-cells to a subject and then subsequently redraw blood (or have an apheresis performed), activate T-cells therefrom, and reinfuse the patient with these activated and expanded T-cells. This process can be carried out multiple times every few weeks. In some aspects, T-cells can be activated from blood draws of from 10 cc to 400 cc. In certain aspects, T-cells are activated from blood draws of 20 cc, 30 cc, 40 cc, 50 cc, 60 cc, 70 cc, 80 cc, 90 cc, or 100 cc.

The modified T cells and/or pharmaceutical compositions may be administered by methods including, but not limited to, aerosol inhalation, injection, ingestion, transfusion, implantation or transplantation. The modified T cells and/or pharmaceutical compositions may administered to a subject transarterially, subcutaneously, intradermally, intratumorally, intranodally, intramedullary, intramuscularly, by intravenous (i.v.) injection, or intraperitoneally. In one aspect, the modified T cells and/or pharmaceutical compositions thereof are administered to a patient by intradermal or subcutaneous injection. In some aspects, the modified T cells and/or pharmaceutical compositions thereof are administered by i.v. injection. The modified T cells and/or pharmaceutical compositions thereof may be injected directly into a tumor, lymph node, or site of infection.

A pharmaceutical composition can be prepared by per se known methods for the preparation of pharmaceutically acceptable compositions that can be administered to subjects, such that an effective quantity of the T cells are combined in a mixture with a pharmaceutically acceptable carrier. Suitable carriers are described, for example, in Remington's Pharmaceutical Sciences (Remington's Pharmaceutical Sciences, 20$^{th}$ ed., Mack Publishing Company, Easton, Pa., USA, 2000). On this basis, the compositions include, albeit not exclusively, solutions of the substances in association with one or more pharmaceutically acceptable carriers or diluents, and contained in buffered solutions with a suitable pH and iso-osmotic with the physiological fluids.

Suitable pharmaceutically acceptable carriers include essentially chemically inert and nontoxic compositions that do not interfere with the effectiveness of the biological activity of the pharmaceutical composition. Examples of suitable pharmaceutical carriers include, but are not limited to, water, saline solutions, glycerol solutions, N-(1(2,3-dioleyloxy)propyl)N,N,N-trimethylammonium chloride (DOTMA), dioleysylphosphotidyl-ethanolamine (DOPE), and liposomes. Such compositions should contain a therapeutically effective amount of the compound, together with a suitable amount of carrier so as to provide the form for direct administration to the patient.

Pharmaceutical compositions may also include, without limitation, lyophilized powders or aqueous or non-aqueous sterile injectable solutions or suspensions, which may further contain antioxidants, buffers, bacteriostats and solutes that render the compositions substantially compatible with the tissues or the blood of an intended recipient. Other components that may be present in such compositions include water, surfactants (such as Tween), alcohols, polyols, glycerin and vegetable oils, for example. Extemporaneous injection solutions and suspensions may be prepared from sterile powders, granules, tablets, or concentrated solutions or suspensions.

Methods of Treatment and Use

Disclosed herein, in some embodiments, are methods of treating a cancer expressing a target antigen in an individual in need thereof, comprising administering to the individual engineered T cells disclosed herein. Further disclosed herein is use of an engineered T cell disclosed herein in the preparation of a medicament to treat cancer in an individual in need thereof. Also disclosed herein is an engineered T cell disclosed herein for use in the treatment of cancer in an individual in need thereof. Also disclosed herein is the use of a mixture of T cells comprising modified and unmodified cells, or comprising different populations of modified cells with or without unmodified cells. One of ordinary skill in the art would understand that a therapeutic quantity of modified T cells need not be homogenous in nature.

Disclosed herein, in some embodiments, are methods of treating a cancer expressing a target antigen in an individual in need thereof, comprising administering to the individual an engineered T cell comprising a nucleic acid sequence encoding a T cell-antigen coupler (Tri-TAC) comprising: (a) a first polynucleotide sequence encoding a ligand that selectively binds a target antigen; (b) a second polynucleotide sequence encoding a murine UCHT1 (muUCHT1) ligand with a Y182T mutation comprising an amino acid sequence having at least 70% sequence identity with SEQ ID NO: 26 that binds a protein associated with a T cell receptor (TCR) complex; and (c) a third polynucleotide sequence encoding a TCR signaling domain polypeptide. In some instances, the ligand specifically binds the target antigen. In some instances, the second polynucleotide sequence encoding a muUCHT1 ligand with a Y182T mutation comprises an amino acid sequence having at least 75% sequence identity with SEQ ID NO: 26. In some instances, the second polynucleotide sequence encoding a muUCHT1 ligand with a Y182T mutation comprises an amino acid sequence having at least 80% sequence identity with SEQ ID NO: 26. In some instances, the second polynucleotide sequence encoding a muUCHT1 ligand with a Y182T mutation comprises an amino acid sequence having at least 85% sequence identity with SEQ ID NO: 26. In some instances, the second polynucleotide sequence encoding a muUCHT1 ligand with a Y182T mutation comprises an amino acid sequence having at least 90% sequence identity with SEQ ID NO: 26. In some instances, the second polynucleotide sequence encoding a muUCHT1 ligand with a Y182T mutation comprises an amino acid sequence having at least 95% sequence identity with SEQ ID NO: 26. In some instances, the second polynucleotide sequence encoding a muUCHT1 ligand with a Y182T mutation comprises an amino acid sequence of SEQ ID NO: 26. In some instances, the percent sequence identity of the second polypeptide sequence encoding a muUCHT1 ligand with a Y182T mutation with SEQ ID NO: 26 refers to amino acids other than the Y182T mutation.

Disclosed herein, in some embodiments, are methods of treating a cancer expressing a target antigen in an individual in need thereof, comprising administering to the individual an engineered T cell comprising a nucleic acid sequence encoding a T cell-antigen coupler (Tri-TAC) comprising: (a) a first polynucleotide sequence encoding a ligand that selectively binds a target antigen; (b) a second polynucleotide sequence encoding a humanized UCHT1 (huUCHT1) ligand comprising an amino acid sequence having at least 70% sequence identity with SEQ ID NO: 29 that binds a protein associated with a T cell receptor (TCR) complex; and (c) a third polynucleotide sequence encoding a TCR signaling domain polypeptide. In some instances, the ligand specifically binds the target antigen. In some instances, the second polynucleotide sequence encoding a huUCHT1 ligand comprises an amino acid sequence having at least 75% sequence identity with SEQ ID NO: 29. In some instances, the second polynucleotide sequence encoding a huUCHT1 ligand comprises an amino acid sequence having at least 80% sequence identity with SEQ ID NO: 29. In some instances, the second polynucleotide sequence encoding a huUCHT1 ligand comprises an amino acid sequence having at least 85% sequence identity with SEQ ID NO: 29. In some instances, the second polynucleotide sequence encoding a huUCHT1 ligand comprises an amino acid sequence having at least 90% sequence identity with SEQ ID NO: 29. In some instances, the second polynucleotide sequence encoding a huUCHT1 ligand comprises an amino acid sequence having at least 95% sequence identity with SEQ ID NO: 29. In some instances, the second polynucleotide sequence encoding a huUCHT1 ligand comprises an amino acid sequence of SEQ ID NO: 29.

Disclosed herein, in some embodiments, are methods of treating a cancer expressing a target antigen in an individual in need thereof, comprising administering to the individual an engineered T cell comprising a nucleic acid sequence encoding a T cell-antigen coupler (Tri-TAC) comprising: (a) a first polynucleotide sequence encoding a ligand that selectively binds a target antigen; (b) a second polynucleotide sequence encoding a humanized UCHT1 (huUCHT1) ligand with a Y177T mutation comprising an amino acid sequence having at least 70% sequence identity with SEQ ID NO: 28 that binds a protein associated with a T cell receptor (TCR) complex; and (c) a third polynucleotide sequence encoding a TCR signaling domain polypeptide. In some instances, the ligand specifically binds the target antigen. In some instances, the second polynucleotide sequence encoding a huUCHT1 ligand with a Y177T mutation comprises an amino acid sequence having at least 75% sequence identity with SEQ ID NO: 28. In some instances, the second polynucleotide sequence encoding a huUCHT1 ligand with a Y177T mutation comprises an amino acid sequence having at least 80% sequence identity with SEQ ID NO: 28. In some instances, the second polynucleotide sequence encoding a huUCHT1 ligand with a Y177T mutation comprises an amino acid sequence having at least 85% sequence identity with SEQ ID NO: 28. In some instances, the second polynucleotide sequence encoding a huUCHT1 ligand with a Y177T mutation comprises an amino acid sequence having at least 90% sequence identity with SEQ ID NO: 28. In some instances, the second polynucleotide sequence encoding a huUCHT1 ligand with a Y177T mutation comprises an amino acid sequence having at least 95% sequence identity with SEQ ID NO: 28. In some instances, the second polynucleotide sequence encoding a huUCHT1 ligand with a Y177T mutation comprises an amino acid sequence of SEQ ID NO: 28. In some instances, the percent sequence identity of the second polypeptide sequence encoding a huUCHT1 ligand with a Y177T mutation with SEQ ID NO: 28 refers to amino acids other than the Y177T mutation.

In some embodiments, the ligand that selectively binds a target antigen (or a target-specific ligand) directs the T cell-antigen coupler (Tri-TAC) to a target cell. In some instances, the target-specific ligand is referred to as an antigen binding domain. In some instances, a target-specific ligand refers to any substance that binds, directly or indirectly, to a target cell. In some embodiments, the target specific ligand binds to an antigen (protein produced by a cell that can elicit an immune response) on the target cell. In some instances, the target-specific ligands include, but are not limited to, antibodies and fragments thereof, for example single chain antibodies such as single-chain antibodies (scFvs), single domain antibodies, peptides, peptidomimetics, proteins, glycoproteins, or proteoglycans that bind to the target cell and/or antigen. In some instances, the target-specific ligands include, but are not limited to, designed ankyrin repeat proteins (DARPins), lectins, knottins, centryrins, anticalins, or naturally occurring ligands for the tumor antigen, such as growth factors, enzyme substrates, receptors or binding proteins. In some instances, target specific ligands include non-protein compounds that bind to target cells and/or antigens, including but not limited to carbohydrates, lipids, nucleic acids, or small molecules. In some instances, a target-specific ligand is a designed ankyrin repeat (DARPin) targeted to a specific cell and/or antigen. In some instances, the target-specific ligand is a DARPin that selectively binds a HER-2 (erbB-2) antigen. In some instances, the target-specific ligand is a DARPin that specifically binds a HER-2 (erbB-2) antigen. In some instances, the DARPin targeted to HER-2 (erb-2) comprises SEQ ID NO: 7 and SEQ ID NO: 8. In some instances, the target-specific ligand is a single-chain antibody (scFv) targeted to a specific cell and/or antigen. In some instances, the target-specific ligand is a scFv that selectively binds BCMA. In some instances, the target-specific ligand is a scFv that specifically binds BCMA. In some instances, the scFv that binds BCMA comprises SEQ ID NO: 21 and SEQ ID NO: 22.

In some instances, a target cell is a cell associated with a disease state, including, but not limited to cancer. In some embodiments, a target cell is a tumor cell. In some instances, a target-specific ligand can bind to a tumor antigen or tumor associated antigen on a tumor cell. In some instances, the target antigen is a tumor antigen. In some instances, the tumor antigen when proteinaceous is a sequence of 8 or more amino acids up to the full protein. In some instances, the tumor antigen is any number of amino acids in between 8 and the full length protein which comprises at least one antigenic fragment of the full length protein that is represented in a MHC complex. Examples of tumor antigens include, but are not limited to, HER-2 (erbB-2), B-cell maturation antigen (BCMA), alphafetoprotein (AFP), carcinoembryonic antigen (CEA), CA-125, MUC-1, epithelial tumor antigen (ETA), tyrosinase, melanoma-associated antigen (MAGE), prostate-specific antigen (PSA), glioma-associated antigen, (3-human chorionic gonadotropin, thyroglobulin, RAGE-1, MN-CA IX, human telomerase reverse transcriptase, RU1, RU2 (AS), intestinal carboxyl esterase, mut hsp70-2, M-CSF, prostase, PAP, NY-ESO-1, LAGE-1a, p53, prostein, PSMA, survivin and telomerase, prostate-carcinoma tumor antigen-1 (PCTA-1), ELF2M, neutrophil elastase, CD22, insulin growth factor (IGF)-I, IGF-II, IGF-I receptor and mesothelin. In some instances, the tumor antigen is a HER-2 antigen. In some instances, the HER-2 specific ligand comprises an antigen binding domain of an antibody selected from Trastuzumab, Pertuzumab, Lapatinib, Neratinib, Ado-trastuzmab Emtansine, Gancotamab, Margetuximab, Timigutuzumab, and Ertumaxomab. In some instances, the tumor antigen is a BCMA antigen. In some instances, the BCMA specific ligand comprises an antigen binding domain of an antibody selected from Belantamab mafodotin, and GSK2857916.

In some embodiments, the Tri-TAC recruits the T-Cell Receptor (TCR) in combination with co-receptor stimulation. In some instances, the TAC comprises a ligand that binds a protein associated with the TCR complex. In some instances, the ligand that binds a protein associated with a TCR complex comprises a substance that binds, directly or indirectly, to a protein of the TCR. Proteins associated with the TCR include, but are not limited to, the TCR alpha (α) chain, TCR beta (β) chain, TCR gamma (γ) chain, TCR delta (δ) chain, CD3γ chain, CD3δ chain and CD3ε chains. In some embodiments, a ligand that binds a protein associated with the TCR complex is an antibody to the TCR alpha (α) chain, TCR beta (I) chain, TCR gamma (γ) chain, TCR delta (δ) chain, CD3γ chain, CD3δ chain and/or CD3ε chain. In some instances, the protein associated with a TCR complex is CD3. In some instances, the protein associated with a TCR complex is CD3ε. In some embodiments, the ligand is an antibody or a fragment thereof that binds CD3. Examples of CD3 antibodies, include, but are not limited to, for muromonab, otelixizumab, teplizumab and visilizumab. In some embodiments, the antibody that binds CD3 is a single chain antibody, for example a single-chain antibody (scFv). In some instances, the ligand that binds to a CD3 is UCHT1. In some instances, the UCHT1 ligand binds CD3ε. In some instances, the UCHT1 ligand is a murine ligand. In some instances, the murine UCHT1 ligand comprises SEQ ID NOs: 13 and 14. In some instances, the murine UCHT1 ligand binds CD3ε. In some instances, the murine UCHT1 ligand with a Y182T mutation binds CD3ε. In some instances, the humanized UCHT1 ligand binds CD3ε. In some instances, the humanized UCHT1 ligand with a Y177T mutation binds CD3ε.

In some embodiments, the TCR signaling domain polypeptide comprises a transmembrane domain. In some embodiments, the TCR signaling domain polypeptide comprises a cytoplasmic domain. In some embodiments, the TCR signaling domain polypeptide comprises a transmembrane domain and a cytosolic domain. In some instances, the TCR signaling domain polypeptide comprises a transmembrane domain and/or a cytosolic domain of a TCR co-receptor. In some instances, the TCR co-receptor is CD4. In some instances, the TCR signaling domain polypeptide comprises the transmembrane and cytoplasmic domains of the CD4 co-receptor comprising SEQ ID NO: 17 and 18. In some instances, the TCR co-receptor is CD8. In some instances, the TCR co-receptor is CD8α. In some instances, the TCR co-receptor is CD5. In some instances, the TCR co-receptor is CD9. In some instances, the TCR co-receptor is CD5. In some instances, the TCR co-receptor is CD22. In some instances, the TCR signaling domain polypeptide comprises a transmembrane domain and/or a cytosolic domain of a TCR co-stimulator. In some instances, the TCR co-stimulator is ICOS. In some instances, the TCR co-stimulator is CD27. In some instances, the TCR co-stimulator is CD28. In some instances, the TCR co-stimulator is 4-1BB (CD137). In some instances, the TCR co-stimulator is OX40 (CD134). In some instances, the TCR co-stimulator is CD30. In some instances, the TCR co-stimulator is CD40. In some instances, the TCR co-stimulator is lymphocyte fiction-associated antigen 1 (LFA-1). In some instances, the TCR co-stimulator is CD2. In some instances, the TCR co-stimulator is CD7. In some instances, the TCR co-stimulator is LIGHT. In some instances, the TCR co-stimulator is NKG2C. In some instances, the TCR co-stimulator is B7-H3. In some instances, the TCR co-stimulator is a ligand that specifically binds CD83. In some instances, the TCR signaling domain polypeptide comprises a transmembrane domain and/or a cytosolic domain of a TCR co-inhibitor. In some instances, the TCR co-inhibitor is PD-1. In some instances, the TCR co-inhibitor is TIM3. In some instances, the TCR co-inhibitor is LAG-3. In some instances, the TCR co-inhibitor is TIGIT. In some instances, the TCR co-inhibitor is BTLA. In some instances, the TCR co-inhibitor is CD160. In some instances, the TCR co-inhibitor is CD37. In some embodiments, the TCR signaling domain polypeptide includes both a cytoplasmic domain and a transmembrane domain of a TCR co-receptor or co-stimulator protein. In some instances, the cytoplasmic domain and transmembrane domain are from the same co-receptor or co-stimulator or from different co-receptors or co-stimulators. In some instances, the cytoplasmic domain and transmembrane domains are optionally joined by a linker. In some embodiments, the TAC further comprises other polypeptides that directly or indirectly act to target or activate the T cell.

In some embodiments, the first polypeptide, the second polypeptide, and the third polypeptide are directly fused. In some embodiments, the first polypeptide, the second polypeptide, and the third polypeptide are joined by at least one linker. In some embodiments, the first polypeptide and the second polypeptide are directly fused, and joined to the third polypeptide by a linker. In some embodiments, the second polypeptide and the third polypeptide are directly fused, and joined to the first polypeptide by a linker. In some embodiments, the linker is a peptide linker. In some embodiments, the peptide linker comprises 1 to 40 amino acids. In some embodiments, the peptide linker comprises 1 to 30 amino acids. In some embodiments, the peptide linker comprises 1 to 15 amino acids. In some embodiments, the peptide linker comprises 1 to 10 amino acids. In some embodiments, the peptide linker comprises 1 to 6 amino acids. In some embodiments, the peptide linker comprises 30 to 40 amino acids. In some embodiments, the peptide linker comprises 32 to 36 amino acids. In some embodiments, the peptide linker comprises 5 to 30 amino acids. In some embodiments, the peptide linker comprises 5 amino acids. In some embodiments, the peptide linker comprises 10 amino acids. In some embodiments, the peptide linker comprises 15 amino acids. In some embodiments, the peptide linker comprises 20 amino acids. In some embodiments, the peptide linker comprises 25 amino acids. In some embodiments, the peptide linker comprises 30 amino acids. In some embodiments, the peptide linker comprises a G4S3 linker. Other examples of linkers that, in some instances, are used in the Tri-TAC, are peptides corresponding to SEQ ID NOs: 11, 12, 15, 16, 19 and 20 and variants and fragments thereof.

In some embodiments, the transmembrane and cytoplasmic domains of the CD4 co-receptor are fused to single-chain antibody that binds CD3. In some instances, a designed ankyrin repeat (DARPin) is linked to the CD4-UCHT1 chimera to generate a Trifunctional T cell-antigen coupler (Tri-TAC). In some instances, the TAC draws the CD3 molecule and the TCR into regions of lipid rafts and brings Lck into the proximity of the TCR, similar to natural MHC binding.

Cancers that may be treated include any form of neoplastic disease. Examples of cancers that may be treated include, but are not limited to breast cancer, lung cancer and leukemia, for example mixed lineage leukemia (MLL), chronic lymphocytic leukemia (CLL) or acute lymphoblastic leukemia (ALL). Other cancers include carcinomas, blastomas, melanomas, sarcomas, hematological cancers, lymphoid malignancies, benign and malignant tumors, and malignancies. The cancer can comprise non-solid tumors or solid tumors. Cancers that may be treated include tumors that are not vascularized, or not yet substantially vascularized, as well as vascularized tumors. In some instances, the cancer is a solid cancer or comprises a solid tumor. In some instances, the cancer is a liquid cancer or comprises a liquid tumor. In some instances, the cancer is a lung cancer, a breast cancer, a colon cancer, multiple myeloma, glioblastoma, gastric cancer, ovarian cancer, stomach cancer, colorectal cancer, urothelial cancer, endometrial cancer, or a melanoma. In some instances, the cancer is a lung cancer. In some instances, the cancer is a breast cancer. In some instances, the cancer is a colon cancer. In some instances, the cancer is multiple myeloma. In some instances, the cancer is a glioblastoma. In some instances, the cancer is a gastric cancer. In some instances, the cancer is an ovarian cancer. In some instances, the cancer is a stomach cancer. In some instances, the cancer is a colorectal cancer. In some instances, the cancer is urothelial cancer. In some instances, the cancer is an endometrial cancer. In some instances, the cancer is a melanoma.

Disclosed herein, in some embodiments, are method of treating a cancer expressing a HER-2 antigen in an individual in need thereof, comprising administering to the individual an engineered T cell comprising a nucleic acid sequence encoding an anti-HER-2 Trifunctional T cell-antigen coupler (anti-HER-2 Tri-TAC) comprising: (a) a first polynucleotide sequence encoding a ligand that selectively binds the HER-2 antigen; (b) a second polynucleotide sequence encoding a murine UCHT1 (muUCHT1) ligand with a Y182T mutation comprising an amino acid sequence having at least 70% sequence identity with SEQ ID NO: 26 that binds a protein associated with a T cell receptor (TCR) complex; and (c) a third polynucleotide sequence encoding a TCR signaling domain polypeptide. In some instances, the ligand specifically binds the HER-2 antigen. In some instances, the second polynucleotide sequence encoding a muUCHT1 ligand with a Y182T mutation comprises an amino acid sequence having at least 75% sequence identity with SEQ ID NO: 26. In some instances, the second polynucleotide sequence encoding a muUCHT1 ligand with a Y182T mutation comprises an amino acid sequence having at least 80% sequence identity with SEQ ID NO: 26. In some instances, the second polynucleotide sequence encoding a muUCHT1 ligand with a Y182T mutation comprises an amino acid sequence having at least 85% sequence identity with SEQ ID NO: 26. In some instances, the second polynucleotide sequence encoding a muUCHT1 ligand with a Y182T mutation comprises an amino acid sequence having at least 90% sequence identity with SEQ ID NO: 26. In some instances, the second polynucleotide sequence encoding a muUCHT1 ligand with a Y182T mutation comprises an amino acid sequence having at least 95% sequence identity with SEQ ID NO: 26. In some instances, the second polynucleotide sequence encoding a muUCHT1 ligand with a Y182T mutation comprises an amino acid sequence of SEQ ID NO: 26. In some instances, the percent sequence identity of the second polypeptide sequence encoding a muUCHT1 ligand with a Y182T mutation with SEQ ID NO: 26 refers to amino acids other than the Y182T mutation.

Also disclosed herein, in some embodiments, are method of treating a cancer expressing a HER-2 antigen in an individual in need thereof, comprising administering to the individual an engineered T cell comprising a nucleic acid sequence encoding an anti-HER-2 T cell-antigen coupler (anti-HER-2 Tri-TAC) comprising: (a) a first polynucleotide sequence encoding a ligand that selectively binds the HER-2 antigen; (b) a second polynucleotide sequence encoding a humanized UCHT1 (huUCHT1) ligand comprising an amino acid sequence having at least 70% sequence identity with SEQ ID NO: 29 that binds a protein associated with a T cell receptor (TCR) complex; and (c) a third polynucleotide sequence encoding a TCR signaling domain polypeptide. In some instances, the ligand specifically binds the HER-2 antigen. In some instances, the second polynucleotide sequence encoding a huUCHT1 ligand comprises an amino acid sequence having at least 75% sequence identity with SEQ ID NO: 29. In some instances, the second polynucleotide sequence encoding a huUCHT1 ligand comprises an amino acid sequence having at least 80% sequence identity with SEQ ID NO: 29. In some instances, the second polynucleotide sequence encoding a huUCHT1 ligand comprises an amino acid sequence having at least 85% sequence identity with SEQ ID NO: 29. In some instances, the second polynucleotide sequence encoding a huUCHT1 ligand comprises an amino acid sequence having at least 90% sequence identity with SEQ ID NO: 29. In some instances, the second polynucleotide sequence encoding a huUCHT1 ligand comprises an amino acid sequence having at least 95% sequence identity with SEQ ID NO: 29. In some instances, the second polynucleotide sequence encoding a huUCHT1 ligand comprises an amino acid sequence of SEQ ID NO: 29.

Further disclosed herein, in some embodiments, are method of treating a cancer expressing a HER-2 antigen in an individual in need thereof, comprising administering to the individual an engineered T cell comprising a nucleic acid sequence encoding an anti-HER-2 T cell-antigen coupler (anti-HER-2 Tri-TAC) comprising: (a) a first polynucleotide sequence encoding a ligand that selectively binds the HER-2 antigen; (b) a second polynucleotide sequence encoding a humanized UCHT1 (huUCHT1) ligand with a Y177T mutation comprising an amino acid sequence having at least 70% sequence identity with SEQ ID NO: 28 that binds a protein associated with a T cell receptor (TCR) complex; and (c) a third polynucleotide sequence encoding a TCR signaling domain polypeptide. In some instances, the ligand specifically binds the HER-2 antigen. In some instances, the second polynucleotide sequence encoding a huUCHT1 ligand with a Y177T mutation comprises an amino acid sequence having at least 75% sequence identity with SEQ ID NO: 28. In some instances, the second polynucleotide sequence encoding a huUCHT1 ligand with a Y177T mutation comprises an amino acid sequence having at least 80% sequence identity with SEQ ID NO: 28. In some instances, the second polynucleotide sequence encoding a huUCHT1 ligand with a Y177T mutation comprises an amino acid sequence having at least 85% sequence identity with SEQ ID NO: 28. In some instances, the second polynucleotide sequence encoding a huUCHT1 ligand with a Y177T mutation comprises an amino acid sequence having at least 90% sequence identity with SEQ ID NO: 28. In some instances, the second polynucleotide sequence encoding a huUCHT1 ligand with a Y177T mutation comprises an amino acid sequence having at least 95% sequence identity with SEQ ID NO: 28. In some instances, the second polynucleotide sequence encoding a huUCHT1 ligand with a Y177T mutation comprises an amino acid sequence of SEQ ID NO: 28. In some instances, the percent sequence identity of the second polypeptide sequence encoding a huUCHT1 ligand with a Y177T mutation with SEQ ID NO: 28 refers to amino acids other than the Y177T mutation.

In some embodiments, the ligand that selectively binds a target antigen (or a target-specific ligand) directs the Tri-functional T cell-antigen coupler (Tri-TAC) to a target cell. In some instances, the target-specific ligand is referred to as an antigen binding domain. In some instances, a target-specific ligand refers to any substance that binds, directly or indirectly, to a target cell. In some embodiments, the target specific ligand binds to an antigen (protein produced by a cell that can elicit an immune response) on the target cell. In some instances, the target-specific ligands include, but are not limited to, antibodies and fragments thereof, for example single chain antibodies such as single-chain antibodies (scFvs), single domain antibodies, peptides, peptidomimetics, proteins, glycoproteins, or proteoglycans that bind to the target cell and/or antigen. In some instances, the target-specific ligands include, but are not limited to, designed ankyrin repeat proteins (DARPins), lectins, knottins, centryrins, anticalins, or naturally occurring ligands for the tumor antigen, such as growth factors, enzyme substrates, receptors or binding proteins. In some instances, target specific ligands include non-protein compounds that bind to target cells and/or antigens, including but not limited to carbohydrates, lipids, nucleic acids, or small molecules. In some instances, a target-specific ligand is a designed ankyrin repeat (DARPin) targeted to a specific cell and/or antigen. In some instances, the target-specific ligand is a DARPin that selectively binds a HER-2 (erbB-2) antigen. In some instances, the target-specific ligand is a DARPin that specifically binds a HER-2 (erbB-2) antigen. In some instances, the DARPin targeted to HER-2 (erb-2) comprises SEQ ID NO: 7 and SEQ ID NO: 8.

In some instances, a target cell is a cell associated with a disease state, including, but not limited to cancer. In some embodiments, a target cell is a tumor cell. In some instances, a target-specific ligand can bind to a tumor antigen or tumor associated antigen on a tumor cell. In some instances, the target antigen is a tumor antigen. In some instances, the tumor antigen when proteinaceous is a sequence of 8 or more amino acids up to the full protein. In some instances, the tumor antigen is any number of amino acids in between 8 and the full length protein which comprises at least one antigenic fragment of the full length protein that is represented in a MHC complex. Examples of tumor antigens include, but are not limited to, HER-2 (erbB-2), B-cell maturation antigen (BCMA), alphafetoprotein (AFP), carcinoembryonic antigen (CEA), CA-125, MUC-1, epithelial tumor antigen (ETA), tyrosinase, melanoma-associated antigen (MAGE), prostate-specific antigen (PSA), glioma-associated antigen, (3-human chorionic gonadotropin, thyroglobulin, RAGE-1, MN-CA IX, human telomerase reverse transcriptase, RU1, RU2 (AS), intestinal carboxyl esterase, mut hsp70-2, M-CSF, prostase, PAP, NY-ESO-1, LAGE-1a, p53, prostein, PSMA, survivin and telomerase, prostate-carcinoma tumor antigen-1 (PCTA-1), ELF2M, neutrophil elastase, CD22, insulin growth factor (IGF)-I, IGF-II, IGF-I receptor and mesothelin. In some instances, the tumor antigen is a HER-2 antigen. In some instances, the HER-2 specific ligand comprises an antigen binding domain of an antibody selected from Trastuzumab, Pertuzumab, Lapatinib, Neratinib, Ado-trastuzmab Emtansine, Gancotamab, Margetuximab, Timigutuzumab, and Ertumaxomab.

In some embodiments, the Tri-TAC recruits the T-Cell Receptor (TCR) in combination with co-receptor stimulation. In some instances, the TAC comprises a ligand that binds a protein associated with the TCR complex. In some instances, the ligand that binds a protein associated with a TCR complex comprises a substance that binds, directly or indirectly, to a protein of the TCR. Proteins associated with the TCR include, but are not limited to, the TCR alpha (α) chain, TCR beta (β) chain, TCR gamma (γ) chain, TCR delta (δ) chain, CD3γ chain, CD3δ chain and CD3ε chains. In some embodiments, a ligand that binds a protein associated with the TCR complex is an antibody to the TCR alpha (α) chain, TCR beta (β) chain, TCR gamma (γ) chain, TCR delta (δ) chain, CD3γ chain, CD3δ chain and/or CD3ε chain. In some instances, the protein associated with a TCR complex is CD3. In some instances, the protein associated with a TCR complex is CD3ε. In some embodiments, the ligand is an antibody or a fragment thereof that binds CD3. Examples of CD3 antibodies, include, but are not limited to, for muromonab, otelixizumab, teplizumab and visilizumab. In some embodiments, the antibody that binds CD3 is a single chain antibody, for example a single-chain antibody (scFv). In some instances, the ligand that binds to a CD3 is UCHT1. In some instances, the UCHT1 ligand binds CD3ε. In some instances, the UCHT1 ligand is a murine ligand. In some instances, the murine UCHT1 ligand comprises SEQ ID NOs: 13 and 14. In some instances, the murine UCHT1 ligand binds CD3ε. In some instances, the murine UCHT1 ligand with a Y182T mutation binds CD3ε. In some instances, the humanized UCHT1 ligand binds CD3ε. In some instances, the humanized UCHT1 ligand with a Y177T mutation binds CD3ε.

In some embodiments, the TCR signaling domain polypeptide comprises a transmembrane domain. In some embodiments, the TCR signaling domain polypeptide comprises a cytoplasmic domain. In some embodiments, the TCR signaling domain polypeptide comprises a transmembrane domain and a cytosolic domain. In some instances, the TCR signaling domain polypeptide comprises a transmembrane domain and/or a cytosolic domain of a TCR co-receptor. In some instances, the TCR co-receptor is CD4. In some instances, the TCR signaling domain polypeptide comprises the transmembrane and cytoplasmic domains of the CD4 co-receptor comprising SEQ ID NO: 17 and 18. In some instances, the TCR co-receptor is CD8. In some instances, the TCR co-receptor is CD8α. In some instances, the TCR co-receptor is CD5. In some instances, the TCR co-receptor is CD9. In some instances, the TCR co-receptor is CD5. In some instances, the TCR co-receptor is CD22. In some instances, the TCR signaling domain polypeptide comprises a transmembrane domain and/or a cytosolic domain of a TCR co-stimulator. In some instances, the TCR co-stimulator is ICOS. In some instances, the TCR co-stimulator is CD27. In some instances, the TCR co-stimulator is CD28. In some instances, the TCR co-stimulator is 4-1BB (CD137). In some instances, the TCR co-stimulator is OX40 (CD134). In some instances, the TCR co-stimulator is CD30. In some instances, the TCR co-stimulator is CD40. In some instances, the TCR co-stimulator is lymphocyte fiction-associated antigen 1 (LFA-1). In some instances, the TCR co-stimulator is CD2. In some instances, the TCR co-stimulator is CD7. In some instances, the TCR co-stimulator is LIGHT. In some instances, the TCR co-stimulator is NKG2C. In some instances, the TCR co-stimulator is B7-H3. In some instances, the TCR co-stimulator is a ligand that specifically binds CD83. In some instances, the TCR signaling domain polypeptide comprises a transmembrane domain and/or cytosolic domain of a TCR co-inhibitor. In some instances, the TCR co-inhibitor is PD-1.

In some instances, the TCR co-inhibitor is TIM3. In some instances, the TCR co-inhibitor is LAG-3. In some instances, the TCR co-inhibitor is TIGIT. In some instances, the TCR co-inhibitor is BTLA. In some instances, the TCR co-inhibitor is CD160. In some instances, the TCR co-inhibitor is CD37. In some embodiments, the TCR signaling domain polypeptide includes both a cytoplasmic domain and a transmembrane domain of a TCR co-receptor or co-stimulator protein. In some instances, the cytoplasmic domain and transmembrane domain are from the same co-receptor or co-stimulator or from different co-receptors or co-stimulators. In some instances, the cytoplasmic domain and transmembrane domains are optionally joined by a linker. In some embodiments, the TAC further comprises other polypeptides that directly or indirectly act to target or activate the T cell.

In some embodiments, the first polypeptide, the second polypeptide, and the third polypeptide are directly fused. In some embodiments, the first polypeptide, the second polypeptide, and the third polypeptide are joined by at least one linker. In some embodiments, the first polypeptide and the second polypeptide are directly fused, and joined to the third polypeptide by a linker. In some embodiments, the second polypeptide and the third polypeptide are directly fused, and joined to the first polypeptide by a linker. In some embodiments, the linker is a peptide linker. In some embodiments, the peptide linker comprises 1 to 40 amino acids. In some embodiments, the peptide linker comprises 1 to 30 amino acids. In some embodiments, the peptide linker comprises 1 to 15 amino acids. In some embodiments, the peptide linker comprises 1 to 10 amino acids. In some embodiments, the peptide linker comprises 1 to 6 amino acids. In some embodiments, the peptide linker comprises 30 to 40 amino acids. In some embodiments, the peptide linker comprises 32 to 36 amino acids. In some embodiments, the peptide linker comprises 5 to 30 amino acids. In some embodiments, the peptide linker comprises 5 amino acids. In some embodiments, the peptide linker comprises 10 amino acids. In some embodiments, the peptide linker comprises 15 amino acids. In some embodiments, the peptide linker comprises 20 amino acids. In some embodiments, the peptide linker comprises 25 amino acids. In some embodiments, the peptide linker comprises 30 amino acids. In some embodiments, the peptide linker comprises a G4S3 linker. Other examples of linkers that, in some instances, are used in the TAC, are peptides corresponding to SEQ ID NOs: 11, 12, 15, 16, 19 and 20 and variants and fragments thereof.

In some embodiments, the transmembrane and cytoplasmic domains of the CD4 co-receptor are fused to single-chain antibody that binds CD3. In some instances, the TAC draws the CD3 molecule and the TCR into regions of lipid rafts and brings Lck into the proximity of the TCR, similar to natural MHC binding. In some instances, a designed ankyrin repeat (DARPin) is linked to the CD4-UCHT1 chimera to generate a Trifunctional T cell-antigen coupler (Tri-TAC).

Cancers that may be treated include any form of neoplastic disease. Examples of cancers that may be treated include, but are not limited to breast cancer, lung cancer and leukemia, for example mixed lineage leukemia (MLL), chronic lymphocytic leukemia (CLL) or acute lymphoblastic leukemia (ALL). Other cancers include carcinomas, blastomas, melanomas, sarcomas, hematological cancers, lymphoid malignancies, benign and malignant tumors, and malignancies. The cancer can comprise non-solid tumors or solid tumors. Cancers that may be treated include tumors that are not vascularized, or not yet substantially vascularized, as well as vascularized tumors. In some instances, the cancer is a solid cancer or comprises a solid tumor. In some instances, the cancer is a liquid cancer or comprises a liquid tumor. In some instances, the cancer is a lung cancer, a breast cancer, a colon cancer, multiple myeloma, glioblastoma, gastric cancer, ovarian cancer, stomach cancer, colorectal cancer, urothelial cancer, or endometrial cancer. In some instances, the cancer is a lung cancer. In some instances, the cancer is a breast cancer. In some instances, the cancer is a colon cancer. In some instances, the cancer is multiple myeloma. In some instances, the cancer is a glioblastoma. In some instances, the cancer is a gastric cancer. In some instances, the cancer is an ovarian cancer. In some instances, the cancer is a stomach cancer. In some instances, the cancer is a colorectal cancer. In some instances, the cancer is urothelial cancer. In some instances, the cancer is an endometrial cancer.

Disclosed herein, in some embodiments, are method of treating a cancer expressing a BCMA antigen in an individual in need thereof, comprising administering to the individual an engineered T cell comprising a nucleic acid sequence encoding an anti-BCMA T cell-antigen coupler (anti-BCMA Tri-TAC) comprising: (a) a first polynucleotide sequence encoding a ligand that selectively binds the BCMA antigen; (b) a second polynucleotide sequence encoding a murine UCHT1 (muUCHT1) ligand with a Y182T mutation comprising an amino acid sequence having at least 70% sequence identity with SEQ ID NO: 26 that binds a protein associated with a T cell receptor (TCR) complex; and (c) a third polynucleotide sequence encoding a TCR signaling domain polypeptide. In some instances, the ligand specifically binds the BCMA antigen. In some instances, the second polynucleotide sequence encoding a muUCHT1 ligand with a Y182T mutation comprises an amino acid sequence having at least 75% sequence identity with SEQ ID NO: 26. In some instances, the second polynucleotide sequence encoding a muUCHT1 ligand with a Y182T mutation comprises an amino acid sequence having at least 80% sequence identity with SEQ ID NO: 26. In some instances, the second polynucleotide sequence encoding a muUCHT1 ligand with a Y182T mutation comprises an amino acid sequence having at least 85% sequence identity with SEQ ID NO: 26. In some instances, the second polynucleotide sequence encoding a muUCHT1 ligand with a Y182T mutation comprises an amino acid sequence having at least 90% sequence identity with SEQ ID NO: 26. In some instances, the second polynucleotide sequence encoding a muUCHT1 ligand with a Y182T mutation comprises an amino acid sequence having at least 95% sequence identity with SEQ ID NO: 26. In some instances, the second polynucleotide sequence encoding a muUCHT1 ligand with a Y182T mutation comprises an amino acid sequence of SEQ ID NO: 26. In some instances, the percent sequence identity of the second polypeptide sequence encoding a muUCHT1 ligand with a Y182T mutation with SEQ ID NO: 26 refers to amino acids other than the Y182T mutation.

Also disclosed herein, in some embodiments, are method of treating a cancer expressing a BCMA antigen in an individual in need thereof, comprising administering to the individual an engineered T cell comprising a nucleic acid sequence encoding an anti-BCMA T cell-antigen coupler (anti-BCMA Tri-TAC) comprising: (a) a first polynucleotide sequence encoding a ligand that selectively binds the BCMA antigen; (b) a second polynucleotide sequence encoding a humanized UCHT1 (huUCHT1) ligand comprising an amino acid sequence having at least 70% sequence identity with SEQ ID NO: 29 that binds a protein associated with a T cell receptor (TCR) complex; and (c) a third polynucleotide sequence encoding a TCR signaling domain polypeptide. In some instances, the ligand specifically binds the BCMA antigen. In some instances, the second polynucleotide sequence encoding a huUCHT1 ligand comprises an amino acid sequence having at least 75% sequence identity with SEQ ID NO: 29. In some instances, the second polynucleotide sequence encoding a huUCHT1 ligand comprises an amino acid sequence having at least 80% sequence identity with SEQ ID NO: 29. In some instances, the second polynucleotide sequence encoding a huUCHT1 ligand comprises an amino acid sequence having at least 85% sequence identity with SEQ ID NO: 29. In some instances, the second polynucleotide sequence encoding a huUCHT1 ligand comprises an amino acid sequence having at least 90% sequence identity with SEQ ID NO: 29. In some instances, the second polynucleotide sequence encoding a huUCHT1 ligand comprises an amino acid sequence having at least 95% sequence identity with SEQ ID NO: 29. In some instances, the second polynucleotide sequence encoding a huUCHT1 ligand comprises an amino acid sequence of SEQ ID NO: 29.

Further disclosed herein, in some embodiments, are method of treating a cancer expressing a BCMA antigen in an individual in need thereof, comprising administering to the individual an engineered T cell comprising a nucleic acid sequence encoding an anti-BCMA T cell-antigen coupler (anti-BCMA Tri-TAC) comprising: (a) a first polynucleotide sequence encoding a ligand that selectively binds the BCMA antigen; (b) a second polynucleotide sequence encoding a humanized UCHT1 (huUCHT1) ligand with a Y177T mutation comprising an amino acid sequence having at least 70% sequence identity with SEQ ID NO: 28 that binds a protein associated with a T cell receptor (TCR) complex; and (c) a third polynucleotide sequence encoding a TCR signaling domain polypeptide. In some instances, the ligand specifically binds the BCMA antigen. In some instances, the second polynucleotide sequence encoding a huUCHT1 ligand with a Y177T mutation comprises an amino acid sequence having at least 75% sequence identity with SEQ ID NO: 28. In some instances, the second polynucleotide sequence encoding a huUCHT1 ligand with a Y177T mutation comprises an amino acid sequence having at least 80% sequence identity with SEQ ID NO: 28. In some instances, the second polynucleotide sequence encoding a huUCHT1 ligand with a Y177T mutation comprises an amino acid sequence having at least 85% sequence identity with SEQ ID NO: 28. In some instances, the second polynucleotide sequence encoding a huUCHT1 ligand with a Y177T mutation comprises an amino acid sequence having at least 90% sequence identity with SEQ ID NO: 28. In some instances, the second polynucleotide sequence encoding a huUCHT1 ligand with a Y177T mutation comprises an amino acid sequence having at least 95% sequence identity with SEQ ID NO: 28. In some instances, the second polynucleotide sequence encoding a huUCHT1 ligand with a Y177T mutation comprises an amino acid sequence of SEQ ID NO: 28. In some instances, the percent sequence identity of the second polypeptide sequence encoding a huUCHT1 ligand with a Y177T mutation with SEQ ID NO: 28 refers to amino acids other than the Y177T mutation.

In some embodiments, the ligand that selectively binds a target antigen (or a target-specific ligand) directs the T cell-antigen coupler (TAC) to a target cell. In some instances, the target-specific ligand is referred to as an antigen binding domain. In some instances, a target-specific ligand refers to any substance that binds, directly or indirectly, to a target cell. In some embodiments, the target specific ligand binds to an antigen (protein produced by a cell that can elicit an immune response) on the target cell. In some instances, the target-specific ligands include, but are not limited to, antibodies and fragments thereof, for example single chain antibodies such as single-chain antibodies (scFvs), single domain antibodies, peptides, peptidomimetics, proteins, glycoproteins, or proteoglycans that bind to the target cell and/or antigen. In some instances, the target-specific ligands include, but are not limited to, designed ankyrin repeat proteins (DARPins), lectins, knottins, centryrins, anticalins, or naturally occurring ligands for the tumor antigen, such as growth factors, enzyme substrates, receptors or binding proteins. In some instances, target specific ligands include non-protein compounds that bind to target cells and/or antigens, including but not limited to carbohydrates, lipids, nucleic acids, or small molecules. In some instances, a target-specific ligand is a designed ankyrin repeat (DARPin) targeted to a specific cell and/or antigen. In some instances, the target-specific ligand is a single-chain antibody (scFv) targeted to a specific cell and/or antigen. In some instances, the target-specific ligand is a scFv that selectively binds BCMA. In some instances, the target-specific ligand is a scFv that specifically binds BCMA. In some instances, the scFv that binds BCMA comprises SEQ ID NO: 21 and SEQ ID NO: 22.

In some instances, a target cell is a cell associated with a disease state, including, but not limited to cancer. In some embodiments, a target cell is a tumor cell. In some instances, a target-specific ligand can bind to a tumor antigen or tumor associated antigen on a tumor cell. In some instances, the target antigen is a tumor antigen. In some instances, the tumor antigen when proteinaceous is a sequence of 8 or more amino acids up to the full protein. In some instances, the tumor antigen is any number of amino acids in between 8 and the full length protein which comprises at least one antigenic fragment of the full length protein that is represented in a MHC complex. Examples of tumor antigens include, but are not limited to, HER-2 (erbB-2), B-cell maturation antigen (BCMA), alphafetoprotein (AFP), carcinoembryonic antigen (CEA), CA-125, MUC-1, epithelial tumor antigen (ETA), tyrosinase, melanoma-associated antigen (MAGE), prostate-specific antigen (PSA), glioma-associated antigen, (3-human chorionic gonadotropin, thyroglobulin, RAGE-1, MN-CA IX, human telomerase reverse transcriptase, RU1, RU2 (AS), intestinal carboxyl esterase, mut hsp70-2, M-CSF, prostase, PAP, NY-ESO-1, LAGE-1a, p53, prostein, PSMA, survivin and telomerase, prostate-carcinoma tumor antigen-1 (PCTA-1), ELF2M, neutrophil elastase, CD22, insulin growth factor (IGF)-I, IGF-II, IGF-I receptor and mesothelin. In some instances, the tumor antigen is a BCMA antigen. In some instances, the BCMA specific ligand comprises an antigen binding domain of an antibody selected from Belantamab mafodotin, and GSK2857916.

In some embodiments, the TAC recruits the T-Cell Receptor (TCR) in combination with co-receptor stimulation. In some instances, the TAC comprises a ligand that binds a protein associated with the TCR complex. In some instances, the ligand that binds a protein associated with a TCR complex comprises a substance that binds, directly or indirectly, to a protein of the TCR. Proteins associated with the TCR include, but are not limited to, the TCR alpha (α) chain, TCR beta (β) chain, TCR gamma (γ) chain, TCR delta (δ) chain, CD3γ chain, CD3δ chain and CD3ε chains. In some embodiments, a ligand that binds a protein associated with the TCR complex is an antibody to the TCR alpha (α) chain, TCR beta (β) chain, TCR gamma (γ) chain, TCR delta (δ) chain, CD3γ chain, CD3δ chain and/or CD3ε chain. In some instances, the protein associated with a TCR complex is CD3. In some instances, the protein associated with a TCR complex is CD3ε. In some embodiments, the ligand is an antibody or a fragment thereof that binds CD3. Examples of CD3 antibodies, include, but are not limited to, for muromonab, otelixizumab, teplizumab and visilizumab. In some embodiments, the antibody that binds CD3 is a single chain antibody, for example a single-chain antibody (scFv). In some instances, the ligand that binds to a CD3 is UCHT1. In some instances, the UCHT1 ligand binds CD3ε. In some instances, the UCHT1 ligand is a murine ligand. In some instances, the murine UCHT1 ligand comprises SEQ ID NOs: 13 and 14. In some instances, the murine UCHT1 ligand binds CD3ε. In some instances, the murine UCHT1 ligand with a Y182T mutation binds CD3ε. In some instances, the humanized UCHT1 ligand binds CD3ε. In some instances, the humanized UCHT1 ligand with a Y177T mutation binds CD3ε.

In some embodiments, the TCR signaling domain polypeptide comprises a transmembrane domain. In some embodiments, the TCR signaling domain polypeptide comprises a cytoplasmic domain. In some embodiments, the TCR signaling domain polypeptide comprises a transmembrane domain and a cytosolic domain. In some instances, the TCR signaling domain polypeptide comprises a transmembrane domain and/or a cytosolic domain of a TCR co-receptor. In some instances, the TCR co-receptor is CD4. In some instances, the TCR signaling domain polypeptide comprises the transmembrane and cytoplasmic domains of the CD4 co-receptor comprising SEQ ID NO: 17 and 18. In some instances, the TCR co-receptor is CD8. In some instances, the TCR co-receptor is CD8α. In some instances, the TCR co-receptor is CD5. In some instances, the TCR co-receptor is CD9. In some instances, the TCR co-receptor is CD5. In some instances, the TCR co-receptor is CD22. In some instances, the TCR signaling domain polypeptide comprises a transmembrane domain and/or a cytosolic domain of a TCR co-stimulator. In some instances, the TCR co-stimulator is ICOS. In some instances, the TCR co-stimulator is CD27. In some instances, the TCR co-stimulator is CD28. In some instances, the TCR co-stimulator is 4-1BB (CD137). In some instances, the TCR co-stimulator is OX40 (CD134). In some instances, the TCR co-stimulator is CD30. In some instances, the TCR co-stimulator is CD40. In some instances, the TCR co-stimulator is lymphocyte fiction-associated antigen 1 (LFA-1). In some instances, the TCR co-stimulator is CD2. In some instances, the TCR co-stimulator is CD7. In some instances, the TCR co-stimulator is LIGHT. In some instances, the TCR co-stimulator is NKG2C. In some instances, the TCR co-stimulator is B7-H3. In some instances, the TCR co-stimulator is a ligand that specifically binds CD83. In some instances, the TCR signaling domain polypeptide comprises a transmembrane domain and/or a cytosolic domain of a TCR co-inhibitor. In some instances, the TCR co-inhibitor is PD-1. In some instances, the TCR co-inhibitor is TIM3. In some instances, the TCR co-inhibitor is LAG-3. In some instances, the TCR co-inhibitor is TIGIT. In some instances, the TCR co-inhibitor is BTLA. In some instances, the TCR co-inhibitor is CD160. In some instances, the TCR co-inhibitor is CD37. In some embodiments, the TCR signaling domain polypeptide includes both a cytoplasmic domain and a transmembrane domain of a TCR co-receptor or co-stimulator protein. In some instances, the cytoplasmic domain and transmembrane domain are from the same co-receptor or co-stimulator or from different co-receptors or co-stimulators. In some instances, the cytoplasmic domain and transmembrane domains are optionally joined by a linker. In some embodiments, the TAC further comprises other polypeptides that directly or indirectly act to target or activate the T cell.

In some embodiments, the first polypeptide, the second polypeptide, and the third polypeptide are directly fused. In some embodiments, the first polypeptide, the second polypeptide, and the third polypeptide are joined by at least one linker. In some embodiments, the first polypeptide and the second polypeptide are directly fused, and joined to the third polypeptide by a linker. In some embodiments, the second polypeptide and the third polypeptide are directly fused, and joined to the first polypeptide by a linker. In some embodiments, the linker is a peptide linker. In some embodiments, the peptide linker comprises 1 to 40 amino acids. In some embodiments, the peptide linker comprises 1 to 30 amino acids. In some embodiments, the peptide linker comprises 1 to 15 amino acids. In some embodiments, the peptide linker comprises 1 to 10 amino acids. In some embodiments, the peptide linker comprises 1 to 6 amino acids. In some embodiments, the peptide linker comprises 30 to 40 amino acids. In some embodiments, the peptide linker comprises 32 to 36 amino acids. In some embodiments, the peptide linker comprises 5 to 30 amino acids. In some embodiments, the peptide linker comprises 5 amino acids. In some embodiments, the peptide linker comprises 10 amino acids. In some embodiments, the peptide linker comprises 15 amino acids. In some embodiments, the peptide linker comprises 20 amino acids. In some embodiments, the peptide linker comprises 25 amino acids. In some embodiments, the peptide linker comprises 30 amino acids. In some embodiments, the peptide linker comprises a G4S3 linker. Other examples of linkers that, in some instances, are used in the TAC, are peptides corresponding to SEQ ID NOs: 11, 12, 15, 16, 19 and 20 and variants and fragments thereof.

In some embodiments, the transmembrane and cytoplasmic domains of the CD4 co-receptor are fused to single-chain antibody that binds CD3. In some instances, a designed ankyrin repeat (DARPin) is linked to the CD4-UCHT1 chimera to generate a Trifunctional T cell-antigen coupler (Tri-TAC). In some instances, the Tri-TAC draws the CD3 molecule and the TCR into regions of lipid rafts and brings Lck into the proximity of the TCR, similar to natural MHC binding.

Cancers that may be treated include any form of neoplastic disease. Examples of cancers that may be treated include, but are not limited to breast cancer, lung cancer and leukemia, for example mixed lineage leukemia (MLL), chronic lymphocytic leukemia (CLL) or acute lymphoblastic leukemia (ALL). Other cancers include carcinomas, blastomas, melanomas, sarcomas, hematological cancers, lymphoid malignancies, benign and malignant tumors, and malignancies. The cancer can comprise non-solid tumors or solid tumors. Cancers that may be treated include tumors that are not vascularized, or not yet substantially vascularized, as well as vascularized tumors. In some instances, the cancer is a solid cancer or comprises a solid tumor. In some instances, the cancer is a liquid cancer or comprises a liquid tumor. In some instances, the cancer is a melanoma.

TABLE 1

Table of Sequences

| SEQ ID NO | Description | Nucleotide/ Amino Acid |
|---|---|---|
| SEQ ID NO: 1 | N-Darpin Tri TAC | Nucleotide |
| SEQ ID NO: 2 | N-Darpin Tri TAC | Amino Acid |
| SEQ ID NO: 3 | C-Darpin Tri TAC | Nucleotide |
| SEQ ID NO: 4 | C-Darpin Tri TAC | Amino Acid |
| SEQ ID NO: 5 | N-Darpin Tri TAC leader sequence (secretion signal) | Nucleotide |
| SEQ ID NO: 6 | N-Darpin Tri TAC leader sequence (secretion signal) | Amino Acid |
| SEQ ID NO: 7 | DARPin specific for HER-2 antigen | Nucleotide |
| SEQ ID NO: 8 | DARPin specific for HER-2 antigen | Amino Acid |
| SEQ ID NO: 9 | Myc Tag | Nucleotide |
| SEQ ID NO: 10 | Myc Tag | Amino Acid |
| SEQ ID NO: 11 | Linker 1 | Nucleotide |
| SEQ ID NO: 12 | Linker 1 | Amino Acid |
| SEQ ID NO: 13 | UCHT1[1] | Nucleotide |
| SEQ ID NO: 14 | UCHT1[2] | Amino Acid |
| SEQ ID NO: 15 | Linker 2 | Nucleotide |
| SEQ ID NO: 16 | Linker 2 | Amino Acid |
| SEQ ID NO: 17 | CD4 Domain[3] | Nucleotide |
| SEQ ID NO: 18 | CD4 Domain[4] | Amino Acid |
| SEQ ID NO: 19 | CD4 based linker | Nucleotide |
| SEQ ID NO: 20 | CD4 based linker | Amino Acid |
| SEQ ID NO: 21 | ScFv specific for BCMA antigen | Nucleotide |
| SEQ ID NO: 22 | ScFv specific for BCMA antigen | Amino Acid |
| SEQ ID NO: 23 | UCHT1 (A85V, T161P) | Nucleotide |
| SEQ ID NO: 24 | UCHT1 (A85V, T161P) | Amino Acid |
| SEQ ID NO: 25 | muUCHT1 (Y182T) | Nucleotide |
| SEQ ID NO: 26 | muUCHT1 (Y182T) | Amino Acid |
| SEQ ID NO: 27 | huUCHT1 (Y177T) | Nucleotide |
| SEQ ID NO: 28 | huUCHT1 (Y177T) | Amino Acid |
| SEQ ID NO: 29 | huUCHT1 (Y177T) | Amino Acid |
| SEQ ID NO: 30 | (G$_4$S)$_3$ linker | Amino Acid |
| SEQ ID NO: 31 | huUCHT1 (Y177T) | Nucleotide |

[1]Light chain, nucleotides 1-324; Linker, nucleotides 325-387; Heavy chain, nucleotides 388-750
[2]Light chain, amino acids 1-108; Linker, amino acids 109-128; Heavy chain, amino acids 129-250
[3]Extracellular linker, nucleotides 1-66; Transmembrane domain, nucleotides 67-132; Cytosolic domain, nucleotides 133-254
[4]Extracellular linker, amino acids 1-22; Transmembrane domain, amino acids 23-44; Cytosolic domain, amino acids 45-84

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1. Characterization of the Tri-TAC Technology

Figure 1B:
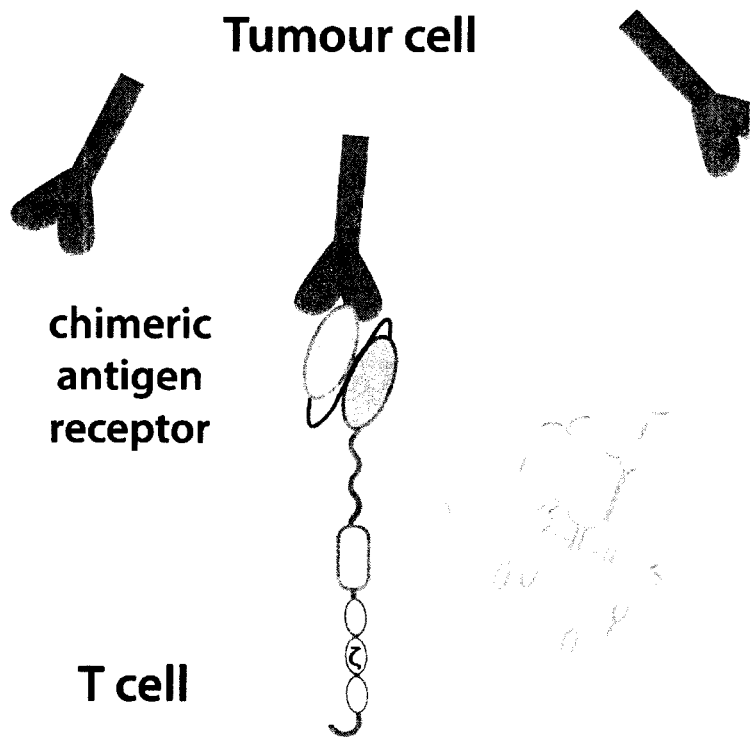
FIG. 1B is a schematic of CAR based T-cell activation.
Figure 1C:
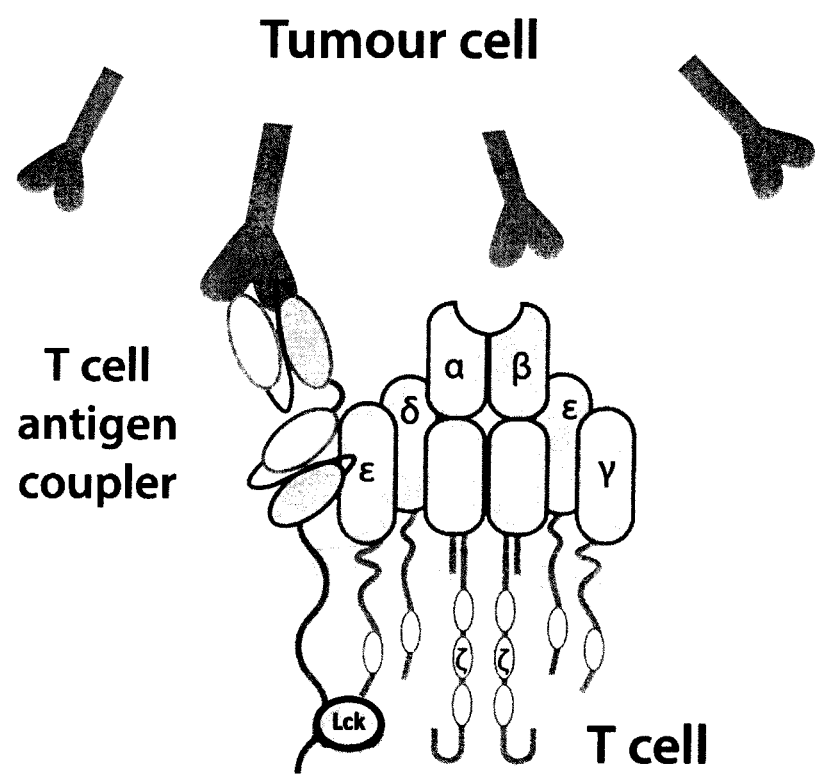
FIG. 1C is a schematic of a trifunctional-T cell-antigen coupler (Tri-TAC) based T cell activation.

An overview of the Tri-TAC technology is provided in FIG. 1A-FIG. 1C.

FIG. 1A shows an example of CD8 T-cell activation based on the co-assembly of different receptors and their associated protein partners. Initially, the major histocompatibility complex I is presenting an antigen (helix). This is recognized by a T cell receptor (TCR) complex capable of binding the antigen. The TCR complex contains several individual subunits. The α/β domains are able to interact directly with the antigen presented on MHC-I. The α/β domains then interact with several other domains (ε, γ, δ, and ζ), all of which participate in T-cell activation via various intracellular activation domains. The TCR complex interacts with MHC-I concurrently with the CD8 co-receptor. The CD8 co-receptor binds to the MHC-I in an antigen independent manner. CD8 directly interacts with Lck, a protein kinase important for activating the TCR receptor complex. The CD8 and Lck interaction also ensures their association with lipid rafts (membrane portion) microdomains, which are hypothesized to organize and encapsulate other relevant signaling moieties (dark spheres). Later stages of activation then lead to CD28 recruitment. If this interaction cascade occurs several times in parallel, T-cells become activated and are able to exert their cytotoxic effects.

FIG. 1B provides an overview of Chimeric Antigen Receptors (CAR). CARs seek to reproduce the complex mechanism of T-cell activation by combining several key activation domains, such as ζ and CD28 in a single synthetically engineered molecule. The CAR then directly interacts with an antigen of choice using specific binding domains. Depicted here is an ankyrin repeat protein (DARPin). It is believed that several such interactions occurring in parallel lead to T-cell activation.

FIG. 1C is an overview of the Tri-TAC technology mimicking the natural activation process. The Tri-TAC was developed to better recapitulate the natural signaling through the TCR, while retaining MHC unrestricted targeting. T-cell activation occurs following ligation of MHC by the TCR and co-receptor on the T cells (either CD4 or CD8) simultaneously bind to conserved regions within the MHC molecule. The co-receptors are specifically located within "lipid rafts", membrane micro domains that are particularly important for TCR signal complex formation. In addition to ensuring the correct microdomain localization of the TCR activation complex, these co-receptors also bind directly to Lck, a protein kinase that is crucial for T-cell activation. As stated previously, none of the traditional chimeric receptors or bi-functional proteins engage the co-receptor molecules or Lck. A molecule was created where the transmembrane and intracellular regions of the CD4 co-receptor, which localize to the lipid raft and bind Lck, respectively, were fused to single-chain antibody that binds CD3 (UCHT1; SEQ ID NO: 13 and 14). This construct is designed to draw the CD3 molecule and the TCR into regions of lipid rafts and bring Lck into the proximity of the TCR, similar to natural MHC binding. To target this receptor, a designed ankyrin repeat (DARPin) was linked to the CD4-UCHT1 chimera to generate a Trifunctional T cell-antigen coupler (Tri-TAC). In this example, the DARPin was specific for the proto-oncogene, HER-2 (erbB-2).

Figure 2A:
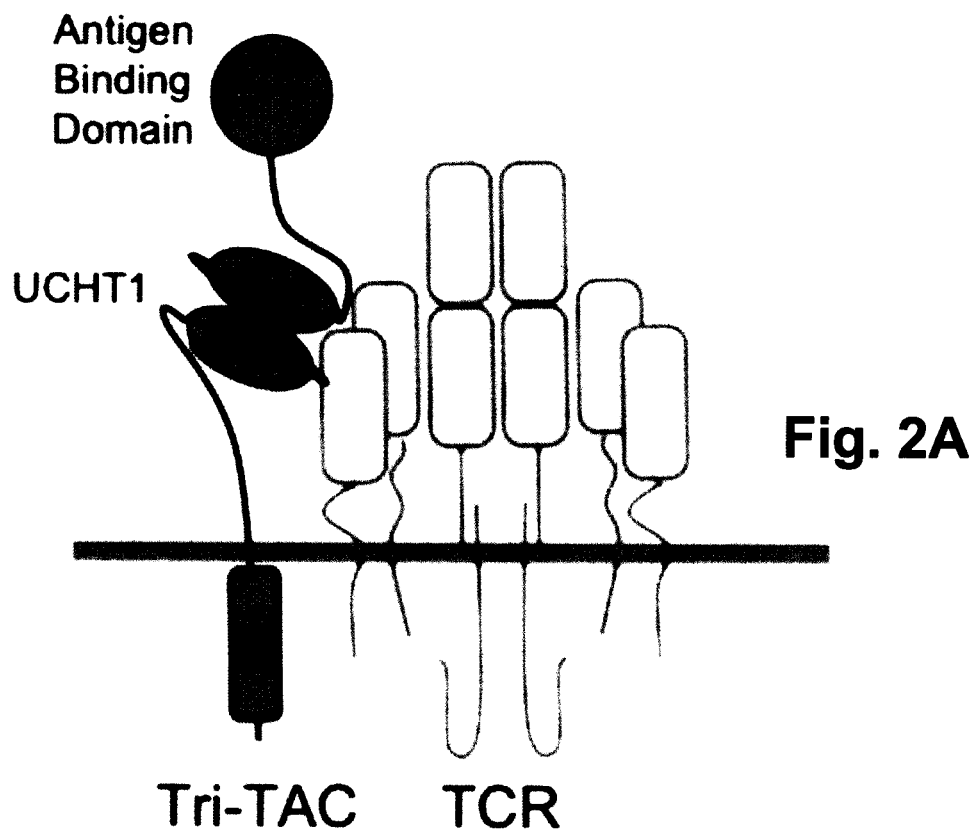
FIG. 2A is a schematic of a Tri-TAC molecule with a generic antigen binding domain.
Figure 2B:
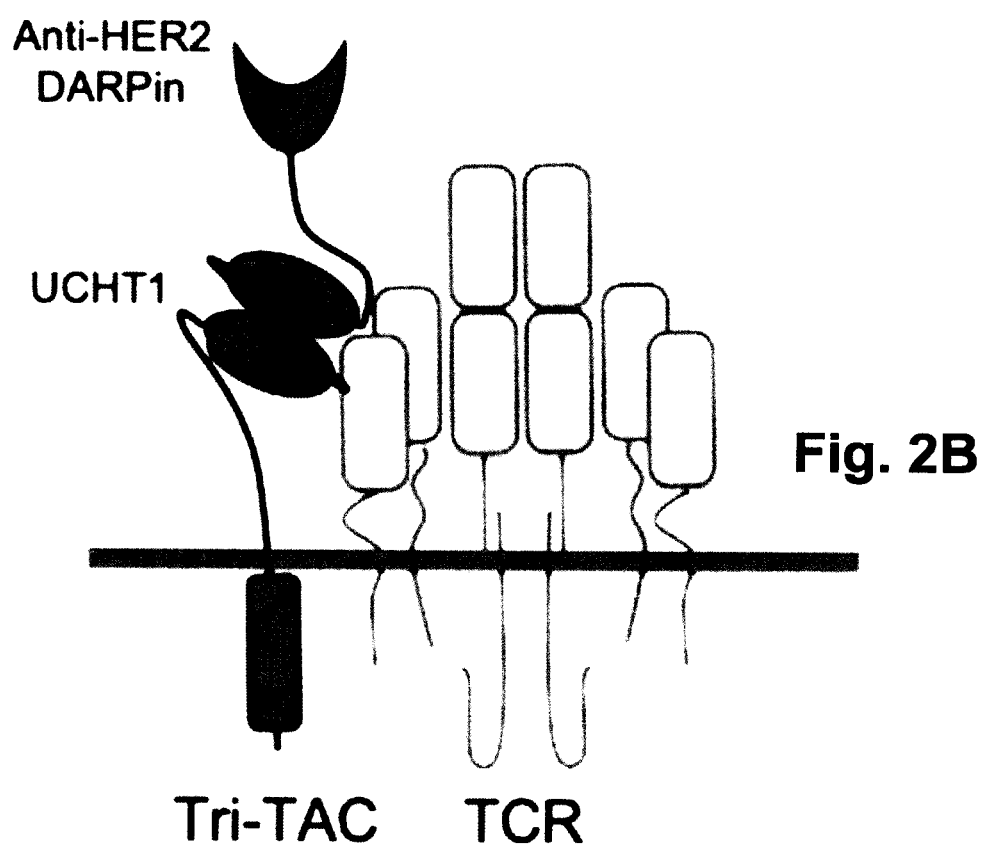
FIG. 2B is a schematic of a Tri-TAC molecule with the Anti-HER-2 DARPin antigen binding domain.

Multiple classes of ligand binding domains can be incorporated into the Tri-TAC molecule (FIG. 2A). The examples herein illustrate Tri-TACs bearing a HER-2-specific DARPin (FIG. 2B) or a BCMA-specific scFv (FIG. 2C).

FIG. 3 illustrates the functionality of a Tri-TAC bearing the HER-2-specific DARPin. Human T cells were engineered to express either the Tri-TAC as disclosed herein or a conventional CAR with the same DARPin. It was determined that in all aspects, T cells engineered with the Tri-TAC demonstrated functionality at least equivalent to a conventional CAR. Interestingly, with regard to 2 parameters (TNF-α production and CD107a mobilization), it was observed that the Tri-TAC was more active than a conventional CAR in some circumstances.

Figure 3A:
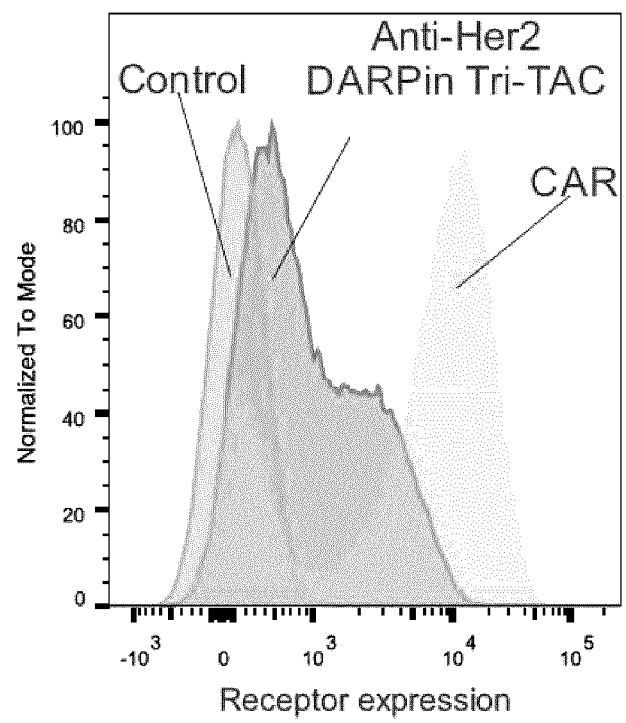
FIG. 3A-FIG. 3B exemplifies T cells engineered with a Tri-TAC or a CD28-based CAR directed against HER-2 using a DARPin.
Figure 3B:
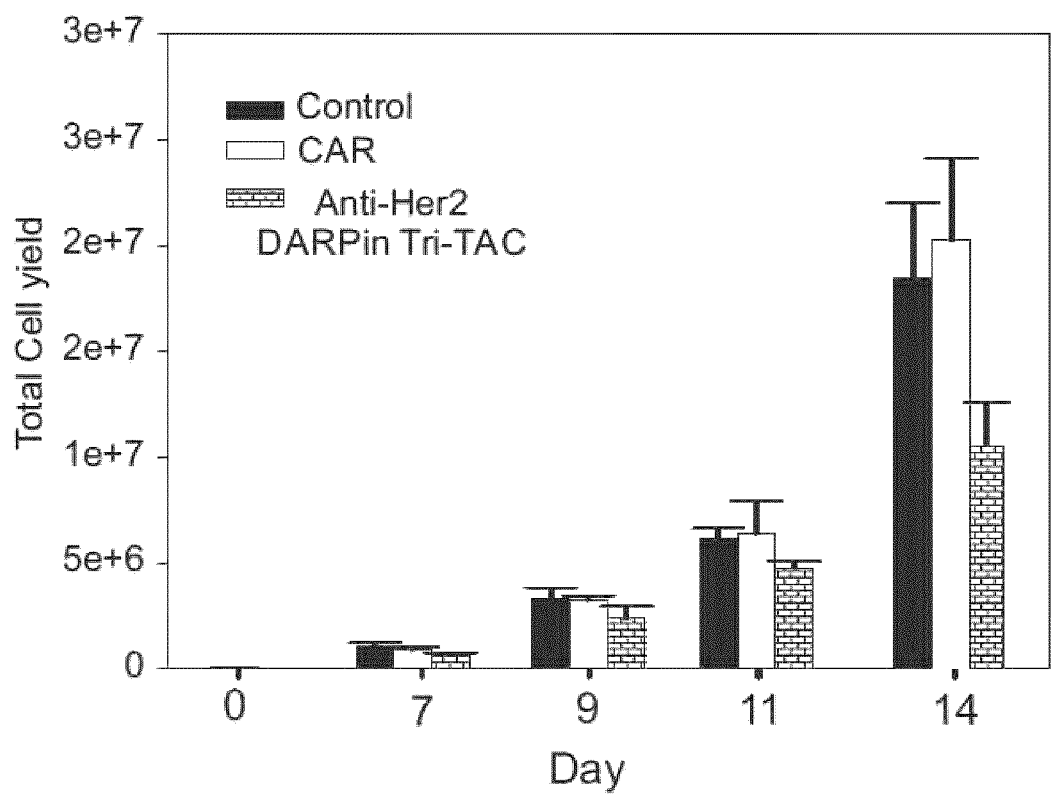

FIG. 3A shows surface expression of Anti-HER-2 DARPin Tri-TAC compared to Anti-HER-2 DARPin CAR, and control T cells. The chimeric receptors were detected by incubation with recombinant HER-2. The Anti-HER-2 DARPin Tri-TAC was expressed well on the surface of the engineered T cells. However, its maximal surface expression was lower compared to the Anti-HER-2 DARPin CAR construct. FIG. 3B shows growth of the engineered T cells cultures. T cells were activated with anti-CD3/anti-CD28 Dynabeads and engineered with lentiviruses encoding the Tri-TAC, CAR or no receptor (control). After 2 weeks, the CAR and control cultures had grown to similar numbers while the Tri-TAC cultures grew slightly more slowly.

Figure 4A:
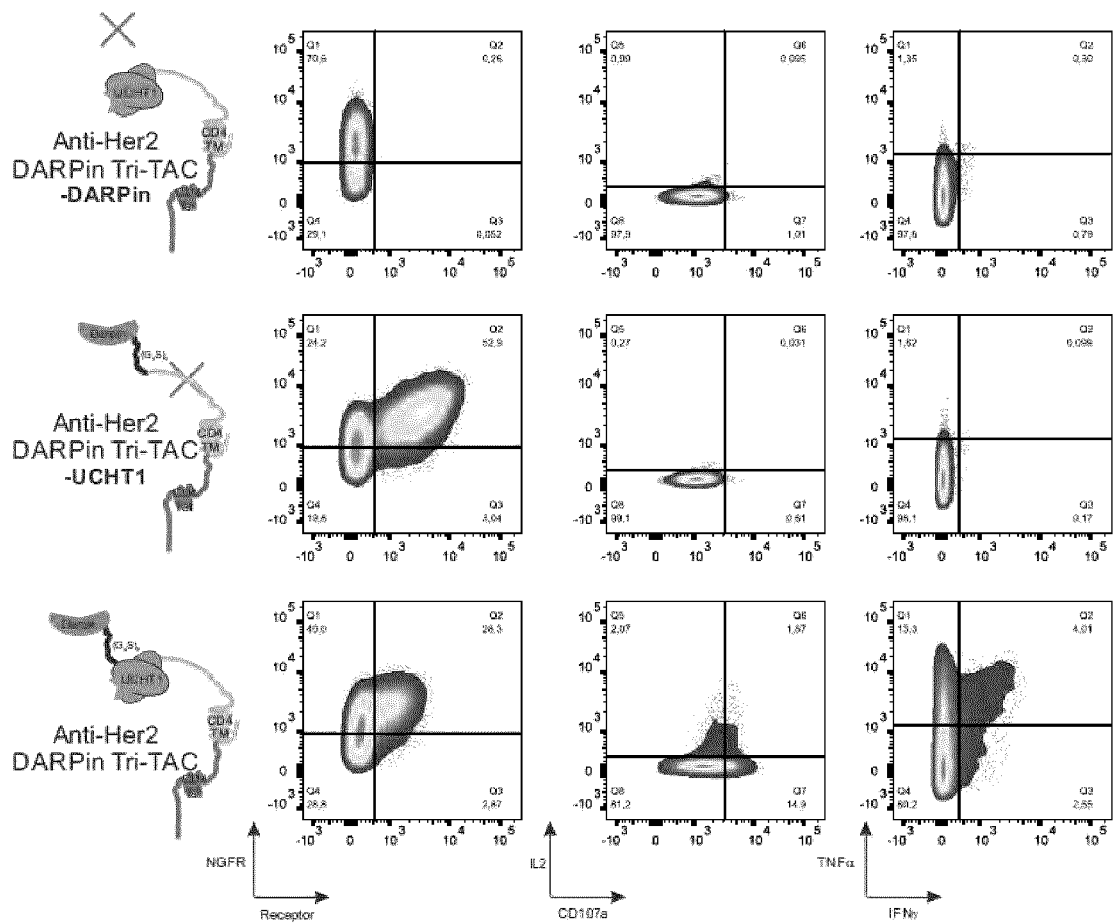
FIG. 4A-FIG. 4B exemplifies receptor surface expression and activation of various anti-HER-2 DARPin Tri-TAC controls. T cells were engineered with a Tri-TAC variant that lacks the targeting element (-DARPin) or a Tri-TAC variant that lacks UCHT1 or the full-length Tri-TAC.
Figure 4B:
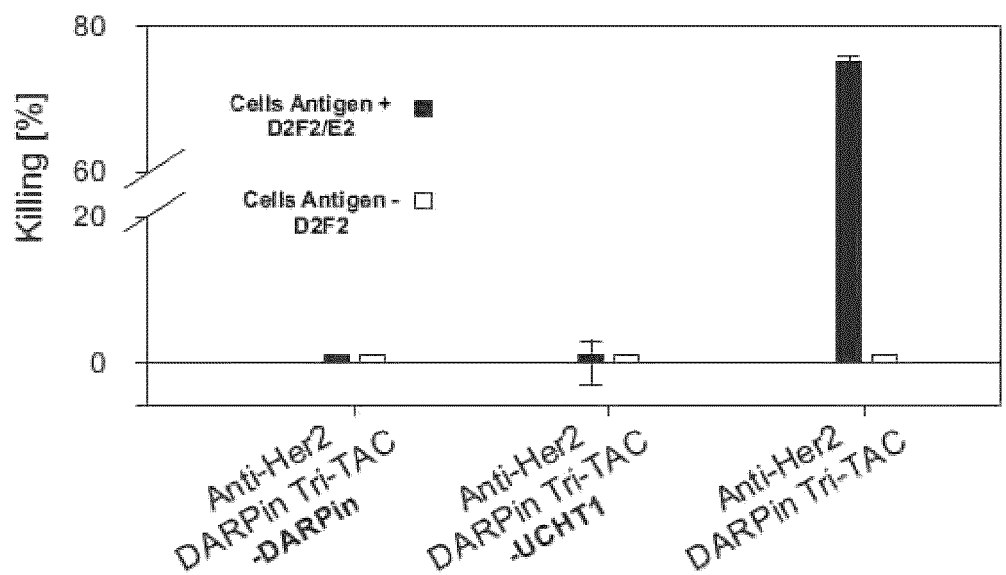

FIG. 4 provides data confirming the importance of both ligand binding domain and the UCHT1 CD3 binding domain for Tri-TAC functionality. T cells were engineered with the full-length Tri-TAC bearing the HER-2 DARPin (FIG. 4A, bottom row), a Tri-TAC variant that lacks the DARPin (FIG. 4A, top row), or a Tri-TAC variant that lacks the UCHT1 (FIG. 4A, middle row). All 3 engineered T cell populations were stimulated with HER-2-positive tumor cells. The T cells engineered with the full-length Tri-TAC could produce IFN-γ, TNF-α and IL-2 following stimulation, whereas the variants failed to produce any cytokine following stimulation. The 3 T cell populations were also co-cultured with D2F2/E2 cells (HER-2-expressing) or D2F2 cells (HER-2-negative) at an effector:target of 4:1 (FIG. 4B). T cells engineered with full-length Tri-TAC demonstrated robust killing against D2F2/E2 cells but did not kill the D2F2 cells. The other Tri-TAC variants lacking either the DARPin or the UCHT1, exhibited no killing.

Figure 5A:
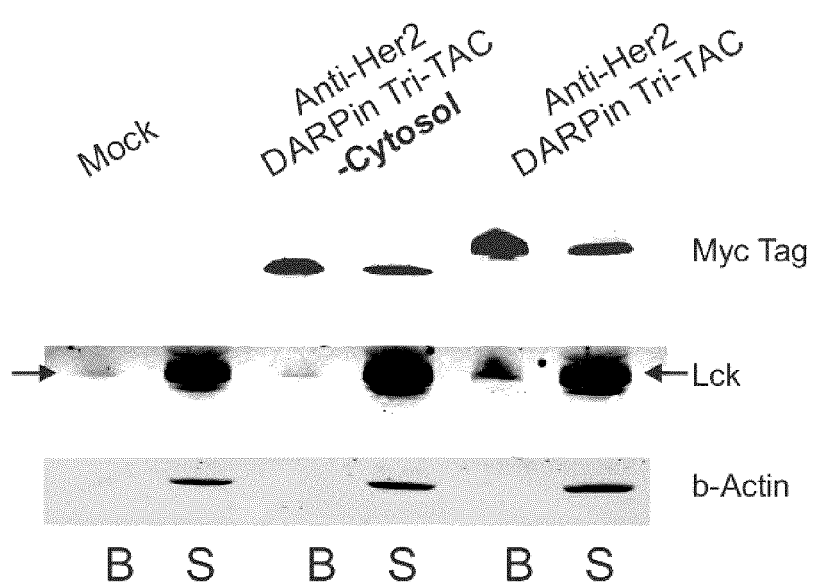
FIG. 5A-FIG. 5B illustrates the Lck interaction with anti-HER-2 DARPin Tri-TAC variants.
Figure 5B:
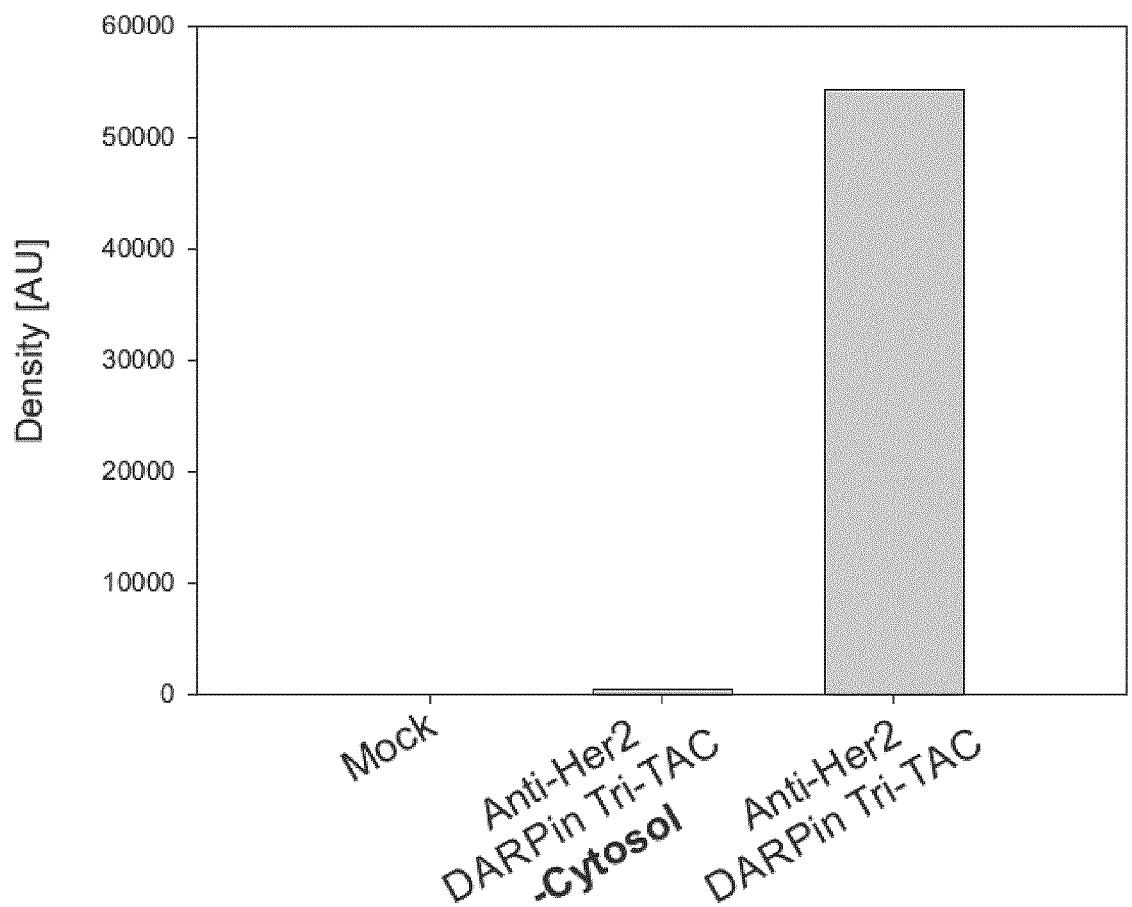

FIG. 5 illustrates Lck interaction with the Tri-TAC. In FIG. 5A, 293™ cells were engineered to express Lck in combination with either the full-length Tri-TAC or a Tri-TAC variant that lacked the cytosolic domain that interacts with Lck. The Tri-TAC receptors were immunoprecipitated with beads carrying recombinant HER-2 protein. The precipitated Tri-TAC was measured by Western blot with an antibody against the myc tag. Co-precipitated Lck was identified by Western blot with an antibody against Lck. (3-Actin was not pulled down and only detected in the supernatant (S). Both full length Tri-TAC and the Tri-TAC that lacked the cytosolic domain were efficiently pulled down and detected in the bound fraction (B). Vector control and TAC without cytosolic domain show comparable levels of background Lck signal. Greater amounts of Lck were co-immunopreciptated with the full-length Tri-TAC relative to the controls. FIG. 5B shows densitometry analysis of the Lck detected in the bound fraction. Signal was corrected relative to the negative control. This data supports that Lck is able to interact with full length Tri-TAC.

Figure 6A:
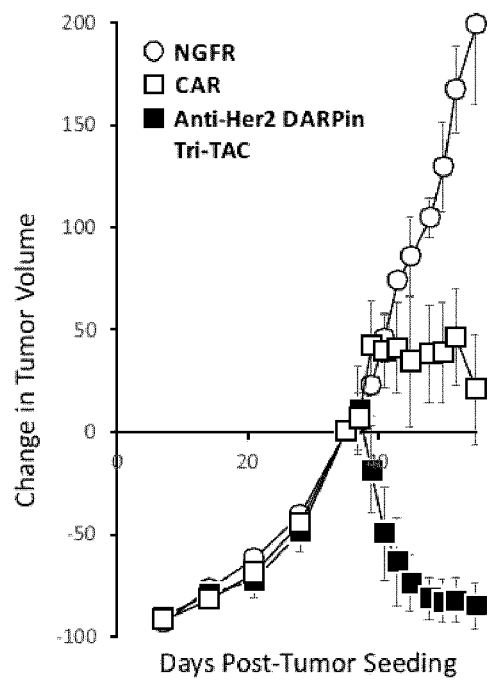
FIG. 6A-FIG. 6B illustrates anti-tumor activity and toxicity of T cells engineered with either the anti-HER-2 DARPin Tri-TAC or the anti-HER-2 DARPin CD28-based CAR. Mice bearing established OVCAR-3 tumors were treated with T cells engineered with the anti-HER-2 DARPin Tri-TAC or the anti-HER-2 DARPin CAR.
Figure 6B:
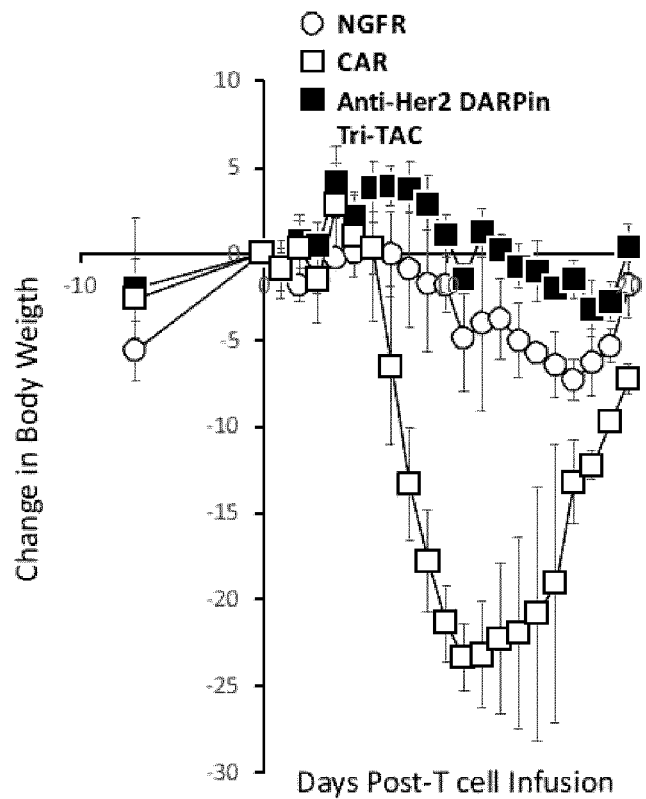

FIG. 6 shows the results of mice treated with vector control (NGFR), Anti-HER-2 DARPin CAR or Anti-HER-2 DARPin Tri-TAC. A xenograft mouse model was used. OVCAR-3 tumor cells were administered to mice subcutaneously and allowed to grow until the tumors reached a size of 100-200 $mm^3$. Engineered T-cells were then administered intravenously. FIG. 6A shows relative tumor progression normalized to tumor size at day of treatment. Anti-HER-2 DARPin Tri-TAC engineered T-cells cause a rapid decrease in tumor volume, control has no effect and CAR cells slow tumor growth and show a delayed reduction in tumor size. FIG. 6B illustrates the relative health of animals was monitored using relative changes in body weight post T-cell infusion. Both control and Anti-HER-2 DARPin Tri-TAC engineered cells show no significant changes in mouse body weight post treatment. In contrast Anti-HER-2 DARPin CAR treated mice, show significant loss in body weight indicative of severe toxicity.

DISCUSSION

Using chimeric receptors to redirect T-cells towards specific targets in an MHC-independent manner is a novel method to treat cancer and may be applicable to infectious diseases where antigens from the pathogen are found on the plasma membrane. The chimeric receptor would result in: (1) specific cytotoxicity against the target cells and (2) minimal off target toxicity. Conventional CARs are limited in this regard because they rely upon a synthetic structure where signaling domains are located in unnatural positions where they may not receive proper regulation and, thus, there is reduced cellular control of specific activity.

The Tri-TAC was designed to re-direct the signaling components of the natural TCR without employing ectopic localization of signaling domains. The Tri-TAC was designed with the following principles: (1) the chimeric receptor should interact and facilitate ordered assembly of key activating protein complexes, (2) the chimeric receptor should take advantage of pre-existing cellular adaptations, such as micro-domain environments, and (3) the chimeric receptor should not possess any activating domains. The Tri-TAC is able to achieve this efficiently and, as the data demonstrates, at rates of activation that are equal to, if not better than, that of a 2nd generation CAR.

The Tri-TAC is suited for further integration with additional designed co-receptors to further fine tune T-cell activation. Tri-TAC appears to exhibit lower toxicity than existing CARs. Anti-HER-2 DARPin CARs show mild off target killing at high cell to target ratios, which may become problematic when used in therapies. However, Anti-HER-2 DARPin Tri-TAC, which is as functional as the traditional CAR, did not display off-target effects. Since DARPins bind targets with high affinity, off-target effects may be more common on cells that express high levels of a chimeric receptor that employs a DARPin. Therefore, without being bound by theory, the low surface expression of the Tri-TAC may be advantageous as it reduces the likelihood of such off-target effects.

The modular nature of the Tri-TAC technology allows fine tuning of the T-cell activation process. For example, the recruitment of the TCR complex is modulated by engineering Tri-TAC molecules with a lower CD3 affinity. This mimics the natural low TCR affinity while retaining a high affinity targeting domain to detect cancer targets. Unlike the classical CAR, the Tri-TAC technology is engineered to more closely resemble this.

The presented Tri-TAC technology is a highly efficient molecular tool that is able to (1) efficiently trigger T-cell activation and cytotoxicity, (2) is able to do this by mimicking natural T-cell activation and (3) does not require activation domains of its own.

Example 2. Mutation of UCHT1 Influences Tri-TAC Function

Figure 7A:
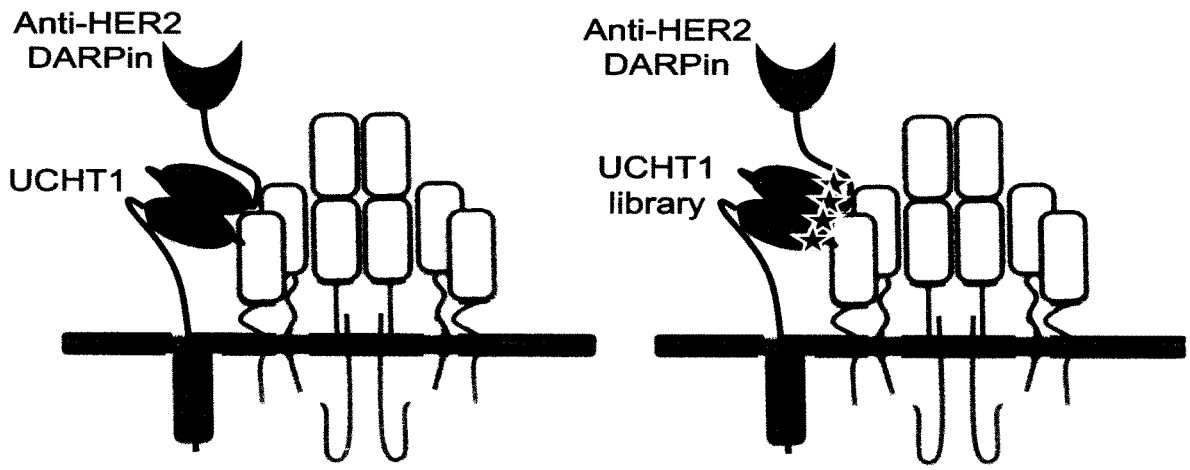
FIG. 7A-FIG. 7C illustrate wild type anti-HER-2 DARPin Tri-TAC compared to a library of Tri-TAC variants where the UCHT1 sequences were randomly mutagenized at sites predicted to bind to CD3.
Figure 7B:
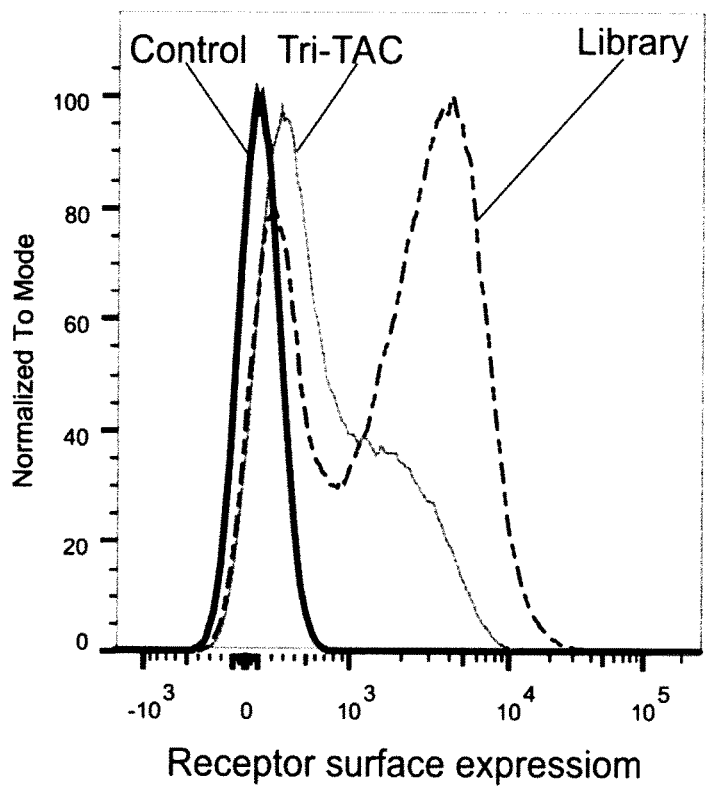
Figure 7C:
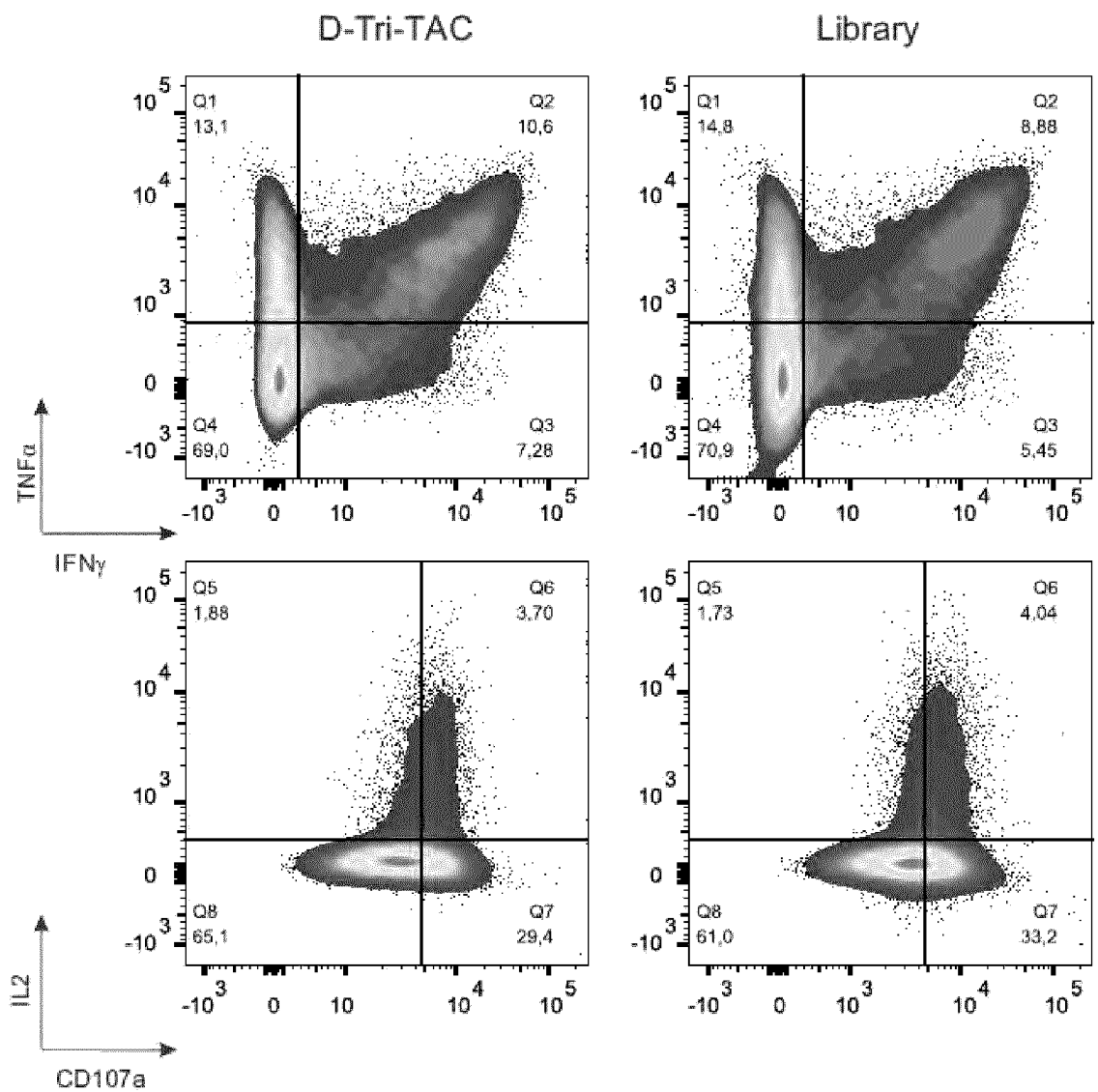

FIG. 7 shows wild type anti-HER-2 DARPin Tri-TAC compared to a library of Tri-TAC variants where the UCHT1 sequences were randomly mutagenized at sites predicted to bind to CD3. To build the library, 24 amino acids within UCHT1 that were found on the binding surface of UCHT1 and CD3 epsilon were randomly mutagenized, which yielded a theoretical number of 480 unique clones. FIG. 7A shows the schematic representation of the mutant library. Analysis of surface expression revealed that the mutant Tri-TACs was expressed at higher levels than the original Tri-TAC (FIG. 7B). T cells engineered with the original Tri-TAC or the mutant library were tested for functionality. The T cells engineered with the mutant library retained functionality, indicating the presence of UCHT1 mutants that retain Tri-TAC function (FIG. 7C).

Figure 8A:
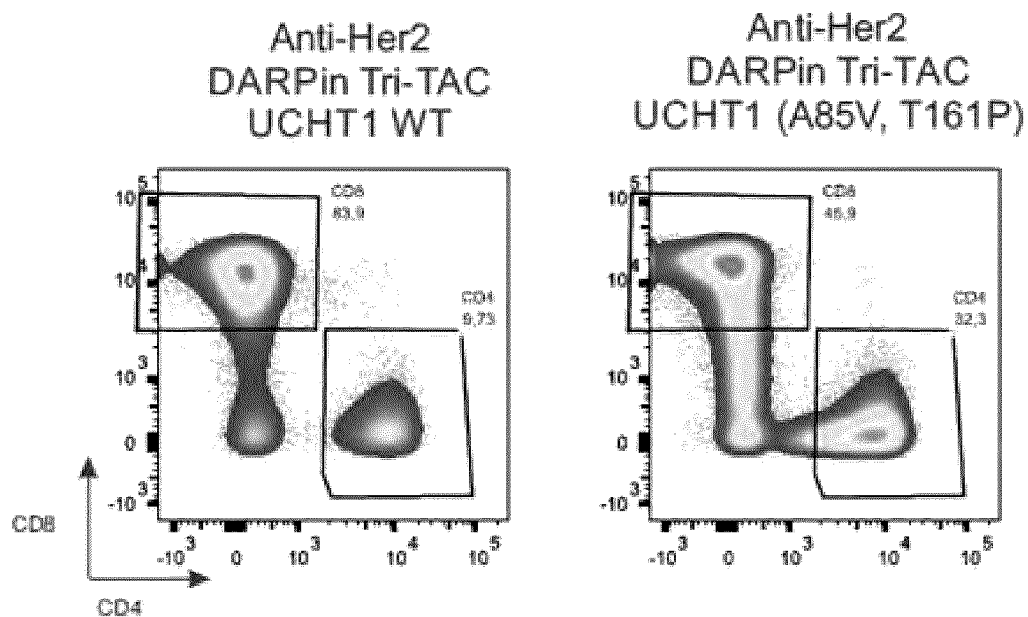
FIG. 8A-FIG. 8C illustrates a comparison of Anti-HER-2 DARPin Tri-TAC carrying either the wild type UCHT1 (UCHT1 wt) or a mutated UCHT1 (UCHT1A85V/T161P) selected following a screen of the mutagenized library disclosed in FIG. 7B.
Figure 8B:
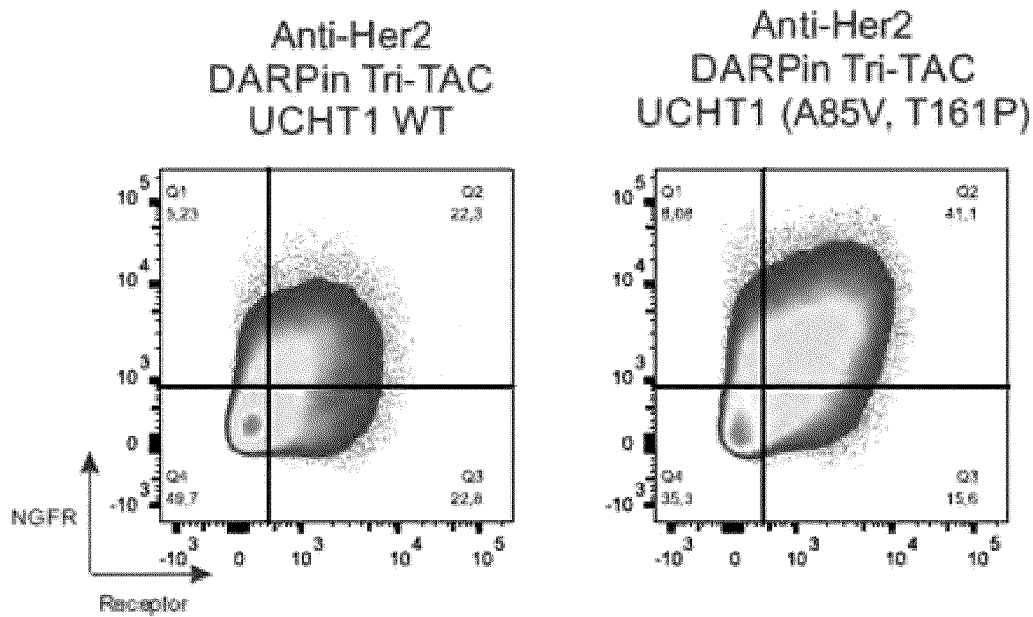
Figure 8C:
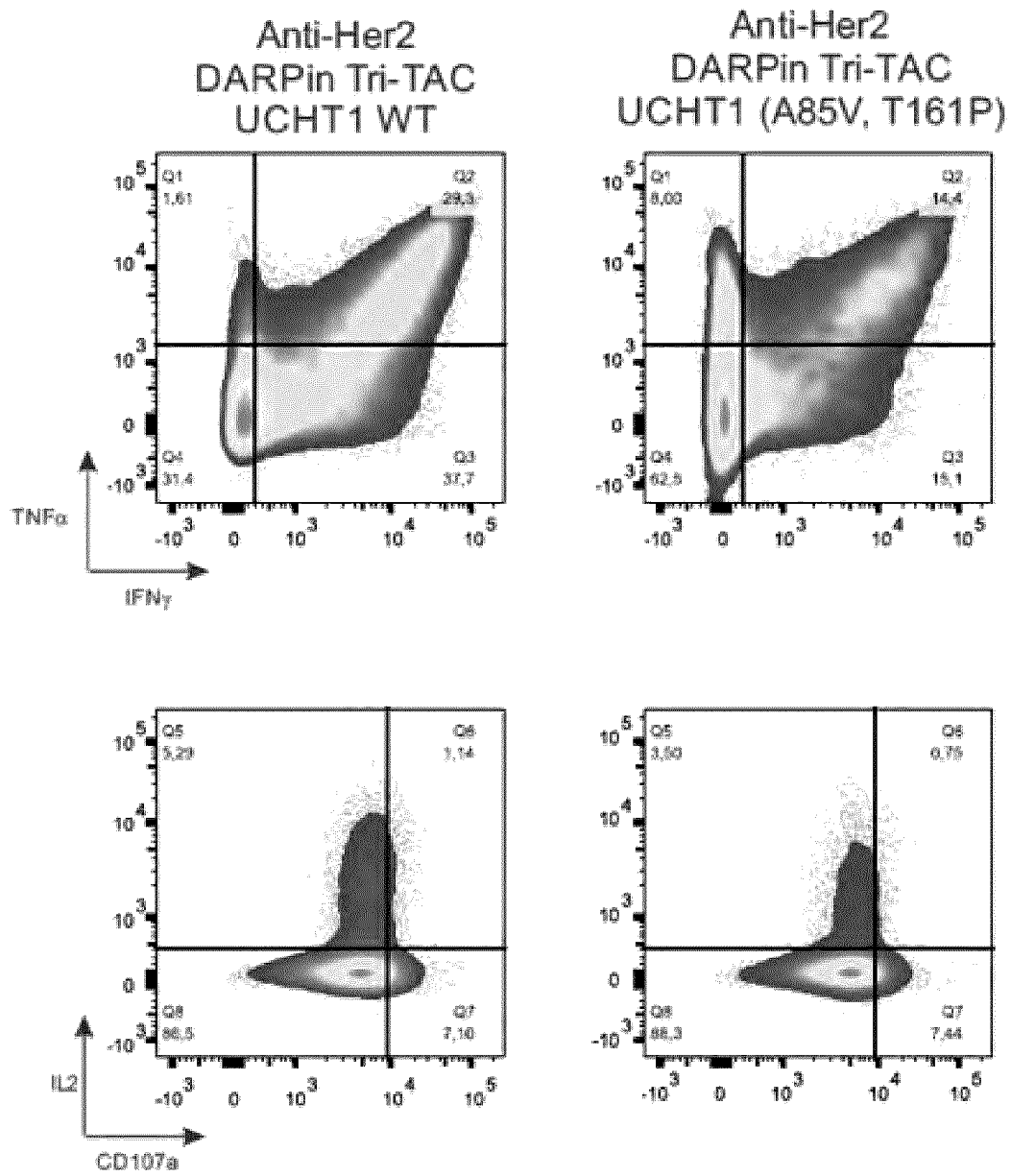

FIG. 8 shows enhanced surface expression of Tri-TACs carrying UCHT1 mutants selected from the library. T cells engineered with the Tri-TAC library were subject to a screen that selected for the ability of the Tri-TAC to stimulate T cells. Random selection of sequences from the selected library yielded a mutant where UCHT where A85 was replaced by V and T161 was replaced by P (SEQ ID NO: 23 and 24). T cells were engineered with either the original Anti-HER-2 DARPin Tri-TAC or a variant carrying the UCHT1 with the A85V and T161P mutations. It has been noted that T cell cultures engineered with the original Tri-TAC were biased towards expansion of CD8+ T cells relative to control T cells. T cells engineered with the A85V, T161P mutant Tri-TAC did not reveal a bias towards CD8+ T cell expansion (FIG. 8A). Comparison of surface expression revealed that the Tri-TAC carrying the A85V, T161P mutant was expressed at higher levels on the surface of T cells compared to the original Tri-TAC (FIG. 8B). With regards to functionality, T cells engineered with the A85V, T161P mutant Tri-TAC produced lower levels of cytokine and experienced reduced degranulation following stimulation with HER-2. These results demonstrate that mutation of UCHT1 can impact multiple aspects of Tri-TAC function.

Figure 9A:
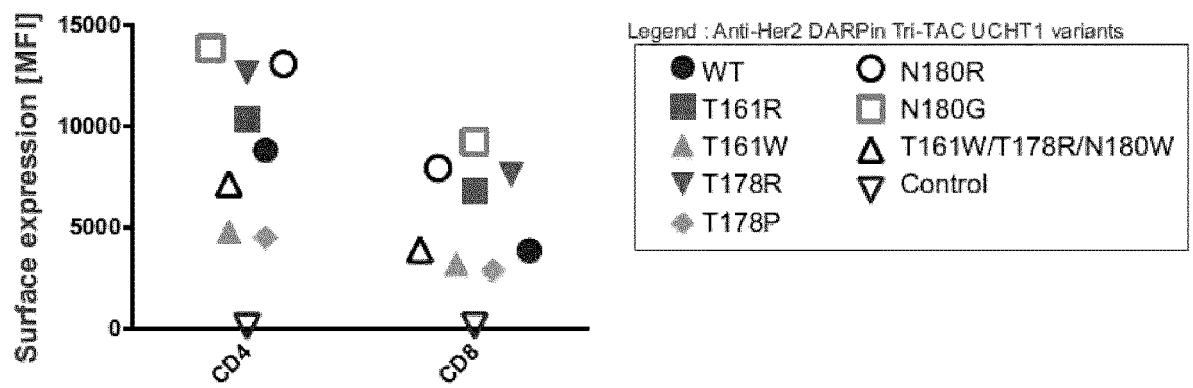
FIG. 9A-FIG. 9C illustrates the phenotypic and functional analysis of a variety of anti-HER-2 DARPin Tri-TACs with UCHT1 point mutants that were isolated from the screen in FIG. 7B.
Figure 9B:
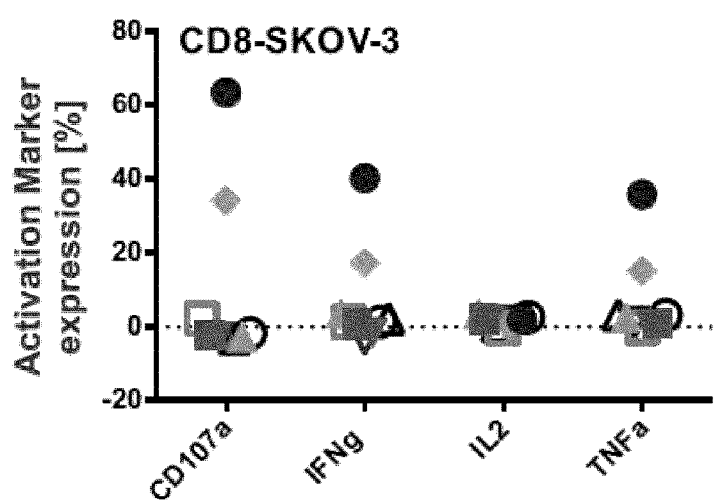
Figure 9C:
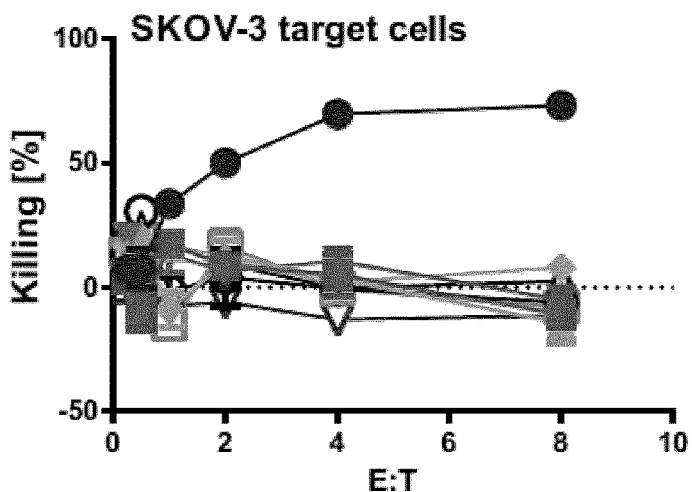

In FIG. 9, seven additional point mutations were tested. Four of the mutants (T161R, T178R, N180R and N180G) resulted in enhanced surface expression of the Tri-TAC (FIG. 9A). The various mutants were tested for functionality following stimulation with either A549 or SKOV-3 cells. All of the mutants, with the exception of T178P, displayed greatly impaired cytokine production (FIG. 9B) and none of the mutants demonstrated cytotoxicity against HER-2-positive target cells (FIG. 9C). These results exemplify that individual mutations can completely abrogate the Tri-TAC function.

Figure 10:
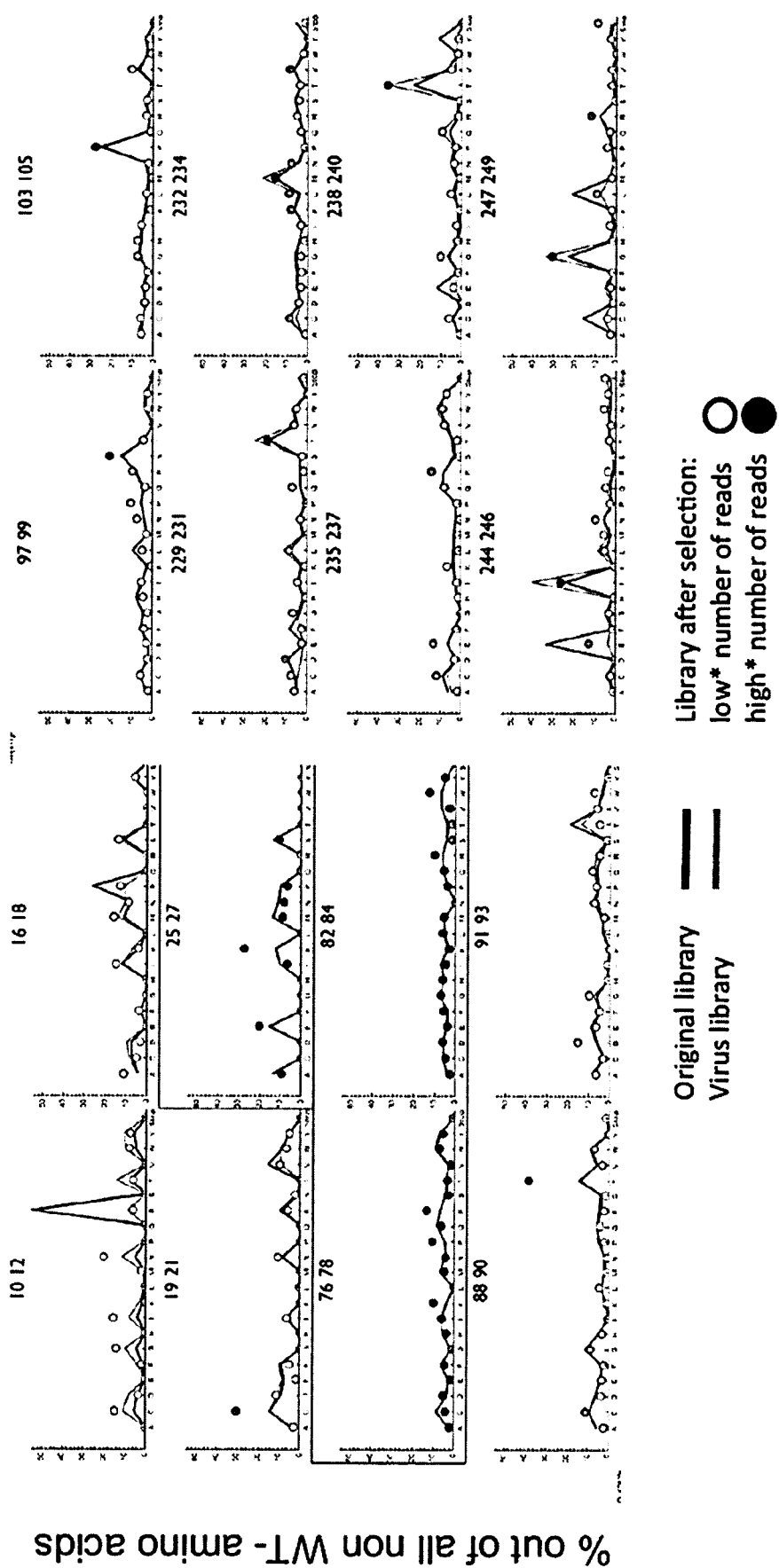
FIG. 10 exemplifies the results of an analysis for enrichment of specific amino acids following selection of the randomly mutagenized library. Enrichment was defined by comparing the sequences of the UCHT1 library post-selection to (i) the original library described in FIG. 8 and (ii) the same library after packaging into lentivirus.

FIG. 10 shows the results of an analysis for enrichment of specific amino acids following selection of the randomly mutagenized library. Enrichment was defined by comparing the sequences of the UCHT1 library post-selection to (i) the original library described in FIG. 7, and (ii) the same library after packaging into lentivirus. Mutations that were enriched following selection were determined by comparing frequencies in: (i) the original library described in FIG. 8 (black line); (ii) the library packaged into lentivirus (gray line); and (iii) the-post selection library (circles). Mutations that showed distinct enrichment, as indicated by full circles, were considered candidates (FIG. 10). Empty circles represented a low number of reads. The single most obvious mutation found was the replacement of tyrosine (Y) with threonine (T) at position 88-90.

FIG. 11 shows sequence alignment of UCHT1 and UCHT1 variants. The sequence of UCHT1 and UCHT1 (Y182T) (SEQ ID NO: 26) is shown in FIG. 11A. The sequence of UCHT1 and a humanized UCHT1 (huUCHT1) (SEQ ID NO: 29) is shown in FIG. 11B. The Y→T mutation was inserted into the corresponding site in huUCHT1 to yield huUCHT1 (Y177T) (FIG. 11C) (SEQ ID NO: 28.)

The Y182T and Y177T mutants were analyzed in vitro based on their surface expression phenotype, and other functional properties, namely, cell growth and cytotoxicity.

Figure 12:
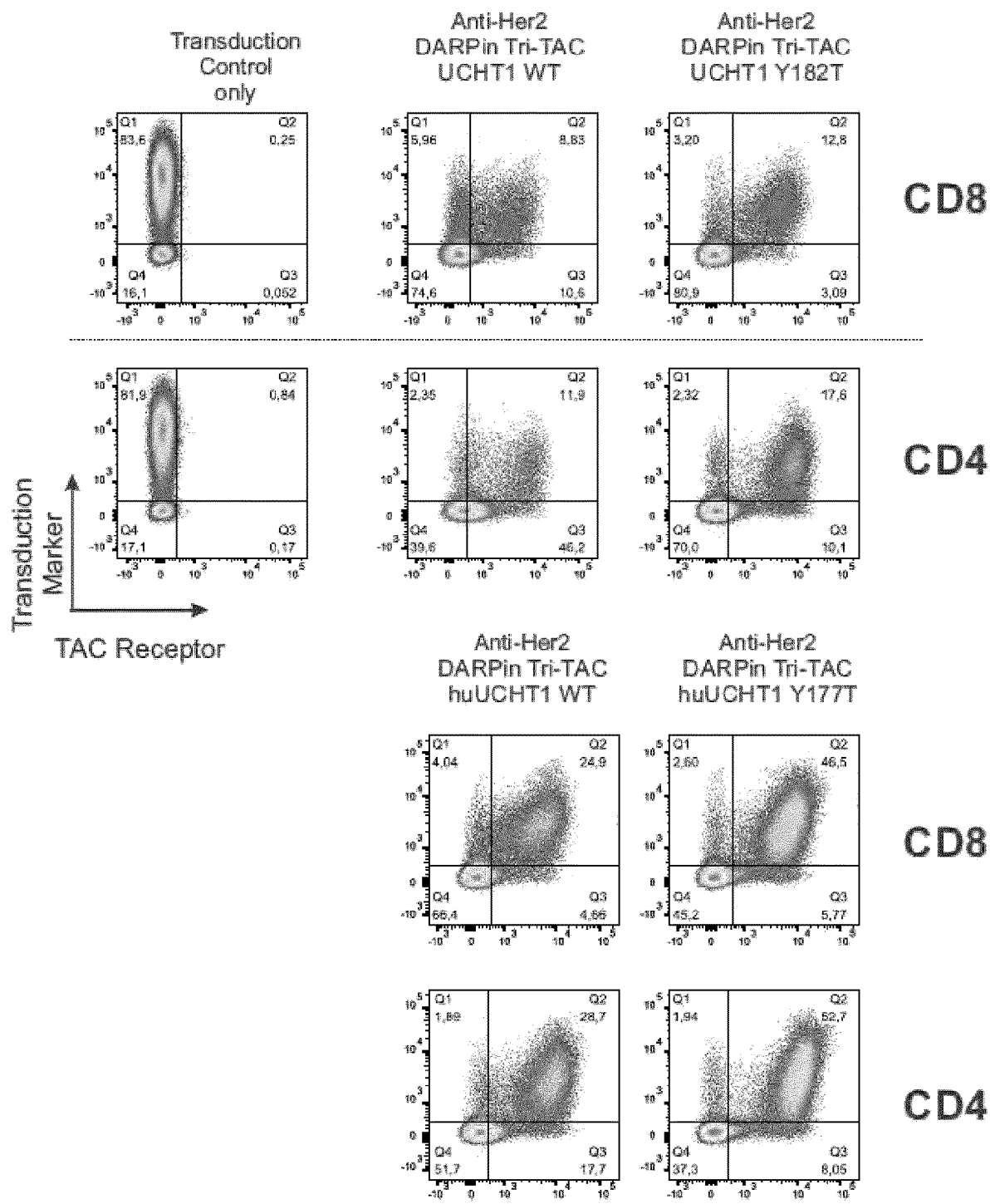
FIG. 12 illustrates surface expression of the Y182T/Y177T mutants relative to non-mutated UCHT1/huUCHT1.

FIG. 12 exemplify that Tri-TACs carrying the Y→T mutation, either UCHT1(Y182T) or huUCHT1(Y177T) are expressed at higher levels on the surface of engineered T cells compared to Tri-TACs carrying UCHT1 and huUCHT1, respectively. Human PBMC were activated with anti-CD3/anti-CD28, transduced with lentivirus (MOI=10) expressing only: (i) NGFR, (ii) the prototypic Tri-TAC molecule, (iii) the Tri-TAC carrying UCHT1(Y182T), (iv)

the Tri-TAC carrying huUCHT1, and (v) the Tri-TAC carrying huUCHT1(Y177T). After 14 days, the cells were stained with antibodies against NGFR (Transduction marker), the TAC receptor, and the T cell markers CD8 and CD4. Cells were gated on CD8 (upper panels) and CD4 (lower panels). In each case, the presence of the Y182T/Y177T mutation improved surface expression of the TAC receptor. This was observed across multiple donors and a representative plot is shown.

FIG. 12 also reveals enhanced surface expression of the Tri-TAC carrying huUCHT1 compared to the original Tri-TAC that carried UCHT1 indicating that the mutations incorporated into UCHT1 during the humanization introduced attributes that influenced surface expression.

Figure 13:
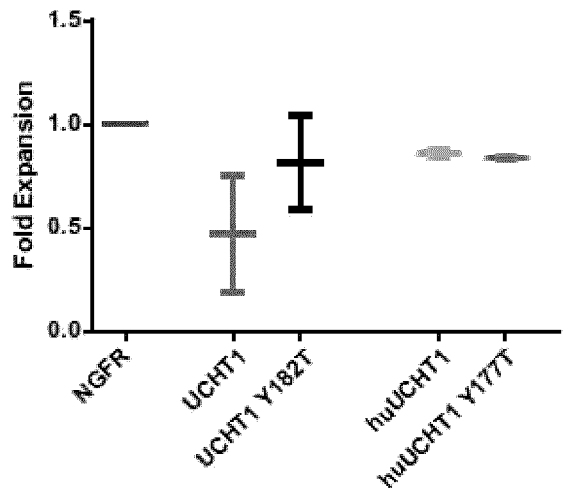
FIG. 13 illustrates the growth of T cell cultures engineered with either a control lentivirus (NGFR) or lentiviruses encoding Tri-TACs carrying the wild type UCHT1, UCHT1 (Y182T), huUCHT1, or huUCHT1(Y177T).

FIG. 13 demonstrates that T cells engineered with Tri-TACs carrying either huUCHT1, muUCHT1(Y182T) or huUCHT1(Y177T) expanded to a greater extent than T cells engineered with the original Tri-TAC carrying UCHT1. Human PBMC were activated with anti-CD3/anti-CD28, transduced with lentivirus (MOI=10) expressing only: (i) NGFR, (ii) the prototypic Tri-TAC molecule, (iii) the Tri-TAC carrying UCHT1(Y182T), (iv) the Tri-TAC carrying huUCHT1, and (v) the Tri-TAC carrying huUCHT1 (Y177T). After 14 days of growth, the cells were enumerated to determine fold-expansion over the baseline. The fold expansion was normalized to the expansion of the control cells engineered with NGFR lentivirus alone. The average of two different donors is shown in FIG. 13. T cells engineered with Tri-TAC with UCHT1(Y182T) expanded to a greater extent than T cells engineered with the original Tri-TAC carrying UCHT1. T cells engineered with Tri-TACs with huUCHT1 and huUCHT1(Y177T) expanded to the same extent; both of which displayed greater expansion than the original Tri-TAC carrying UCHT1.

Again, it should be noted that the Tri-TAC carrying UCHT1 demonstrated impaired expansion relative to control T cells, whereas the Tri-TAC carrying huUCHT1 revealed no impairment in expansion relative to controls.

Figure 14:
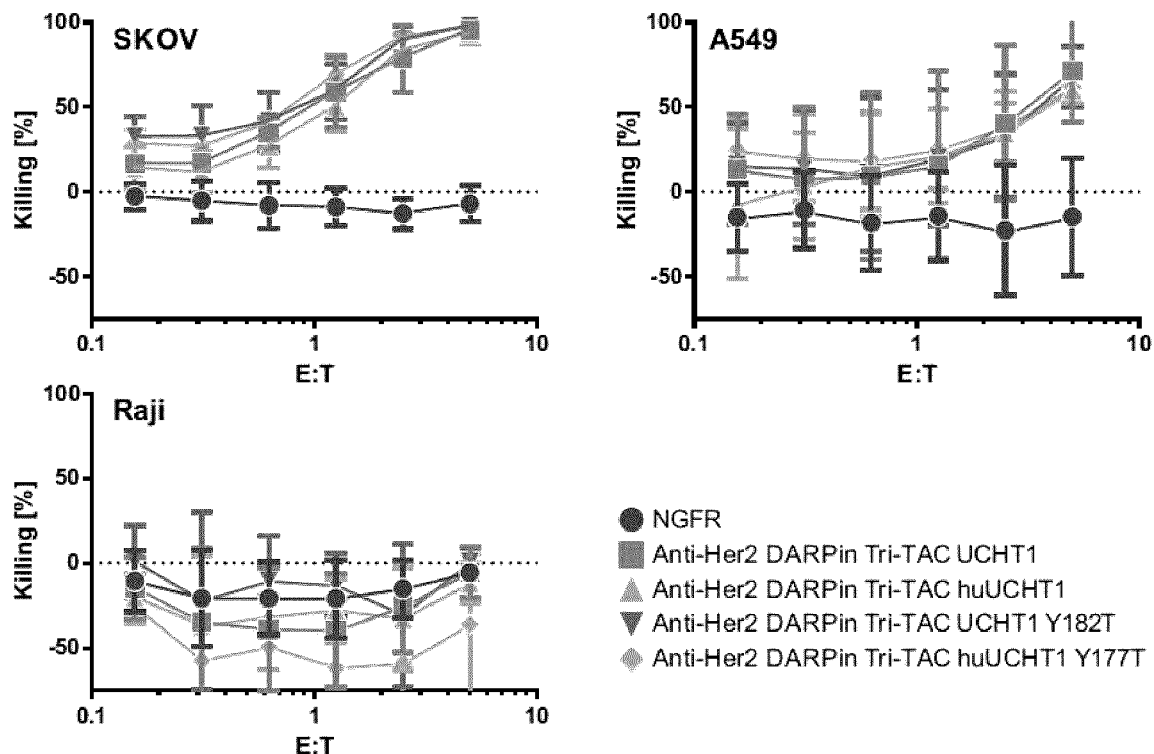
FIG. 14 illustrates a cytotoxicity assay comparing T cell cultures engineered with either a control lentivirus (NGFR) or lentiviruses encoding Tri-TACs carrying the wild type UCHT1, UCHT1(Y182T), huUCHT1, or huUCHT1 (Y177T). All Tri-TACs were specific for HER-2. SKOV and A549 are HER-2-positive targets. Raji are HER-2-negative targets.

FIG. 14 describes the cytotoxicity of the Tri-TAC variants. T cells were engineered with the original Tri-TAC, the Tri-TAC carrying huUCHT1 and the Tri-TACs carrying the UCHT1 variants with the Y→T mutation. All Tri-TACs were targeted with the anti-HER-2 DARPin. Cytotoxicity was assessed by incubating the engineered T cells with HER-2-positive targets (SKOV-3 and A549) or the HER-2-negative target LOXIMVI. The average of two different donors is shown. All T cell populations revealed comparable cytotoxicity.

As in FIG. 14, T cells were engineered with the Tri-TAC carrying huUCHT1 or the Tri-TACs carrying the huUCHT1 variants with the Y→T mutation [huUCHT1(Y177T)]. Both Tri-TACs were targeted with the anti-HER-2 DARPin. Control T cells were engineered with a Tri-TAC that carries huUCHT1(Y177T) but not tumor binding domain. The T cells were used to treat the OVCAR-3 xenograft mouse model described in FIG. 6. Engineered T-cells were administered intravenously tumors reached a size of 100-200 mm$^3$. The data shows relative tumor progression normalized to tumor size at day of treatment. FIG. 17 (panels A-C) illustrate the results for T cells produced from donor A. FIG. 17 (panels D-F) show the results for T cells produced from donor B.

Figure 15A:
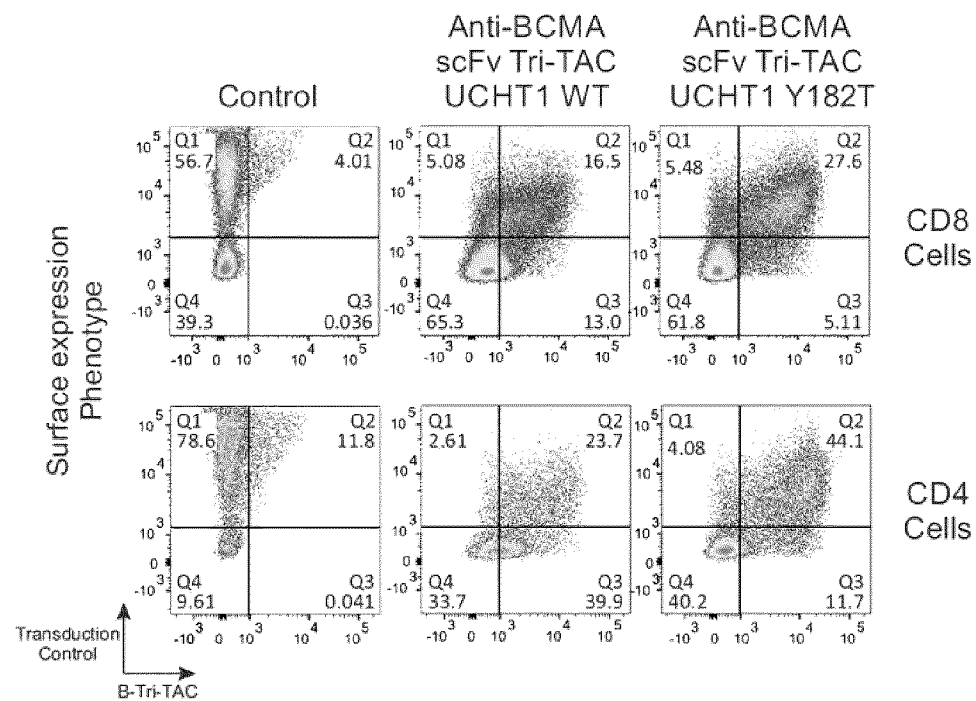
FIG. 15A-FIG. 15C illustrate the functionality of T cells engineered with a Tri-TAC carrying wild type UCHT1 and a Tri-TAC carrying UCHT1(Y182T). Both Tri-TACs carry an scFv against the myeloma target, BCMA.
Figure 15B:
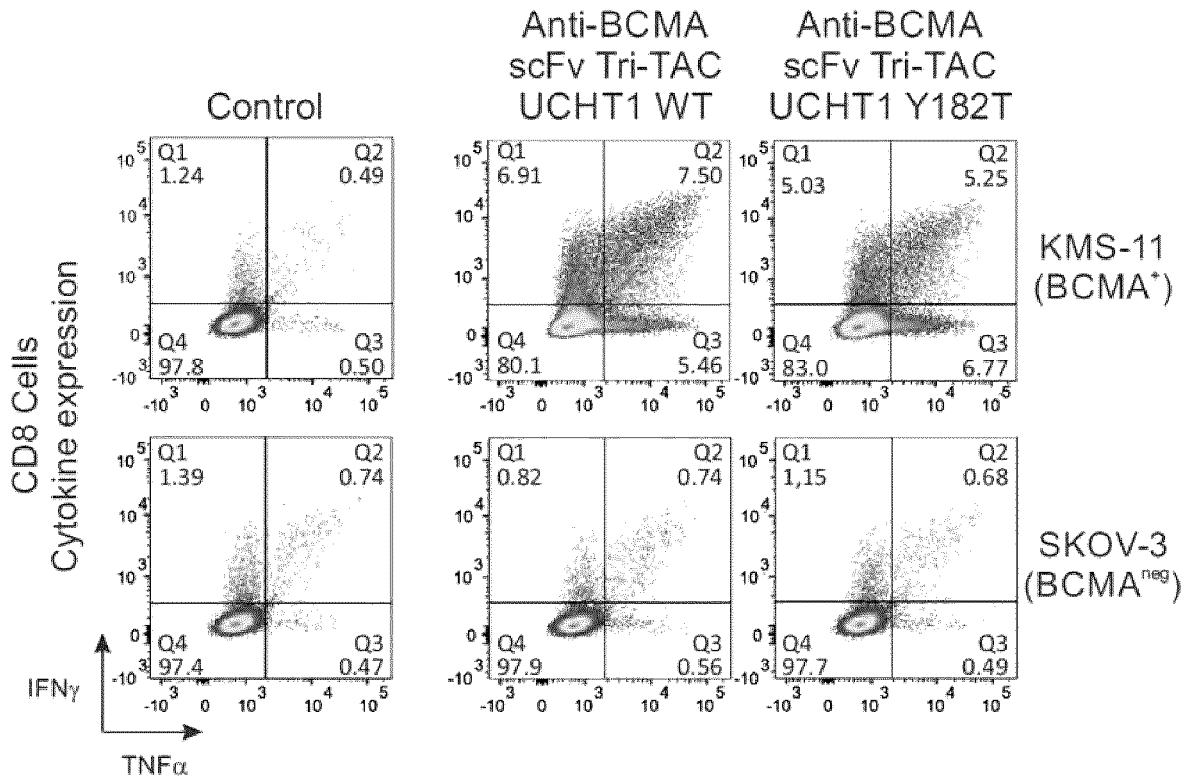
Figure 15C:
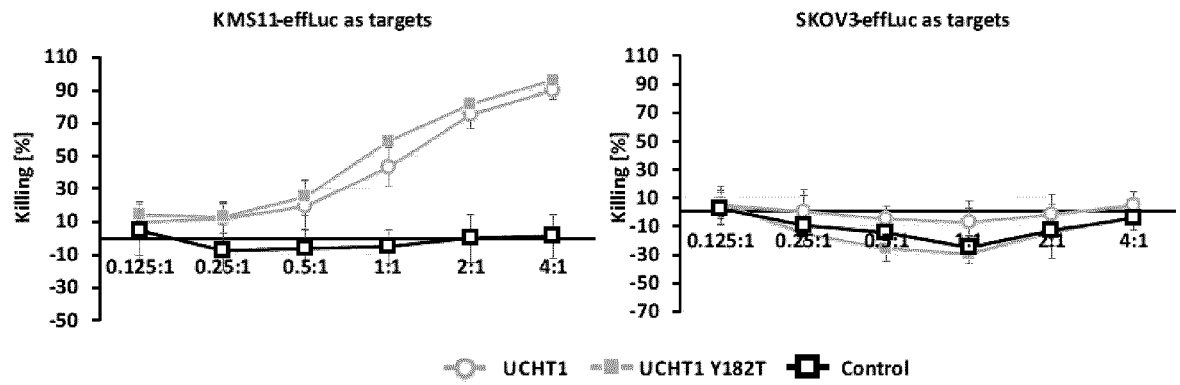

FIG. 15 shows the in vitro characterization of T cells engineered with Tri-TACs carrying an scFv specific for the myeloma target, BCMA. T cells were engineered with either the original Tri-TAC or the Tri-TAC with the UCHT1 (Y182T). T cells were engineered with a control lentivirus, a lentivirus expressing the original Tri-TAC or a lentivirus expressing the Tri-TAC with UCHT1(Y182T) at an MOI of 5. Cell surface expression of the Tri-TAC was assessed by incubating engineered cells with the recombinant BCMA-Fc which was subsequently measured by flow cytometry. Cytokine production was assessed by co-culturing engineered or control cells with BCMA-positive (KMS-11) or BCMA-negative (SKOV-3) cell lines. After 4h of co-culture cells were processed for intracellular staining of cytokines and cytokine production was measured by flow cytometry. Cytotoxicity was assessed by co-culturing engineered or control cells with BCMA-positive (KMS-11) or BCMA-negative (SKOV-3) cell lines and viability was assessed after 6h of co-culture. As described previously, a higher fraction of T cells were engineered with the Tri-TAC UCHT1(Y182T) compared to the original Tri-TAC; the Tri-TAC UCHT1 (Y182T) was also expressed at higher levels than the original Tri-TAC (FIG. 15A). Despite the higher levels of expression, T cells engineered with the original Tri-TAC and the Tri-TAC UCHT1(Y182T) demonstrated similar functionality with regard to cytokine production (FIG. 15B) and cytotoxicity on BCMA-expressing targets (KMS-11; FIG. 15C).

Figure 16:
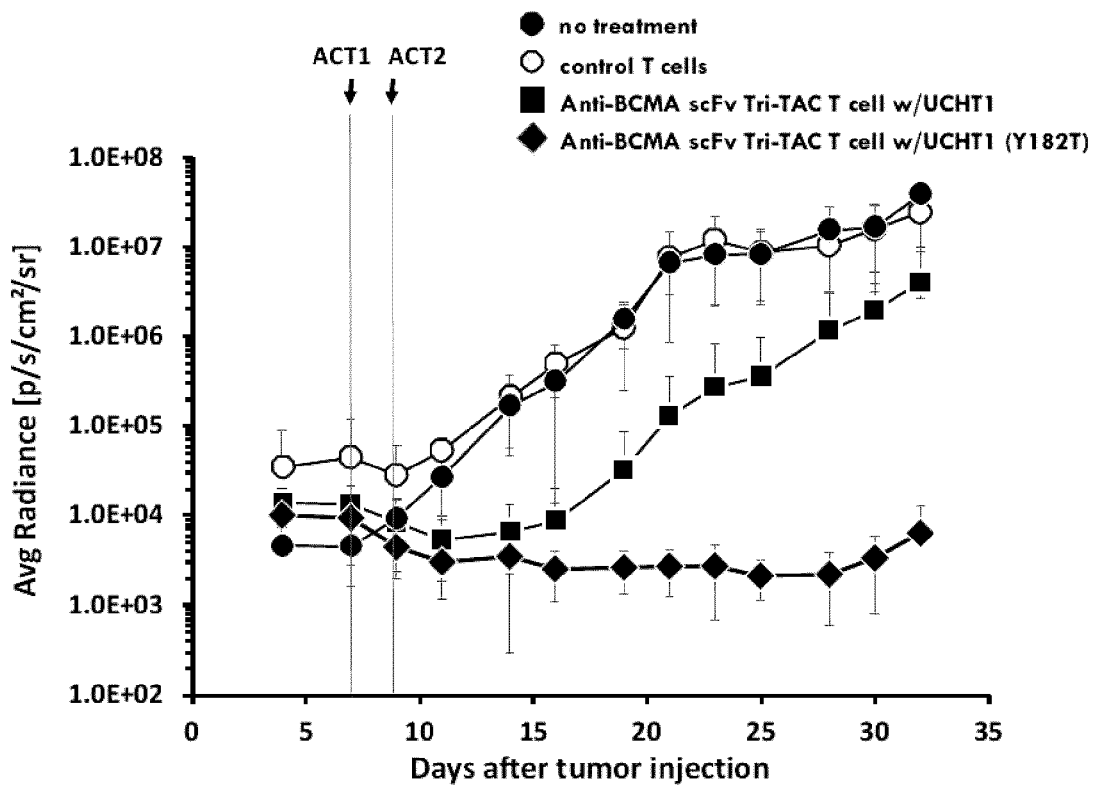
FIG. 16 illustrates anti-myeloma activity of T cells engineered with BCMA-specific Tri-TACs carrying either wild type UCHT1 or UCHT1(Y182T). Mice bearing the KMS-11 myeloma were treated with T cells engineered to express NGFR, Tri-TAC with wild type UCHT1 or Tri-TAC with UCHT1(Y182T). Tumor growth was monitored by bioluminescence, which is reported in the figure. Control T cells were engineered with a lentivirus without a chimeric receptor.

FIG. 16 illustrates enhanced anti-tumor efficacy of T cells engineered with Tri-TAC carrying UCHT1(Y182T). As in FIG. 15, T cells were engineered with a control lentivirus, a lentivirus expressing the original Tri-TAC or a lentivirus expressing the Tri-TAC with UCHT1(Y182T) at an MOI of 5. Multiple myeloma tumors were established in immunodeficient NRG mice by inoculation with KMS-11 cell lines had been engineered with enhance firefly luciferase (KMS-11$^{eff}$). Seven days after the myeloma tumors were established the mice were treated a split dose of engineered T-cells administered 48h apart. Mice received equal doses of control T cells or T cells engineered with the 2 BCMA-specific Tri-TACs (original Tri-TAC with UCHT1 and variant Tri-TAC with UCHT1(Y182T)). Mouse tumor burden was monitored at regular by in vivo bioluminescent imaging. The data in the figure reflect tumor growth, as assessed by increased bioluminescence, over time. Tumor growth was comparable in mice that received no treatment and mice that received control T cells. Tumor growth was initially slowed in mice treated with T cells engineered with the original Tri-TAC but tumor control in these mice was lost approximately 2 weeks post-treatment. In contrast, the T cells engineered with the Tri-TAC carrying UCHT1(Y182T) exhibited tumor regression and long-term tumor control.

Discussion

The Tri-TAC was designed based on the philosophy that alterations of the various components could modulate receptor function. Here, modifications to the contact region between UCHT1 and CD3 were investigated by mutating individual amino acids in UCHT1. First, it was demonstrated that point mutations in UCHT1 influence surface expression of the receptor. While most mutations increased surface expression, some mutations diminished surface expression (ex. T161W, T178P). Second, it was noted that mutation to UCHT1 also improves the overall yield of T cells during the manufacturing process. Finally, it was found that mutations to UCHT1 could reverse the skewing of the manufactured product towards CD8+ T cells, which is a common feature of the original Tri-TAC receptor.

In many cases, the mutations impaired the production of cytokines IFN-γ, TNF-α and IL-2 and also impaired cytotoxicity. We uncovered a specific mutation (Y182T) that yields a Tri-TAC with properties that are highly attractive for manufacturing (no impairment in T cell expansion, no suppression of CD4+ T cell expansion) without compromising the functionality of the receptor. Moreover, T cells engineered with the Tri-TAC (UCHT1 Y182T) displayed greater anti-tumor activity than T cells engineered with the original Tri-TAC.

A Tri-TAC carrying the humanized variant of UCHT1 (huUCHT1) also demonstrated enhanced manufacturing properties relative to the original Tri-TAC. These enhanced features are due to the mutations in huUCHT1 associated with the humanization.

Collectively, these data demonstrate that subtle mutations of UCHT1 dramatically influence the function of Tri-TACs. While these studies to date have focused on Oncology applications, this knowledge also applies to the use of Tri-TAC receptors for other application (ex. Auto-immunity, allergy) where mutations, other than the ones described herein, may be of value for those specific applications.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A nucleic acid sequence encoding a T cell-antigen coupler (TAC) comprising:
   (a) a first polynucleotide sequence encoding an antigen-binding antibody fragment or DARPin that selectively binds a target antigen;
   (b) a second polynucleotide sequence encoding a humanized UCHT1 (huUCHT1) ligand comprising the amino acid sequence of SEQ ID NO: 28; and
   (c) a third polynucleotide sequence encoding a T cell co-receptor domain polypeptide comprising a CD4 cytosolic domain and a CD4 transmembrane domain.

2. The nucleic acid sequence of claim 1, wherein the antigen-binding antibody fragment or DARPin specifically binds the target antigen.

3. The nucleic acid sequence of claim 1, wherein the target antigen is a tumor antigen.

4. The nucleic acid sequence of claim 1, wherein:
   (a) the antigen-binding antibody fragment or DARPin, the huUCHT1 ligand, and the T cell co-receptor domain polypeptide are directly fused;
   (b) the antigen-binding antibody fragment or DARPin and the huUCHT1 ligand are directly fused, and joined to the T cell co-receptor domain polypeptide by a linker; or
   (c) the huUCHT1 ligand and the T cell co-receptor domain polypeptide are directly fused, and joined to the antigen-binding antibody fragment or DARPin by a linker.

5. A vector comprising the nucleic acid sequence of claim 1.

6. The vector of claim 5, further comprising a promoter functional in a mammalian cell.

7. An engineered T cell comprising the nucleic acid sequence of claim claim 1.

8. A pharmaceutical composition comprising the engineered T cell of claim 7, and a pharmaceutically acceptable carrier.

9. A method of treating a cancer expressing a target antigen in an individual in need thereof, comprising administering to the individual an engineered T cell according to claim 7.

10. The method of claim 9, wherein the cancer is a solid cancer or a liquid cancer.

* * * * *